US012728127B2

(12) United States Patent
Borsadia et al.

(10) Patent No.: US 12,728,127 B2
(45) **Date of Patent: *Sep. 8, 2026**

(54) TRANSDERMAL DELIVERY OF DEXTROMETHORPHAN

(71) Applicant: SHINKEI THERAPEUTICS, INC., Princeton, NJ (US)

(72) Inventors: Suresh Borsadia, Plainsboro, NJ (US); Kalpana Patel, West Windsor, NJ (US); Hock S. Tan, East Brunswick, NJ (US); Krunal Raval, Ahmedabad (IN)

(73) Assignee: SHINKEI THERAPEUTICS, INC., Princeton, NJ (US)

( * ) Notice: Subject to any disclaimer, the term of this patent is extended or adjusted under 35 U.S.C. 154(b) by 649 days.

This patent is subject to a terminal disclaimer.

(21) Appl. No.: 17/915,687

(22) PCT Filed: Mar. 29, 2021

(86) PCT No.: PCT/US2021/024572

§ 371 (c)(1),
(2) Date: Sep. 29, 2022

(87) PCT Pub. No.: WO2021/202329

PCT Pub. Date: Oct. 7, 2021

(65) Prior Publication Data

US 2024/0216358 A1 Jul. 4, 2024

Related U.S. Application Data

(60) Provisional application No. 63/001,607, filed on Mar. 30, 2020.

(51) Int. Cl.

| | |
|---|---|
| ***A61K 31/485*** | (2006.01) |
| ***A61K 9/70*** | (2006.01) |
| ***A61K 47/14*** | (2017.01) |
| ***A61K 47/32*** | (2006.01) |

(52) U.S. Cl.
CPC .......... *A61K 31/485* (2013.01); *A61K 9/7061* (2013.01); *A61K 9/7069* (2013.01); *A61K 47/14* (2013.01); *A61K 47/32* (2013.01)

(58) Field of Classification Search
CPC .. A61K 31/485; A61K 9/7061; A61K 9/7069; A61K 47/14; A61K 47/32
See application file for complete search history.

(56) References Cited

U.S. PATENT DOCUMENTS

| | | | | |
|---|---|---|---|---|
| 5,985,317 | A | 11/1999 | Venkateshwaran et al. | |
| 6,335,030 | B1 * | 1/2002 | Hoeck | A61K 9/7053 424/443 |
| 11,382,869 | B2 | 7/2022 | Borsadia | |
| 2002/0035105 | A1 * | 3/2002 | Caruso | A61K 31/55 514/657 |
| 2006/0223786 | A1 * | 10/2006 | Smith | A61K 31/137 514/649 |
| 2010/0311697 | A1 * | 12/2010 | Went | A61P 25/00 514/297 |
| 2013/0331803 | A1 * | 12/2013 | Fleschhut | A61K 9/7069 514/279 |

FOREIGN PATENT DOCUMENTS

| | | | |
|---|---|---|---|
| WO | 1996008229 | A2 | 3/1996 |
| WO | 2010005507 | A1 | 1/2010 |
| WO | 2019070864 | A1 | 4/2019 |
| WO | 2019209940 | A1 | 10/2019 |

OTHER PUBLICATIONS

Nguyen et al. "Dextromethorphan: An update on its utility for neurological and neuropsychiatric disorders." Pharmacology & Therapeutics, 2016, 159: 1-22. (Year: 2016).*

Notification of Transmittal of the International Search Report and the Written Opinion for corresponding PCT Application No. PCT/US2021/024572, dated Jun. 10, 2021, 15 pages.

* cited by examiner

*Primary Examiner* — Doan T Phan
(74) *Attorney, Agent, or Firm* — NIXON & VANDERHYE, PC

(57) ABSTRACT

Provided herein are novel transdermal delivery devices (or patches) comprising dextromethorphan, pharmaceutical compositions comprising dextromethorphan, methods of preparation thereof, and methods of administering dextromethorphan transdermally. Also provided herein are methods of treating various diseases and disorders such as neurological diseases or disorders (e.g., PBA) using the transdermal delivery devices and/or pharmaceutical compositions herein.

17 Claims, 10 Drawing Sheets

Cumulative permeated DXM, µg/cm2

Figure 1:
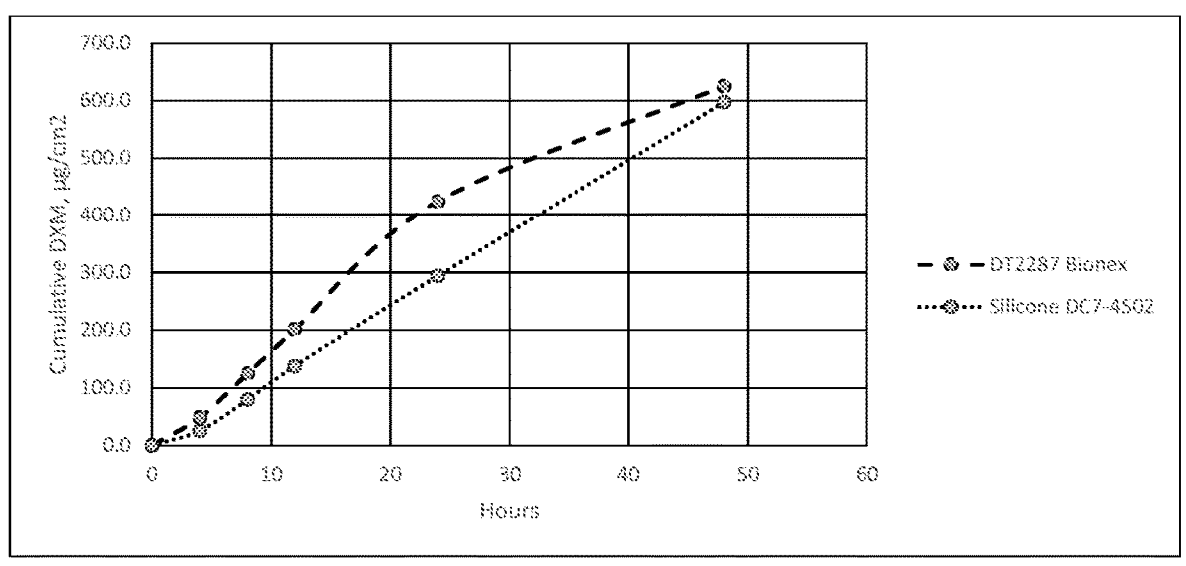

400.0
350.0
300.0
250.0
200.0
150.0
100.0
50.0
0.0
-50.0

0 5 10 15 20 25 30

Hours

No IPM
7.7% IPM
10% IPM

TRANSDERMAL DELIVERY OF DEXTROMETHORPHAN

This application is the U.S. national phase of International Application No. PCT/US2021/024572, filed Mar. 29, 2021, which designated the U.S. and claims benefit to U.S. Provisional Application No. 63/001,607, filed Mar. 30, 2020, the entire contents of each of which are herein incorporated by reference.

In various embodiments, the present disclosure generally relates to transdermal delivery devices comprising dextromethorphan, methods of preparing, and uses thereof, for example, for use in treating a disease or disorder such as a neurological disease described herein.

BACKGROUND

NUEDEXTA® (dextromethorphan hydrobromide and quinidine sulfate) capsules, 20 mg/10 mg is a combination product containing dextromethorphan hydrobromide (an uncompetitive N-methyl-D-aspartate [NMDA] receptor antagonist and sigma-1 agonist) and quinidine sulfate (a CYP450 2D6 inhibitor). This product is indicated for the treatment of pseudobulbar affect (PBA). Dextromethorphan hydrobromide is the pharmacologically active ingredient of NUEDEXTA® that acts on the central nervous system (CNS). Quinidine sulfate is a specific inhibitor of CYP2D6-dependent oxidative metabolism used in NUEDEXTA® to increase the systemic bioavailability of dextromethorphan.

The recommended starting dose of NUEDEXTA® (dextromethorphan hydrobromide and quinidine sulfate) capsules, 20 mg/10 mg is one capsule daily by mouth for the initial seven days of therapy. On the eighth day of therapy and thereafter, the daily dose should be a one capsule every 12 hours for a total of two capsules daily. The need for continued treatment should be reassessed periodically, as spontaneous improvement of PBA occurs in some patients.

The most common adverse reactions (incidence of ≥3% and two-fold greater than placebo) in patients taking NUEDEXTA® in descending order are diarrhea, dizziness, cough, vomiting, asthenia, peripheral edema, urinary tract infection, influenza, increased gamma glutamyltransferase, and flatulence. The following adverse reactions have been reported with the use of the individual component dextromethorphan: drowsiness, dizziness, nervousness or restlessness, nausea, vomiting, and stomach pain.

BRIEF SUMMARY

In various embodiments, the present disclosure is based in part on the unexpected discovery that it is possible to administer dextromethorphan transdermally with a continuously high flux of dextromethorphan from the transdermal delivery devices (patches) herein. The transdermal delivery of dextromethorphan herein achieves therapeutically effective plasma concentrations of dextromethorphan, for example, for treating a disease or disorder herein, such as PBA. Compared to the currently available oral delivery through formulations such as Nuedexta®, the transdermal delivery of dextromethorphan herein has numerous advantages and solves many of the unmet medical needs of such oral formulations. For example, the transdermal delivery device or formulations (e.g., adhesive compositions) herein can be administered to achieve a therapeutically effective plasma concentration without regard to whether a CYP2D6 inhibitor such as quinidine is co-administered. As such, the transdermal delivery devices or formulations herein can be administered to transdermally deliver dextromethorphan to subjects who are sensitive or intolerant to CYP2D6 inhibitors such as quinidine. The transdermal delivery devices or formulations herein can be conveniently administered to transdermally deliver dextromethorphan to a subject with or without first determining whether the subject is a poor metabolizer, an intermediate metabolizer, or an extensive metabolizer of dextromethorphan. Administering dextromethorphan using the transdermal delivery devices or formulations herein can also provide superior clinical experience compared to Nuedexta®, for example, with more accurate dosing, less frequent dosing, reduced potential for side effects associated with quinidine and/or higher exposure (e.g., $C_{max}$) of dextromethorphan, reduced pill burden, and better patient compliance.

In various embodiments, provided herein are novel transdermal delivery devices (or patches) comprising dextromethorphan, pharmaceutical compositions (e.g., transdermal formulations such as adhesive compositions) comprising dextromethorphan, methods of preparation thereof, and methods of administering dextromethorphan transdermally. The transdermal delivery devices, pharmaceutical compositions, and methods herein are useful in treating various diseases and disorders such as neurological diseases or disorders (e.g., PBA).

Some embodiments of the present disclosure are directed to transdermal delivery devices comprising dextromethorphan. Typically, the transdermal delivery device is a drug-in-adhesive (DIA) matrix type patch, such as a single layer DIA patch. In some embodiments, the transdermal delivery device can have additional layers, such as an optional reservoir layer. Other suitable patch designs are described herein. In some embodiments, the transdermal delivery device comprises, consists essentially of, or consists of a backing layer, a drug-in-adhesive layer, and optionally a release liner. The drug-in-adhesive layer typically includes an adhesive composition described herein. In some embodiments, the drug-in-adhesive layer comprises dextromethorphan, a skin permeation enhancer, a pressure sensitive adhesive, and optionally a crystallization inhibitor. The drug-in-adhesive layer typically includes dextromethorphan as the only active ingredient. The dextromethorphan and skin permeation enhancer are typically dispersed (e.g., homogeneously dispersed or dissolved) in the pressure sensitive adhesive. In some embodiments, the drug-in-adhesive layer is a homogeneous mixture. In some embodiments, the skin permeation enhancer is isopropyl myristate. In some embodiments, the pressure sensitive adhesive is an acrylate based pressure sensitive adhesive, such as Duro-Tak 87-2287. It was also discovered that the inclusion of a crystallization inhibitor, a vinylpyrrolidone polymer (Plasdone K29/32), in dextromethorphan transdermal patches significantly enhanced the permeation of dextromethorphan from the patches, in vitro and in vivo. Accordingly, in some embodiments, the crystallization is present, which is preferably a vinylpyrrolidone polymer, such as vinyl pyrrolidone homopolymer (or povidone), for example, Povidone K30, Plasdone K29/32 and the alike. The transdermal delivery device typically is in the form of a monolithic patch, which can have an active surface area of, for example, about 30 $cm^2$ to about 100 $cm^2$. The transdermal delivery device typically includes sufficient amount of dextromethorphan to provide a daily dose of about 15 mg to about 50 mg, such as about 35 mg, of dextromethorphan to a subject in need. The transdermal delivery device typically has a dextromethorphan flux of at least about 200 $ug/cm^2/day$, when measured in vitro using human cadaver skin, such as about 200-800 ug/cm$^2$/day, about 300-800 ug/cm$^2$/day, about 400-800 ug/cm$^2$/day, about 500-800 ug/cm$^2$/day, etc. Suitable types and amounts of the ingredients of the transdermal delivery device include those described herein in any combinations. Methods of preparing the transdermal delivery devices or formulations herein are also provided in the present disclosure.

In some embodiments, the present disclosure also provides a method of treating a disease or disorder described herein in a subject (typically a human subject) in need thereof comprising transdermally delivering a therapeutically effective amount of dextromethorphan to the subject. Typically, the method comprises applying the transdermal patch described herein to the subject. The transdermal patch can be applied to the subject at a dosing frequency of once daily to once a week, for example, to transdermally deliver a daily dose of about 15 mg to about 50 mg of dextromethorphan to the subject. The disease or disorder is typically a neurological disease or disorder described herein, for example, pseudobulbar affect, depression (e.g., major depressive disorder or treatment resistant depression), stroke, traumatic brain injury, seizure, pain, methotrexate neurotoxicity, Parkinson's disease, autism, or a combination thereof. In some embodiments, the subject is an extensive metabolizer of dextromethorphan. In some embodiments, the subject is a poor metabolizer of dextromethorphan. Suitable dosing regimen, dosing amount, duration, transdermal delivery devices, etc. include any of those described herein in any combination.

In some embodiments, the present disclosure provides a method of treating a disease or disorder described herein in a subject (typically a human subject) in need thereof, the method comprising administering dextromethorphan to the subject according to one or more pharmacokinetic (PK) profile described herein. Typically, the method comprises transdermally delivering a desired daily dose (e.g., about 15 mg to about 50 mg, such as about 35 mg) of dextromethorphan to the subject to achieve the PK profile described herein. For example, in some embodiments, the method comprises applying a transdermal patch to the subject at a dosing frequency of once a day to once a week, to deliver a therapeutically effective plasma concentration of dextromethorphan in the subject at steady state. The transdermal patch can have about 15 mg to about 700 mg dextromethorphan. Typically, the transdermal patch comprises about 30 mg to about 100 mg of dextromethorphan and is applied once a day. The disease or disorder is typically a neurological disease or disorder described herein, for example, pseudobulbar affect, depression (e.g., major depressive disorder or treatment resistant depression), stroke, traumatic brain injury, seizure, pain, methotrexate neurotoxicity, Parkinson's disease, autism, or a combination thereof. Suitable dosing regimen, dosing amount, duration, transdermal delivery devices, etc. include any of those described herein in any combination.

Some embodiments of the present disclosure are directed to methods of administering dextromethorphan to a subject in need thereof. Typically, the method comprises applying the transdermal patch described herein to the subject. The transdermal patch can be applied to the subject at a dosing frequency of once daily to once a week, for example, to transdermally deliver a daily dose of about 15 mg to about 50 mg of dextromethorphan to the subject. The subject typically suffers from a disease or disorder described herein, typically a neurological disease or disorder described herein, for example, pseudobulbar affect, depression (e.g., major depressive disorder or treatment resistant depression), stroke, traumatic brain injury, seizure, pain, methotrexate neurotoxicity, Parkinson's disease, autism, or a combination thereof. In some embodiments, the subject is an extensive metabolizer of dextromethorphan. In some embodiments, the subject is a poor metabolizer of dextromethorphan. Suitable dosing regimen, dosing amount, duration, transdermal delivery devices, etc. include any of those described herein in any combination.

Compared to methods of administering Nuedexta® tablets, the methods herein can be especially advantageous for certain subjects, such as subjects that are sensitive or intolerant to quinidine or in general to CYP2D6 inhibitors. In some embodiments, the subject can be sensitive or intolerant to CYP2D6 inhibitors. In some embodiments, the subject can be sensitive or intolerant to quinidine. In some embodiments, the subject has one or more side effects associated with quinidine. In some embodiments, the subject is co-administered a drug whose metabolism is affected by a CYP2D6 inhibitor. In some embodiments, the subject is co-administered a drug whose metabolism is affected by quinidine. In some embodiments, the subject is co-administered a drug that can affect the pharmacological effect of quinidine.

The methods herein can be used in combination with other medications. In some embodiments, the methods herein can further comprise administering to the subject an active agent other than dextromethorphan. For example, in some embodiments, the method herein comprises administering to the subject an antidepressant. In some embodiments, the method herein further comprises administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof. These additional agents can be administered simultaneously or sequentially in any order, via the same or different route.

In some embodiments, the present disclosure provides:

[1] A method of treating a neurological disease or disorder (e.g., any of those described herein) in a subject in need thereof, the method comprising transdermally delivering a daily dose of about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan to the subject.

[2] The method of [1], wherein the neurological disease or disorder is pseudobulbar affect, depression (e.g., major depressive disorder or treatment resistant depression), stroke, traumatic brain injury, seizure, pain, methotrexate neurotoxicity, Parkinson's disease, autism, or a combination thereof.

[3] The method of [1], wherein the neurological disease or disorder is pseudobulbar affect.

[4] The method of any one of [1]-[3], wherein the daily dose is about 20 mg to 40 mg of dextromethorphan.

[5] The method of any one of [1]-[3], wherein the daily dose is about 35 mg of dextromethorphan.

[6] The method of any one of [1]-[5], comprising applying a transdermal delivery device once daily to transdermally deliver the daily dose to the subject, wherein the transdermal delivery device comprises a drug-in-adhesive layer, wherein the drug-in-adhesive layer comprises dextromethorphan in an amount of about 2% to about 12%, preferably about 6% to about 12% (e.g., about 6%, about 7%, about 8%, about 9%, about 10%, about 11%, about 12%, or any ranges between the recited values, such as about 6-12%, 8-12% etc.) by weight, a pressure sensitive adhesive, and a skin permeation enhancer.

[7] The method of [6], wherein the transdermal delivery device has an active surface area of about 30 $cm^2$ to about 200 $cm^2$, such as about 30 $cm^2$ to about 100 $cm^2$, e.g., about 30 $cm^2$, about 40 $cm^2$, about 50 $cm^2$, about 60 $cm^2$, about 70 $cm^2$, about 80 $cm^2$, about 90 $cm^2$, about 100 $cm^2$, or any ranges between the recited values, such as about 40-60 $cm^2$, about 60-80 $cm^2$, etc.

[8] The method of [6] or [7], wherein the pressure sensitive adhesive is an acrylate adhesive, e.g., a poly acrylate vinyl acetate copolymer, such as those having non-acidic hydroxyl functional groups, for example, described herein such as Duro-Tak 87-2287 adhesive and the alike, which is present in an amount of about 65% to about 85% (e.g., about 65%, about 70%, about 75%, about 80%, or about 85%, by weight, or any ranges between the recited values, such as about 70-85%, about 75-85% etc.) by weight of the drug-in-adhesive layer.

[9] The method of any one of [6]-[8], wherein the skin permeation enhancer is isopropyl myristate, which is present in an amount of about 6% to about 12% (e.g., about 6%, about 7%, about 8%, about 9%, about 10%, about 11%, about 12%, or any ranges between the recited values, such as about 8-12% etc.) by weight of the drug-in-adhesive layer.

[10] The method of any one of [6]-[9], wherein the drug-in-adhesive layer further comprises a crystallization inhibitor, preferably a vinylpyrrolidone polymer, such as vinyl pyrrolidone homopolymer (or povidone), for example, Povidone K30, Plasdone K29/32 and the alike, in an amount of about 6% to about 12% (e.g., about 6%, about 7%, about 8%, about 9%, about 10%, about 11%, about 12%, or any ranges between the recited values, such as about 8-12% etc.) by weight of the drug-in-adhesive layer.

[11] The method of any one of [6]-[10], wherein the drug-in-adhesive layer comprises about 20 mg to about 100 mg of dextromethorphan, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of dextromethorphan.

[12] The method of any one of [6]-[11], wherein the drug-in-adhesive layer comprises about 30 mg to about 100 mg of isopropyl myristate, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of isopropyl myristate.

[13] The method of any one of [6]-[12], wherein the drug-in-adhesive layer comprises about 150 mg to about 900 mg of the pressure sensitive adhesive, e.g., about 300 mg, about 350 mg, about 400 mg, about 450 mg, about 500 mg, about 550 mg, about 600 mg, about 700 mg, about 800 mg, about 900 mg, or any ranges between the recited values, such as about 300-500 mg, 350-450 mg, or about 300-550 mg, etc. of the pressure sensitive adhesive.

[14] The method of any one of [10]-[13], wherein the crystallization inhibitor is present in an amount of about 30 mg to about 100 mg, e.g., in an amount of about 30 mg, about 40 mg, about 50 mg, about 60 mg, about 70 mg, about 80 mg, about 90 mg, about 100 mg, or any ranges between the recited values, such as about 40-60 mg, 50-60 mg, or about 50-70 mg, etc.

[15] The method of any one of [6]-[14], wherein the daily dose is about 35 mg dextromethorphan, and the drug-in-adhesive layer comprises about 50 mg to about 70 mg of dextromethorphan.

[16] The method of any one of [6]-[15], wherein the transdermal delivery device has a total dextromethorphan loading of about 0.2 mg/$cm^2$ to about 5 mg/$cm^2$, such as about 0.2 mg/$cm^2$, about 0.3 mg/$cm^2$, about 0.4 mg/$cm^2$, about 0.5 mg/$cm^2$, about 0.6 mg/$cm^2$, about 0.7 mg/$cm^2$, about 0.8 mg/$cm^2$, about 0.9 mg/$cm^2$, about 1 mg/$cm^2$, about 2 mg/$cm^2$, about 5 mg/$cm^2$, or any ranges between the recited values, such as about 0.2-1 mg/$cm^2$, about 0.5-1 mg/$cm^2$, etc.

[17] The method of any one of [6]-[16], wherein the transdermal delivery device has a dextromethorphan flux of at least about 200 ug/$cm^2$/day, when measured in vitro using human cadaver skin, such as about 200 ug/$cm^2$/day, about 300 ug/$cm^2$/day, about 400 ug/$cm^2$/day, about 500 ug/$cm^2$/day, about 600 ug/$cm^2$/day, about 700 ug/$cm^2$/day, about 800 ug/$cm^2$/day, about 1000 ug/$cm^2$/day, or any ranges between the recited values, such as about 200-800 ug/$cm^2$/day, about 300-800 ug/$cm^2$/day, about 400-800 ug/$cm^2$/day, about 500-800 ug/$cm^2$/day, etc.

[18] A transdermal patch comprises:

i. a backing layer; and ii. a drug-in-adhesive layer comprising 1) dextromethorphan in an amount of about 2% to about 12% by weight; 2) isopropyl myristate in an amount of about 6% to about 12% by weight; 3) a pressure sensitive adhesive, preferably, an acrylate based pressure sensitive adhesive, in an amount of about 65% to about 85% by weight; and optionally 4) a crystallization inhibitor in an amount of about 6% to about 12% by weight, wherein the transdermal patch has an active surface area of about 30 $cm^2$ to about 200 $cm^2$, such as about 30 $cm^2$ to about 100 $cm^2$.

[19] The transdermal patch of [18], wherein the acrylate based pressure sensitive adhesive is an acrylate copolymer adhesive, e.g., a poly acrylate vinyl acetate copolymer pressure sensitive adhesive, such as those having non-acidic hydroxyl functional groups, for example, described herein such as Duro-Tak 87-2287 adhesive and the alike.

[20] The transdermal patch of or [19], wherein the acrylate based pressure sensitive adhesive is in an amount of about 65%, about 70%, about 75%, about 80%, or about 85%, by weight, or any ranges between the recited values, such as about 70-85%, about 75-85% etc.

[21] The transdermal patch of any one of [18]-[20], wherein the crystallization inhibitor is present, which is a vinylpyrrolidone polymer, such as vinyl pyrrolidone homopolymer (or povidone), for example, Povidone K30, Plasdone K29/32 and the alike.

[22] The transdermal patch of any one of [18]-[21], wherein the crystallization inhibitor is present in an amount of about 6%, about 7%, about 8%, about 9%, about 10%, about 11%, or about 12%, or any ranges between the recited values, such as about 6-12% or 8-12% etc.

[23] The transdermal patch of any one of [18]-[22], wherein the isopropyl myristate is in an amount of about 6%, about 7%, about 8%, about 9%, about 10%, about 11%, or about 12%, by weight, or any ranges between the recited values, such as about 8-12% etc.

[24] The transdermal patch of any one of [18]-[23], wherein the dextromethorphan is in an amount of about 6%, about 7%, about 8%, about 9%, about 10%, about 11%, or about 12%, by weight, or any ranges between the recited values, such as about 8-12% etc.

[25] The transdermal patch of any one of [18]-[24], wherein the drug-in-adhesive layer comprises about 20 mg to about 100 mg of dextromethorphan, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of dextromethorphan.

[26] The transdermal patch of any one of [18]-[25], wherein the drug-in-adhesive layer comprises about 30 mg to about 100 mg of isopropyl myristate, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of isopropyl myristate.

[27] The transdermal patch of any one of [18]-[26], wherein the drug-in-adhesive layer comprises about 150 mg to about 900 mg of the pressure sensitive adhesive, preferably acrylate based pressure sensitive adhesive, e.g., about 300 mg, about 350 mg, about 400 mg, about 450 mg, about 500 mg, about 550 mg, about 600 mg, about 700 mg, about 800 mg, about 900 mg, or any ranges between the recited values, such as about 300-500 mg, 350-450 mg, or about 300-550 mg, etc. of the pressure sensitive adhesive.

[28] The transdermal patch of any one of [18]-[27], wherein the drug-in-adhesive layer comprises the crystallization inhibitor in an amount of about 30 mg to about 100 mg, e.g., in an amount of about 30 mg, about 40 mg, about 50 mg, about 60 mg, about 70 mg, about 80 mg, about 90 mg, about 100 mg, or any ranges between the recited values, such as about 40-60 mg, 50-60 mg, or about 50-70 mg, etc.

[29] The transdermal patch of any one of [18]-[28], wherein the drug-in-adhesive layer comprises dextromethorphan as the only active ingredient.

[30] The transdermal patch of any one of [18]-[29], wherein the drug-in-adhesive layer comprises about 56 mg dextromethorphan.

[31] The transdermal patch of any one of [18]-[30], which has an active surface area of about 70 $cm^2$.

[32] The transdermal patch of any one of [18]-[31], which has a total dextromethorphan loading of about 0.2 $mg/cm^2$ to about 5 $mg/cm^2$, such as about 0.2 $mg/cm^2$, about 0.3 $mg/cm^2$, about 0.4 $mg/cm^2$, about 0.5 $mg/cm^2$, about 0.6 $mg/cm^2$, about 0.7 $mg/cm^2$, about 0.8 $mg/cm^2$, about 0.9 $mg/cm^2$, about 1 $mg/cm^2$, about 2 $mg/cm^2$, about 5 $mg/cm^2$, or any ranges between the recited values, such as about 0.2-1 $mg/cm^2$, about 0.5-1 $mg/cm^2$, etc.

[33] The transdermal patch of any one of [18]-[32], which consists of the backing layer, drug-in-adhesive layer, and optionally a release liner.

[34] The transdermal patch of any one of [18]-[33], in the form of a monolithic patch.

[35] The transdermal patch of any one of [18]-[34], which has a dextromethorphan flux of at least about 200 $ug/cm^2/day$, when measured in vitro using human cadaver skin, such as about 200 $ug/cm^2/day$, about 300 $ug/cm^2/day$, about 400 $ug/cm^2/day$, about 500 $ug/cm^2/day$, about 600 $ug/cm^2/day$, about 700 $ug/cm^2/day$, about 800 $ug/cm^2/day$, about 1000 $ug/cm^2/day$, or any ranges between the recited values, such as about 200-800 $ug/cm^2/day$, about 300-800 $ug/cm^2/day$, about 400-800 $ug/cm^2/day$, about 500-800 $ug/cm^2/day$, etc.

[36] A method of treating a neurological disease or disorder (e.g., any of those described herein) in a subject in need thereof, the method comprising applying the transdermal patch of any one of [18]-[35] to the subject.

[37] The method of [36], wherein the applying transdermally delivers a therapeutically effective amount of dextromethorphan to the subject.

[38] The method of [36], wherein the applying transdermally delivers a daily dose of about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan to the subject.

[39] The method of [38], wherein the daily dose is about 35 mg of dextromethorphan.

[40] The method of any one of [36]-[39], wherein the transdermal patch is applied to the subject once daily.

[41] The method of any one of [36]-[40], wherein the neurological disease or disorder is pseudobulbar affect, depression (e.g., major depressive disorder or treatment resistant depression), stroke, traumatic brain injury, seizure, pain, methotrexate neurotoxicity, Parkinson's disease, autism, or a combination thereof,

[42] The method of [41], wherein the neurological disease or disorder is pseudobulbar affect.

[43] A method of treating a neurological disease or disorder (e.g., any of those described herein) in a subject in need thereof, the method comprising applying a transdermal patch to the subject at a dosing frequency of once a day to once a week, wherein the transdermal patch comprises about 15 mg to about 700 mg (e.g., about 15 mg, about 30 mg, about 50 mg, about 75 mg, about 100 mg, about 150 mg, about 200 mg, about 300 mg, about 400 mg, about 500 mg, about 600 mg, about 700 mg, or any ranges between the recited values, such as about 15-100 mg, about 30-100 mg, about 30-75 mg, or about 150-500 mg, etc.) of dextromethorphan, and wherein the applying results in a therapeutically effective plasma concentration of dextromethorphan in the subject at steady state.

[44] The method of [43], wherein the transdermal patch comprises about 30 mg to about 100 mg of dextromethorphan.

[45] The method of or [44], wherein the dosing frequency is once a day.

[46] The method of any one of [43]-[45], wherein the applying results in a pharmacokinetic profile in the subject characterized by an $AUC_{0-24,\ DXM}$ at day-7 or steady state stage between about 180 h*ng/mL to about 2000 h*ng/mL, for example, about 200 h*ng/ml to about 600 h*ng/ml or about 300 h*ng/ml to about 500 h*ng/mL.

[47] The method of any one of [43]-[46], wherein the applying results in a pharmacokinetic profile in the subject characterized by a $C_{Avg,\ DXM}$ at day-7 or steady state stage between about 8 ng/mL to about 100 ng/mL, e.g., about 10 ng/mL to about 20 ng/mL, such as about 15 ng/mL.

[48] The method of any one of [43]-[47], wherein the applying results in a pharmacokinetic profile in the subject characterized by a $C_{min,\ DXM}$ at day-7 or steady state stage between about 6 ng/mL to about 65 ng/mL, e.g., about 6 ng/mL to about 20 ng/mL.

[49] The method of any one of [43]-[48], wherein the applying results in a pharmacokinetic profile in the subject characterized by a $C_{max,\ DXM}$ at day-7 or steady state stage between about 8 ng/mL to about 90 ng/mL, e.g., about 10 ng/ml to about 30 ng/mL.

[50] The method of any one of [43]-[49], wherein the applying results in a pharmacokinetic profile in the subject characterized by a degree of fluctuation $[(C_{max}-C_{min})/C_{avg}]$ for dextromethorphan at day-7 or steady state stage between about 0.18 to about 0.8, e.g., about 0.18 to about 0.8, such as about 0.3 to about 0.5.

[51] The method of any one of [43]-[50], wherein the applying results in a pharmacokinetic profile in the subject characterized by a swing $[(C_{max}-C_{min})/C_{min}]$ for dextromethorphan at day-7 or steady state stage between about 0.2 to about 1.35, e.g., about 0.3 to about 1, such as about 0.4 to 0.7.

[52] The method of any one of [43]-[51], wherein the applying results in a pharmacokinetic profile in the subject characterized by a ratio of $AUC_{0\text{-}24,\ DXM}$ at steady state stage to $AUC_{0\text{-}24,\ DXM,\ D1}$ about 1.5 to about 5, e.g., about 1.5 to about 3, such as about 1.5-2.5.

[53] The method of any one of [43]-[52], wherein the applying results in a pharmacokinetic profile in the subject characterized by a ratio of $AUC_{0\text{-}24,\ DXM}$ to $AUC_{0\text{-}24,\ DOR}$ at steady state stage of about 12 to about 35.

[54] The method of any one of [43]-[53], wherein the applying results in a pharmacokinetic profile in the subject characterized by a ratio of $C_{max,\ DXM}$ to $C_{max,\ DOR}$ at steady state stage of about 12 to about 35.

[55] The method of any one of [43]-[54], wherein the applying results in a pharmacokinetic profile in the subject characterized by a ratio of $C_{Avg,\ DXM}$ to $C_{Avg,\ DOR}$ at steady state stage of about 12 to about 35.

[56] The method of any one of [43]-[55], wherein the applying results in a pharmacokinetic profile in the subject characterized by a) an $AUC_{0\text{-}24,\ DXM}$ at day-7 or steady state stage between about 200 h*ng/mL to about 600 h*ng/ml; b) a $C_{Avg,\ DXM}$ at day-7 or steady state stage about 10 ng/mL to about 20 ng/mL, such as about 15 ng/ml; c) a $C_{min,\ DXM}$ at day-7 or steady state stage between about 6 ng/mL to about 20 ng/mL; and/or d) a $C_{max,\ DXM}$ at day-7 or steady state stage between about 10 ng/ml to about 30 ng/mL.

[57] The method of any one of [43]-[56], wherein the applying results in a pharmacokinetic profile in the subject characterized by e) a degree of fluctuation $[(C_{max}-C_{min})/C_{avg}]$ for dextromethorphan at day-7 or steady state stage between about 0.18 to about 1; and/or f) a swing $[(C_{max}-C_{min})/C_{min}]$ for dextromethorphan at day-7 or steady state stage between about 0.3 to about 1.

[58] The method of any one of [43]-[57], wherein the applying results in a pharmacokinetic profile in the subject characterized by g) a ratio of $AUC_{0\text{-}24,\ DXM}$ at steady state stage to $AUC_{0\text{-}24,\ DXM,\ D1}$ about 1.5 to about 3.

[59] The method of any one of [43]-[58], wherein the applying results in a pharmacokinetic profile in the subject characterized by h) a ratio of $AUC_{0\text{-}24}$, DXM to $AUC_{0\text{-}24,\ DOR}$ at steady state stage of about 12 to about 35; i) a ratio of $C_{max,\ DXM}$ to $C_{max,\ DOR}$ at steady state stage of about 12 to about 35; and/or j) a ratio of $C_{Avg,\ DXM}$ to $C_{Avg,\ DOR}$ at steady state stage of about 12 to about 35.

[60] The method of any one of [43]-[59], wherein the applying results in a pharmacokinetic profile in the subject characterized in that for each application of the transdermal patch other than the first dose, the pre-dosing plasma concentration of dextromethorphan does not go below about 20% of the average concentration ($C_{Avg,\ DXM}$) observed from the immediate previous dose.

[61] The method of any one of [43]-[60], wherein the applying results in a pharmacokinetic profile in the subject characterized in that the accumulation factor of dextromethorphan ranges from about 1 to about 5, e.g., about 1.2 to about 3, wherein the subject is an extensive metabolizer or ultra-extensive metabolizer.

[62] The method of any one of [43]-[61], wherein the applying results in a pharmacokinetic profile in the subject characterized by k) a half-life of dextromethorphan at steady state stage between about 11 to about 29 hours, e.g., about 11 to about 24 hours, such as about 17 hours, in an extensive metabolizer or ultra-extensive metabolizer; and/or l) an Apparent first-order terminal disposition rate constant ($\lambda_z$) following the last dose after achieving steady state stage between about 0.018 $h^{-1}$ to about 0.065 $h^{-1}$, e.g., about 0.020 $h^{-1}$ to about 0.06 $h^{-1}$, in an extensive metabolizer or ultra-extensive metabolizer.

[63] The method of any one of [43]-[62], wherein the applying transdermally delivers a daily dose of about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan to the subject.

[64] The method of any one of [43]-[62], wherein the applying transdermally delivers a daily dose of about 35 mg of dextromethorphan to the subject.

[65] The method of any one of [43]-[64], wherein the neurological disease or disorder is pseudobulbar affect, depression (e.g., major depressive disorder or treatment resistant depression), stroke, traumatic brain injury, seizure, pain, methotrexate neurotoxicity, Parkinson's disease, autism, or a combination thereof.

[66] The method of any one of [43]-[65], wherein the neurological disease or disorder is pseudobulbar affect.

[67] The method of any one of [43]-[66], wherein the transdermal patch is any one of those described herein, such as the transdermal patch of any one of [18]-[35].

[68] The method of any one of [43]-[67], wherein the transdermal patch comprises a backing layer and a drug-in-adhesive layer, wherein the drug-in-adhesive layer comprises dextromethorphan as the only active ingredient, and the drug-in-adhesive layer comprises dextromethorphan in an amount of about 6% to about 12% (e.g., about 6%, about 7%, about 8%, about 9%, about 10%, about 11%, about 12%, or any ranges between the recited values, such as about 8-12% etc.) by weight; isopropyl myristate in an amount of about 6% to about 12% (e.g., about 6%, about 7%, about 8%, about 9%, about 10%, about 11%, about 12%, or any ranges between the recited values, such as about 8-12% etc.) by weight; a pressure sensitive adhesive in an amount of about 65% to about 85% (e.g., about 65%, about 70%, about 75%, about 80%, about 85%, or any ranges between the recited values, such as about 65-85%, about 70-85%, about 75-85% etc.) by weight, and optionally a crystallization inhibitor in an amount of about 6% to about 12% (e.g., about 6%, about 7%, about 8%, about 9%, about 10%, about 11%, about 12%, or any ranges between the recited values, such as about 8-12% etc.) by weight.

[69] The method of [68], wherein the pressure sensitive adhesive is an acrylate based pressure sensitive adhesive, such as an acrylate copolymer adhesive, e.g., a poly acrylate vinyl acetate copolymer pressure sensitive adhesive, such as those having non-acidic hydroxyl functional groups, for example, described herein such as Duro-Tak 87-2287 adhesive and the alike; and the drug-in-adhesive layer comprises the crystallization inhibitor, which is preferably a vinylpyrrolidone polymer, such as vinyl pyrrolidone homopolymer (or povidone), for example, Povidone K30, Plasdone K29/32 and the alike.

[70] The method of or [69], wherein the transdermal patch has a dextromethorphan flux of at least about 200 ug/cm$^2$/day, when measured in vitro using human cadaver skin, such as about 200 ug/cm$^2$/day, about 300 ug/cm$^2$/day, about 400 ug/cm$^2$/day, about 500 ug/cm$^2$/day, about 600 ug/cm$^2$/day, about 700 ug/cm$^2$/day, about 800 ug/cm$^2$/day, about 1000 ug/cm$^2$/day, or any ranges between the recited values, such as about 200-800 ug/cm$^2$/day, about 300-800 ug/cm$^2$/day, about 400-800 ug/cm$^2$/day, about 500-800 ug/cm$^2$/day, etc.

[71] The method of any one of [68]-[70], wherein the transdermal patch comprises about 56 mg of dextromethorphan and has an active surface area of about 70 cm$^2$.

[72] The method of any one of [1]-[17] and [36]-[71] wherein the subject does not suffer from a cough and/or does not need an antitussive.

[73] The method of any one of [1]-[17] and [36]-[72], wherein the subject is characterized as an extensive metabolizer of dextromethorphan.

[74] The method of any one of [1]-[17] and [36]-[72], wherein the subject is characterized as a poor metabolizer of dextromethorphan.

[75] The method of any one of [1]-[17] and [36]-[74], wherein the subject is sensitive or intolerant to CYP2D6 inhibitors.

[76] The method of any one of [1]-[17] and [36]-[75], wherein the subject has one or more side effects associated with quinidine.

[77] The method of any one of [1]-[17] and [36]-[76], wherein the subject is co-administered a drug whose metabolism is affected by a CYP2D6 inhibitor.

[78] The method of any one of [1]-[17] and [36]-[77], further comprising administering to the subject an antidepressant.

[79] The method of any one of [1]-[17] and [36]-[78], wherein the antidepressant is selected from bupropion, hydroxybupropion, erythrohydroxybupropion, threohydroxybupropion, a metabolite or prodrug of any of these compounds, and combinations thereof.

[80] The method of any one of [1]-[17] and [36]-[79], wherein the subject is not administered quinidine.

[81] The method of any one of [1]-[17] and [36]-[80], wherein the subject is a human subject.

[82] The method of any one of [1]-[17] and [36]-[81], wherein the transdermal delivery device or patch is applied once a day, and the residue amount of dextromethorphan in the transdermal delivery device or patch is less than 50% (e.g., less than 40%) of the initial dextromethorphan amount in the transdermal delivery device or patch.

[83] The method of any one of [1]-[17] and [36]-[82], wherein the transdermal delivery device or patch is applied once a day, and the percentage of dextromethorphan delivered to the subject is about 50% to about 80% of the initial dextromethorphan amount in the transdermal delivery device or patch.

BRIEF DESCRIPTION OF THE DRAWINGS/FIGURES

FIG. 1 presents graphs showing in vitro flux study results for transdermal delivery device with Formulations A and B with different adhesives, the flux of dextromethorphan (DXM) from the patch with Formulation A (acrylate adhesive) is shown on the top with a faster flux than the patch with Formulation B (silicone adhesive).

Figure 2:
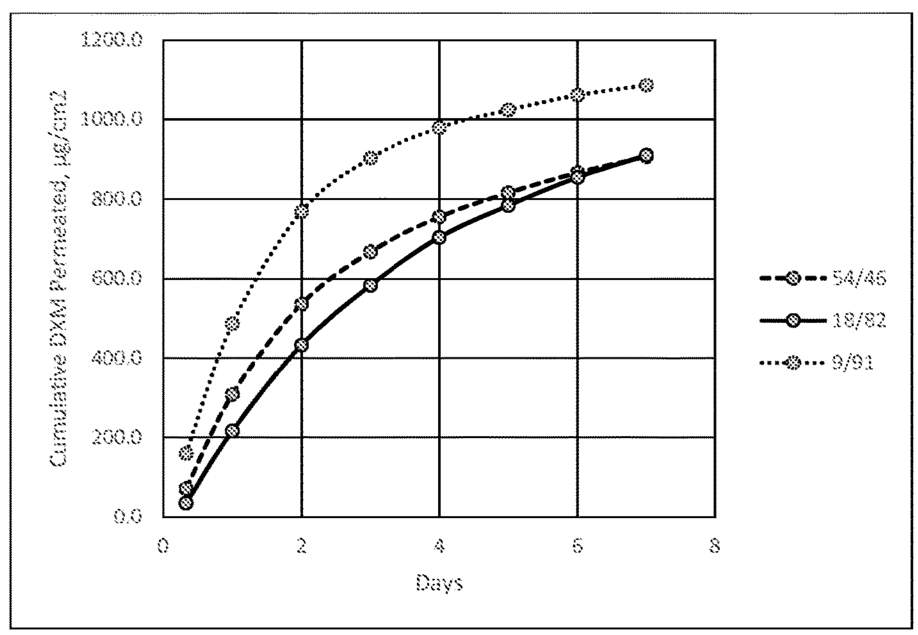

FIG. 2 presents graphs showing in vitro flux study results for patches with Formulations C1-C3, which contains different ratios of silicone adhesive to acrylic adhesive, 54:46 (middle), 18:82 (bottom), and 9:91 (top).

Figures 3A, 3B:
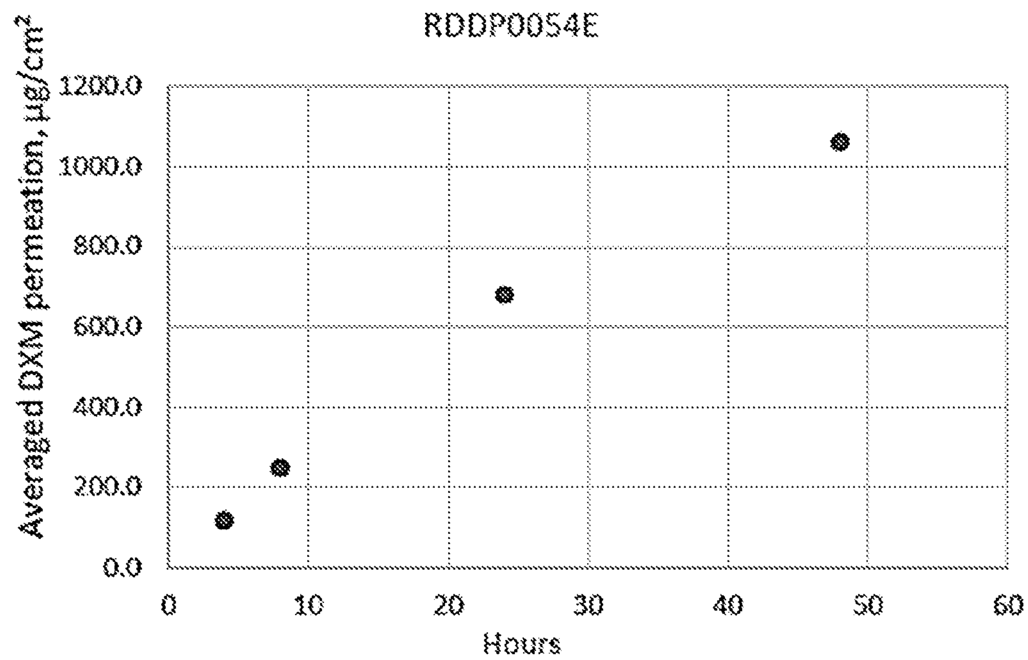

FIG. 3A presents graphs showing effects of a skin permeation enhancer (isopropyl myristate, IPM) on in vitro flux: 10% IPM (top), 7.7% IPM (middle), and 0% IPM (bottom).

FIG. 3B presents graphs showing average dextromethorphan permeated vs time profile of a patch with Formulation E1.

Figure 4A:
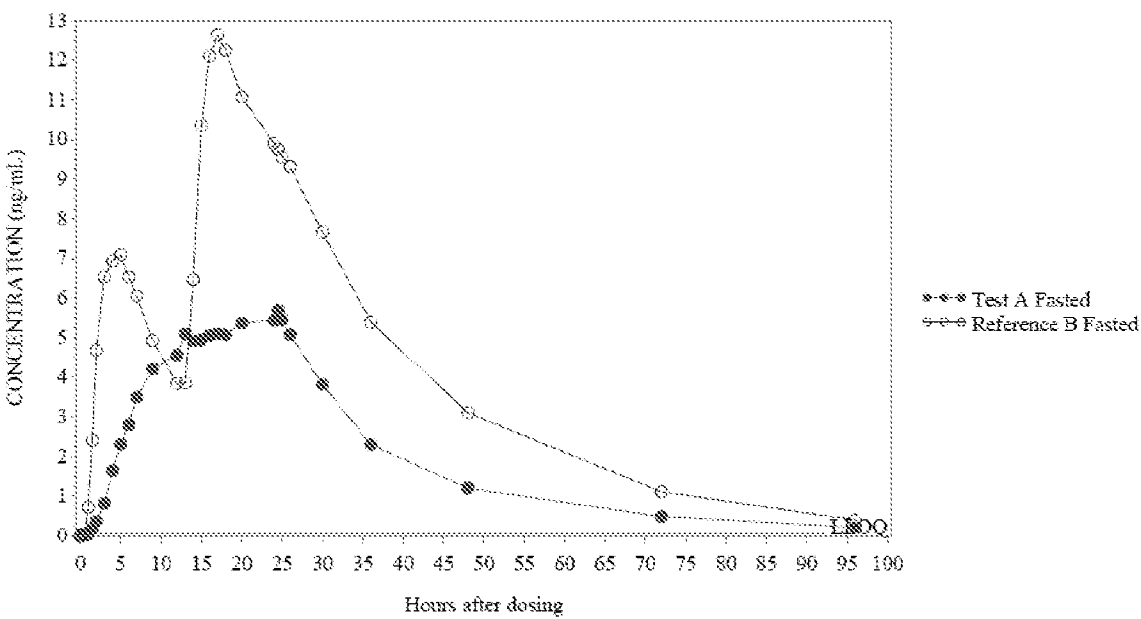
Figure 4B:
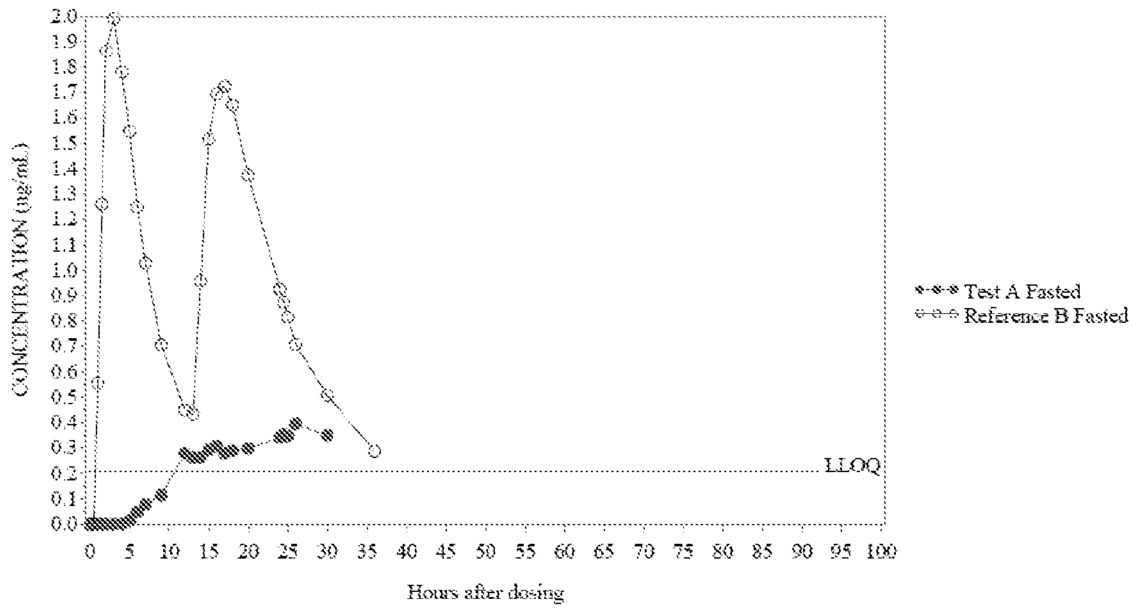

FIG. 4A shows dextromethorphan plasma concentration over the course of 96 hours for a human clinical study comparing the effect of administration of DXM transdermal patch (test A) for 24 hours and oral administration of Nuedexta (20 mg DXM/10 mg quinidine) (Reference B) twice a day. FIG. 4B shows the metabolite, dextrorphan's (DOR) plasma concentration over the course of 96 hours for the same study. For FIGS. 4A and 4B, both test and reference administration were to subject under fasted condition. The plasma concentrations refer to mean plasma concentrations, with N=16.

Figure 5:
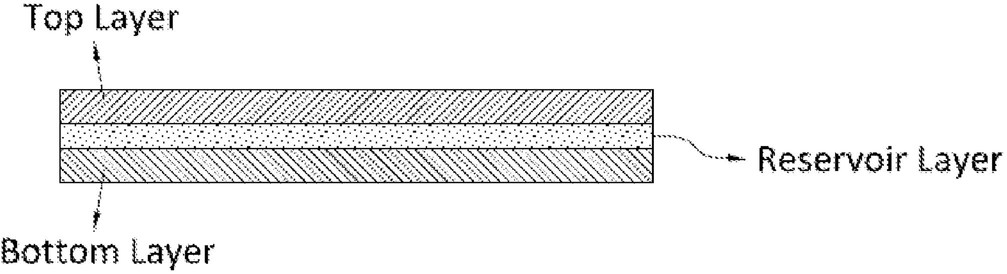

FIG. 5 shows a multilayer patch design. The top layer is a skin-contacting adhesive layer, the middle layer is a reservoir layer, and the bottom layer is a backing layer or an adhesive layer, which can be the same or different from the top layer.

Figure 6A:
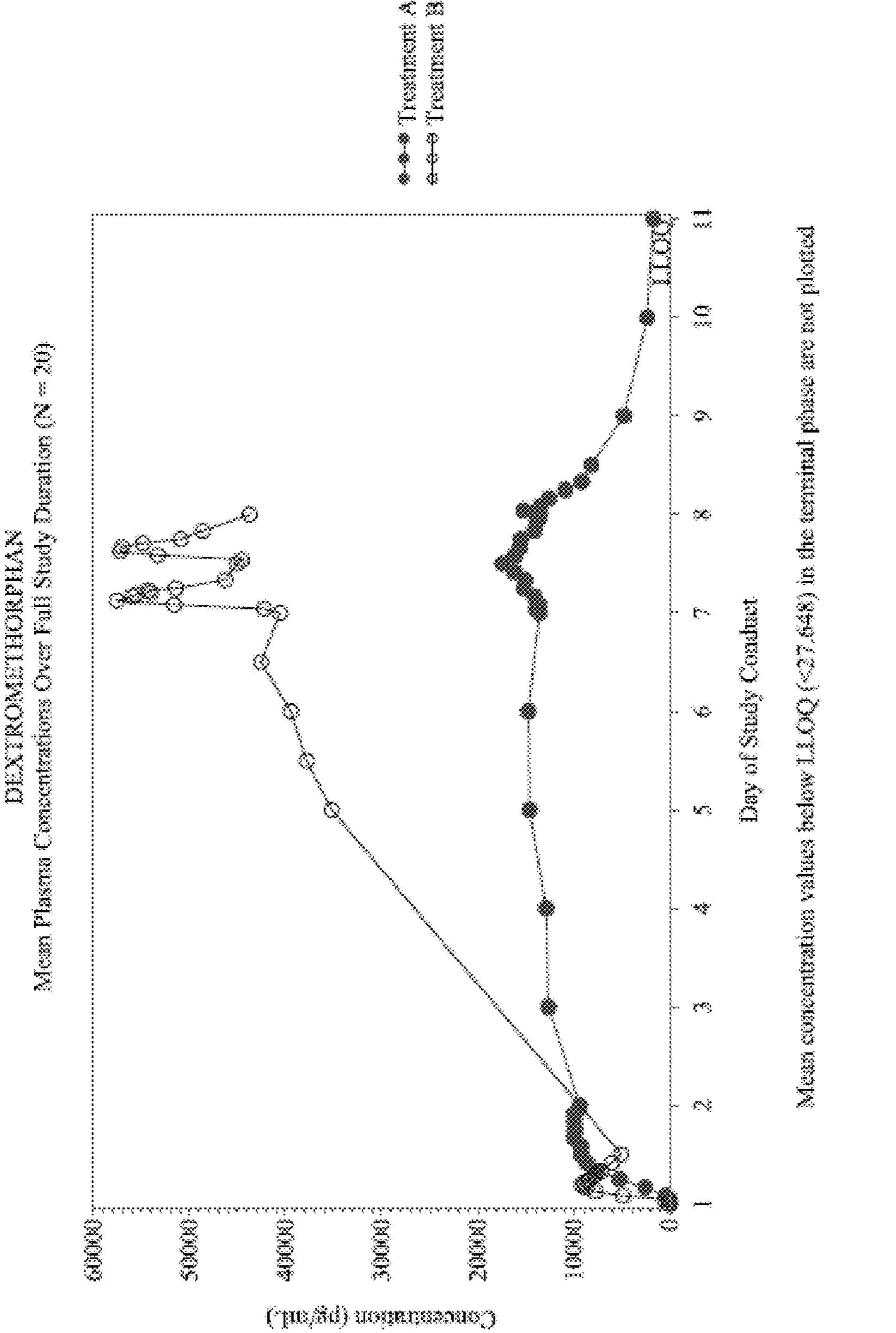
Figure 6B:
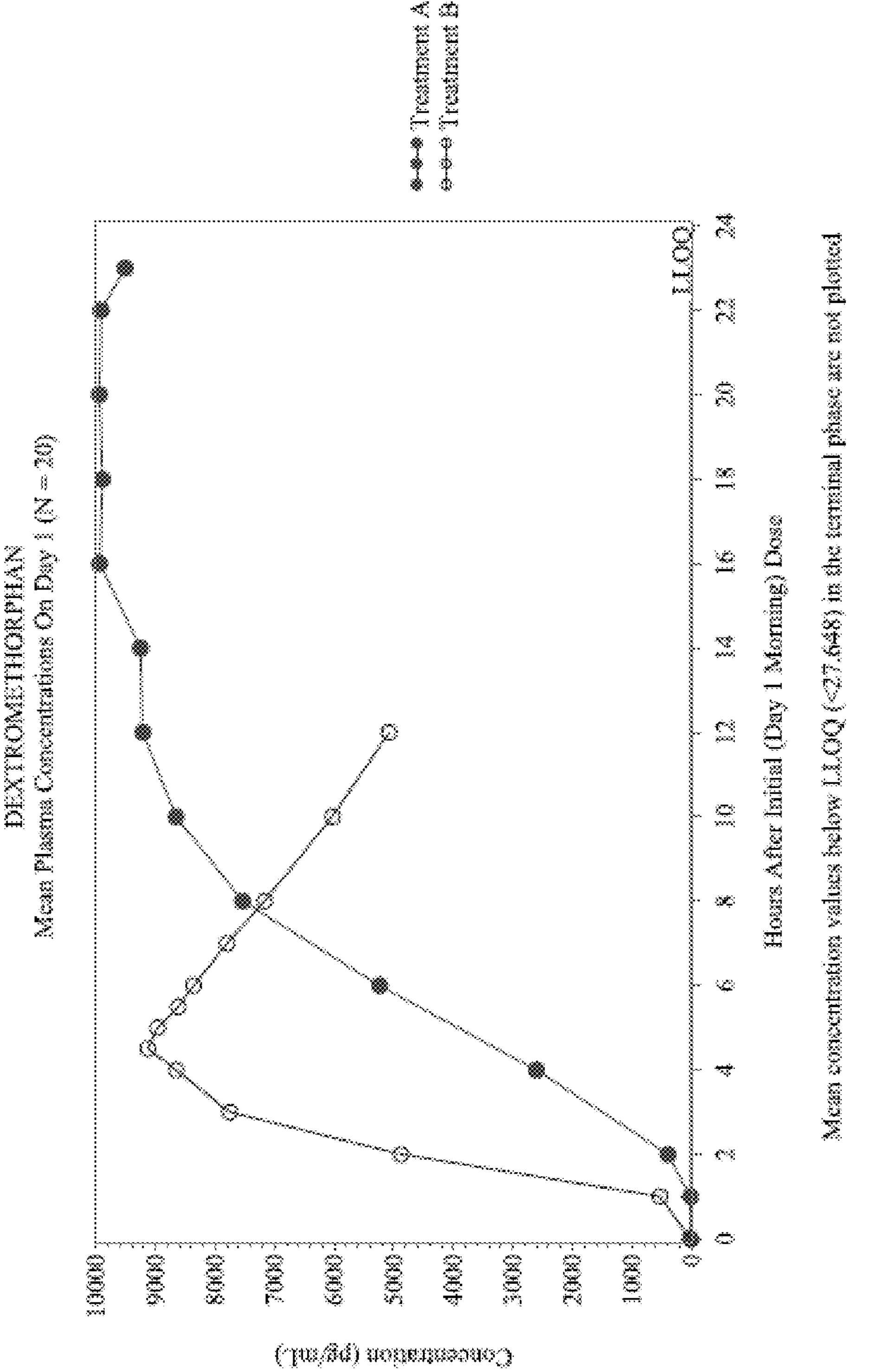
Figure 6C:
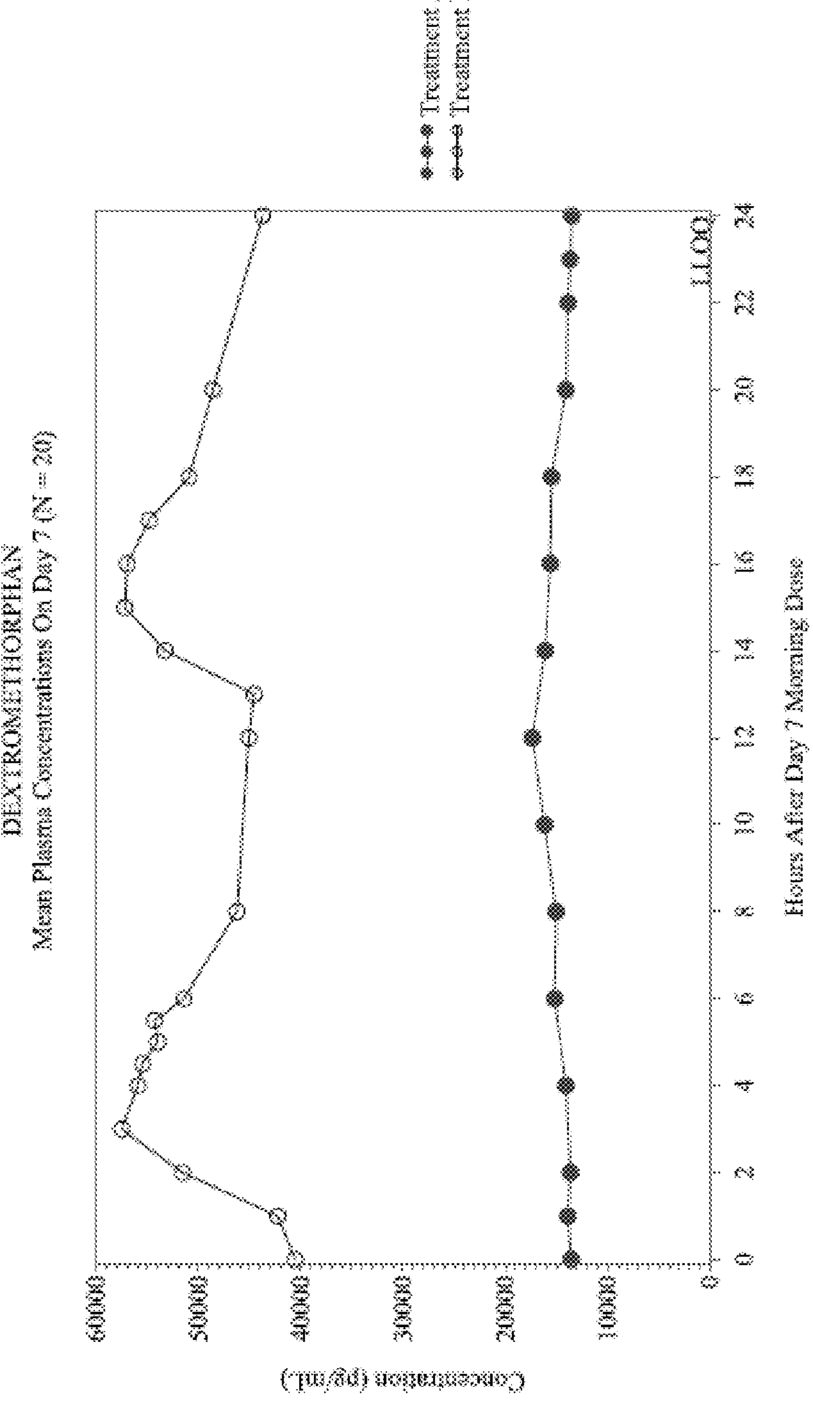
Figure 6D:
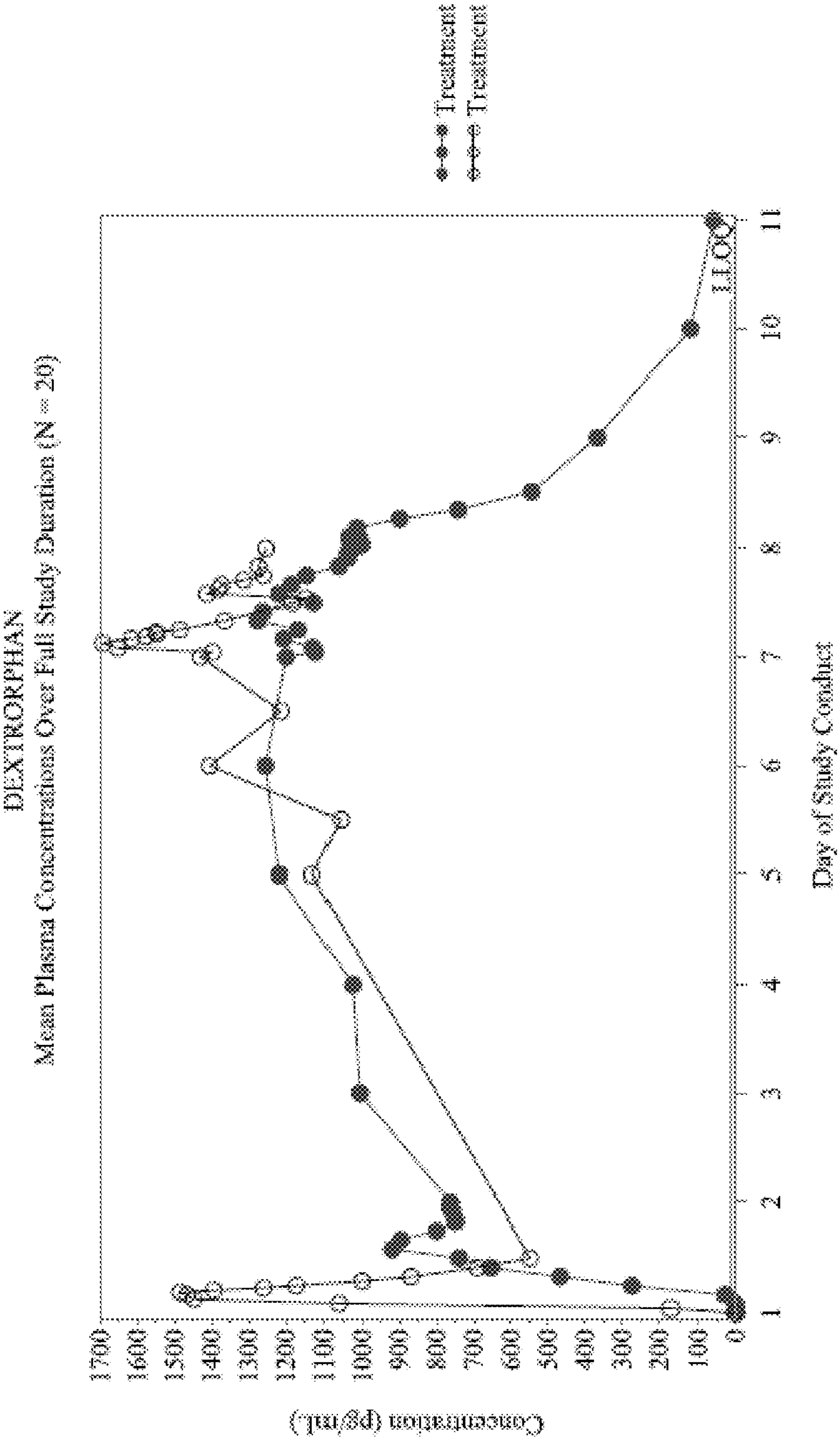
Figure 6E:
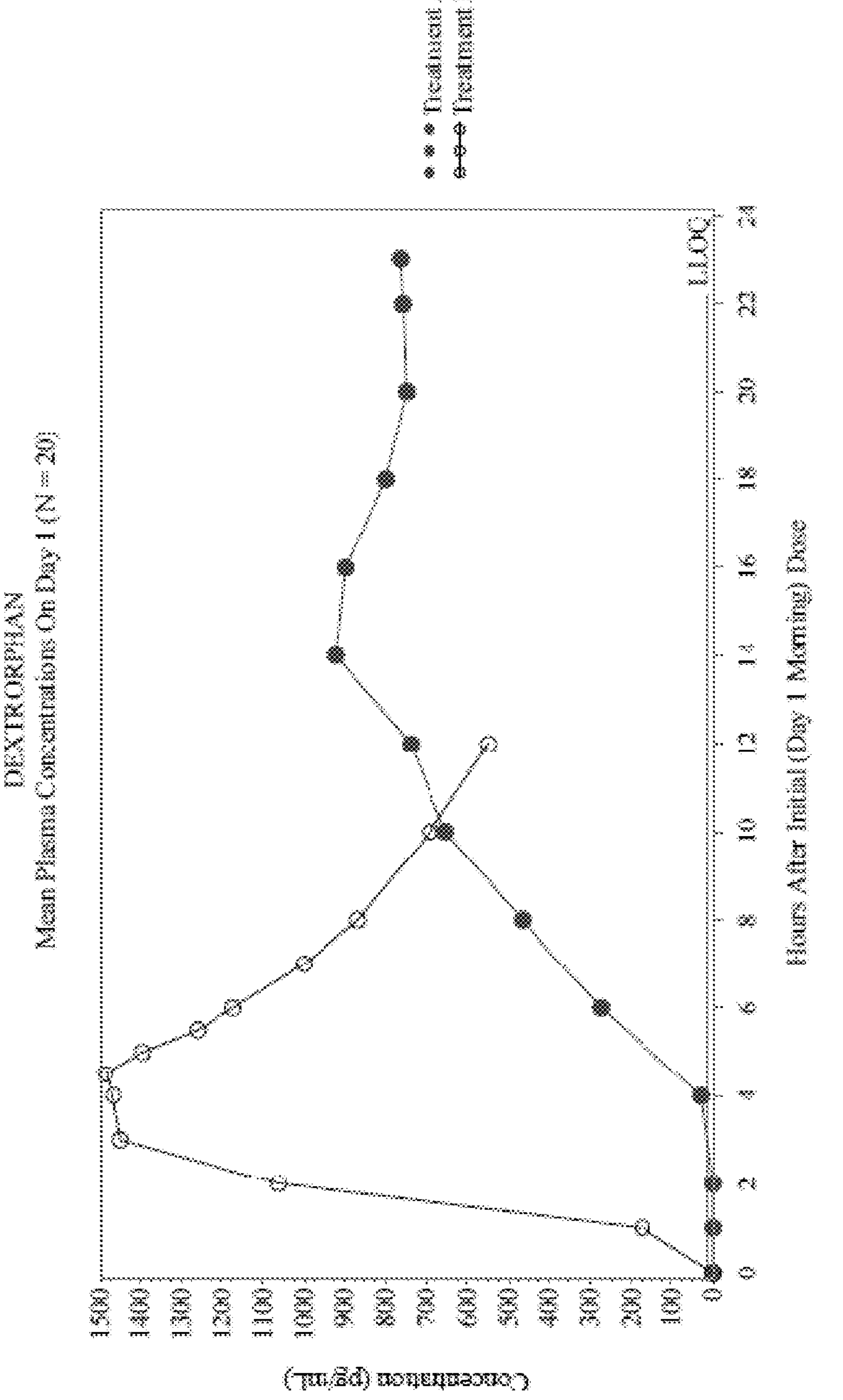
Figure 6F:
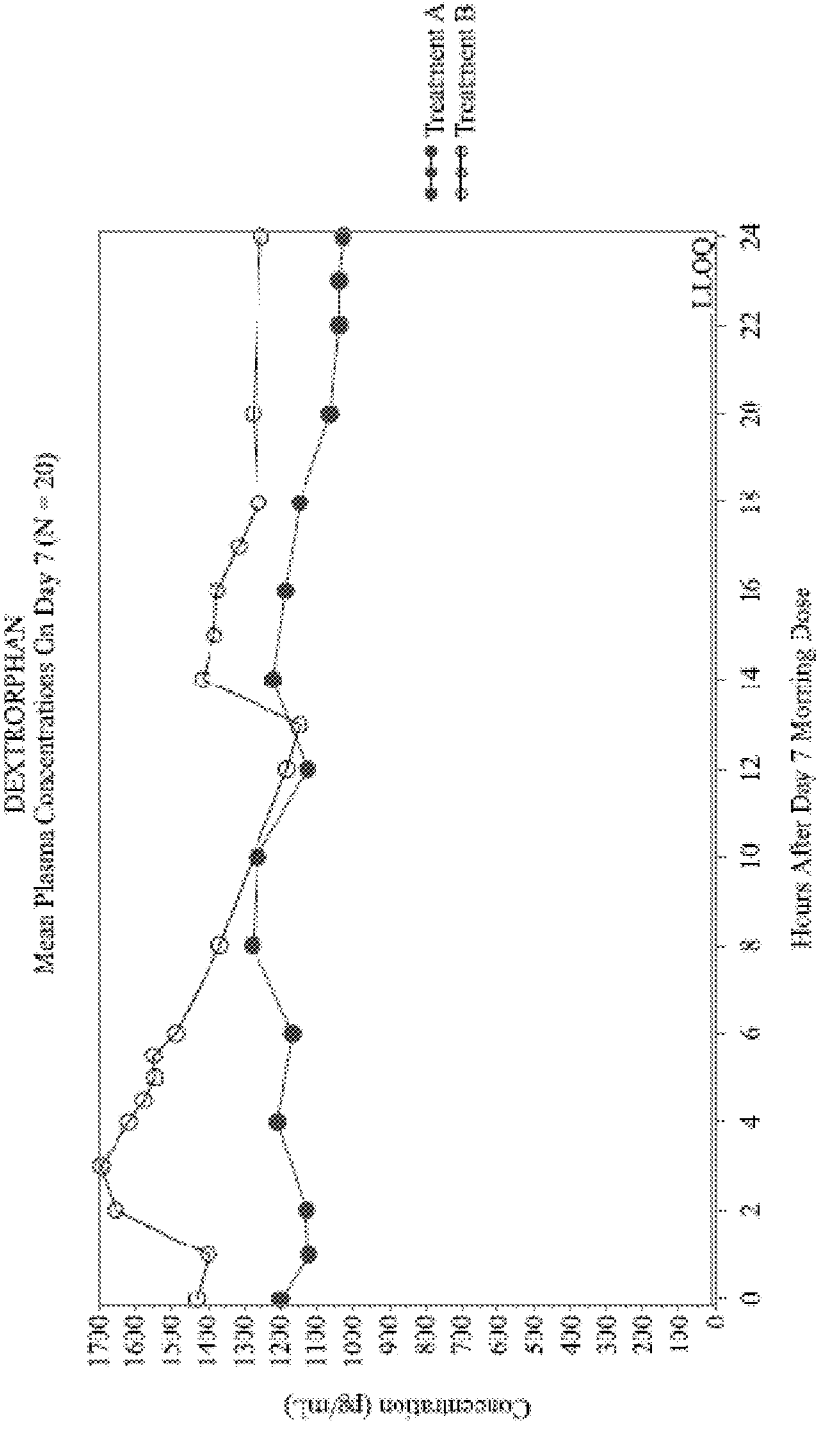

FIG. 6A shows mean dextromethorphan plasma concentration over the course of 11 days for a human clinical study comparing the effect of administration of a DXM transdermal patch (Treatment A) every 24 hours for 7 days and oral administration of Nuedexta® (20 mg DXM/10 mg quinidine) (Treatment B) twice a day for 7 days, N is 20 in this study. FIG. 6B shows mean dextromethorphan plasma concentration vs time profile on day 1 following Treatment A or B of the same trial. FIG. 6C shows mean dextromethorphan plasma concentration vs time profile on day 7 following Treatment A or B of the same trial. FIG. 6D shows mean dextrorphan plasma concentration over the course of 11 days for a human clinical study following Treatment A or B of the same trial. FIG. 6E shows mean dextrorphan plasma concentration vs time profile on day 1 following Treatment A or B of the same trial. FIG. 6F shows mean dextrorphan plasma concentration vs time profile on day 7 following Treatment A or B of the same trial.

DETAILED DESCRIPTION

Dextromethorphan (DXM) has been used orally to treat neurological disorders such as pseudobulbar affect (PBA), emotional lability, agitation in Alzheimer's, major depressive disorder, treatment resistant disorder, pain management, other CNS disorders, and the like. But, to be effective, it must be delivered with a substance that competitively inhibits the liver enzyme cytochrome P450 2D6 (CYP2D6). It particular, this has meant it is co-administered with quinidine. Otherwise, too little makes it pass the liver's diligence of digested food.

The present disclosure generally relates to transdermal delivery of dextromethorphan using the transdermal delivery devices, formulations (e.g., adhesive compositions), and methods herein, which provides many advantages over the currently available oral formulations (e.g., Nuedexta®) and solves many unmet medical needs of such oral formulations. For example, the transdermal delivery devices or formulations herein can be administered to achieve a therapeutically effective plasma concentration without regard to whether a CYP2D6 inhibitor such as quinidine is co-administered. As such, the transdermal delivery devices or formulations herein can be administered to transdermally deliver dextromethorphan to subjects who are for example, sensitive or intolerant to CYP2D6 inhibitors such as quinidine (e.g., having one or more side effects associated with quinidine, or is co-administered a drug whose metabolism is affected by CYP2D6 inhibitors such as quinidine). Further, the transdermal delivery devices or formulations herein can be conveniently administered to transdermally deliver dextromethorphan to a subject with or without first determining whether the subject is a poor metabolizer, an intermediate metabolizer, or an extensive metabolizer of dextromethorphan. For brevity, as used herein, unless otherwise obvious from context, poor metabolizer (PM), intermediate metabolizer (IM), or extensive metabolizer (EM) refers to the subject's ability to metabolize dextromethorphan. Categorization of a subject as a PM, IM, or EM (alternatively labeled as ultrametabolizers or ultrarapid metabolizers or UM) is known in the art. See e.g., Treducu A. L. D. et al. *Frontiers in Pharmacology*, vol. 9, Article 305 (April 2018), which based on genotype assigned subjects as UM if containing "≥3 normal function gene copies").

Administering dextromethorphan using the transdermal delivery devices or formulations herein can also provide superior clinical experience compared to Nuedexta®, for example, with more accurate dosing, less frequent dosing, reduced potential for side effects associated with quinidine and/or higher exposure (e.g., $C_{max}$) of dextromethorphan, reduced pill burden, and better patient compliance. In view of this disclosure, those skilled in the art could select a proper patch to more precisely deliver a therapeutically effective amount of dextromethorphan to the subject treated. Additionally, the steady state PK profile described herein shows that transdermal delivery of dextromethorphan can achieve a much lower but effective amount of dextromethorphan plasma exposure compared to a twice-a-day oral dosing of Nuedexta® tablets. Thus, it is expected that the methods herein would at least produce a reduced incidence of side effects associated with high exposure (e.g., $C_{max}$, AUC, etc.) of dextromethorphan. The transdermal delivery devices herein can be configured as a 1-day patch, 2-day patch, 3-day patch, 4-day patch, 5-day patch, 6-day patch, or 7-day patch, which is suitable for dosing frequencies ranging from once a day to once a week, for example, once in more than 24 hours, more than 36 hours, more than 48 hours, etc., or 1, 2, 3, 4, 5, or 6 times a week. Using the transdermal delivery devices herein can provide improved patient compliance, at least by avoiding the twice-a-day dosing regimen of Nuedexta®.

Prior to Applicant's work, it was not known whether dextromethorphan can be delivered transdermally to achieve a therapeutically effective plasma concentration for treating a neurological disease or disorder such as PBA. The unpredictability of transdermal administration is notorious. For example, testosterone can be delivered transdermally without enhancer at a rate three orders of magnitude higher than for beta estradiol. Structurally and by calculated Log P, these compounds are very similar, such that this difference could not be anticipated. See, U.S. Provisional Appl. No. 62/568,028, filed Oct. 4, 2017, the content of which is incorporated by reference in its entirety. U.S. Pat. No. 6,335,030 B1 describes some examples of dextromethorphan patches with a goal to achieve an antitussive effect. However, no pharmacokinetic data on transdermal administration of dextromethorphan was known before Applicant's work described in U.S. Provisional Application 62/680,182 and International Application No. PCT/US2018/054178, published as WO2019/070864, the content of each of which is incorporated by reference in its entirety.

In PCT/US2018/054178, it was shown that transdermal delivery of dextromethorphan, without using quinidine, can provide a significant blood level of dextromethorphan in human. PCT/US2018/054178 describes a human pharmacokinetic study showing that applying to healthy human an exemplary patch containing about 35 mg dextromethorphan with a size of 45 $cm^2$, which was designed to transdermally deliver 15 mg per day and contains, in the adhesive layer (drug-in-adhesive layer) about 80% by weight of an adhesive (Duro-Tak 87-2287), about 10% by weight of dextromethorphan base and about 10% by weight of permeation enhancer isopropyl myristate, for about 24 hours, achieved, inter alia, a mean $C_{max}$ of about 6 ng/ml and a mean $AUC_{0-24\ h}$ of about 92 h·ng/ml, approaching those observed from orally administering Nuedexta® tablets (a combination of 20 mg dextromethorphan and 10 mg quinidine) twice a day to the human subject.

Further developments, as detailed herein, show that the inclusion of a crystallization inhibitor, a vinylpyrrolidone polymer (Plasdone K29/32) in dextromethorphan transdermal patches significantly enhanced the permeation of dextromethorphan from the patches, in vitro and in vivo. In the Examples section, it was shown that a 70 $cm^2$ patch applied for 24 hours can deliver a daily dose of about 32.4 mg to about 41.1 mg of dextromethorphan to human subjects, which therefore has a flux of dextromethorphan of about 0.46 $mg/cm^2/day$ to about 0.59 $mg/cm^2/day$. This represents a significantly higher flux compared to a similar patch, except without the vinylpyrrolidone polymer (replaced with the adhesive matrix Duro-Tak 87-2287), which has an estimated flux of about 0.33 $mg/cm^2/day$. Additional in vivo data also indicates that the per unit patch area ($cm^2$) delivery of dextromethorphan is enhanced with patches having the vinylpyrrolidone polymer. For example, as shown in Example 4, the $C_{max}$ or $AUC_{0-24}$ at day 1, normalized with the patch area, with patches having the vinylpyrrolidone polymer is about 20% higher than those observed with the patches without the vinylpyrrolidone polymer. This enhanced flux does not require a higher dextromethorphan loading per $cm^2$. In fact, the dextromethorphan loading of the patches are not different, both at about 0.8 $mg/cm^2$.

In addition, it was found that the required amount of dextromethorphan for the transdermal patches herein to achieve the desired daily dose does not exceed twice the amount of the desired daily dose. For example, the Examples show that it was possible to deliver a desired daily dose of about 35 mg with a transdermal patch having less than 70 mg of dextromethorphan (about 56 mg dextromethorphan). Thus, the transdermal bioavailability (i.e., the delivered dextromethorphan divided by initial dextromethorphan in the patch) is generally higher than 50%, up to 80% or higher. This high bioavailability is made possible in part due to the unexpected discovery that it is possible to achieve continuously high flux of dextromethorphan for the transdermal patches herein. In light of these results, using the patches herein can be further advantageous, which include for example, with a smaller-sized patch to deliver similar amount of dextromethorphan, have smaller amount of residue dextromethorphan in worn patches, etc.

In various embodiments, the present disclosure provides transdermal delivery devices and formulations comprising dextromethorphan, methods of preparing the same, methods of delivering dextromethorphan transdermally using the transdermal delivery devices or formulations herein, and methods of treating a disease or disorder using the transdermal delivery devices or formulations herein.

Transdermal Delivery Device Comprising Dextromethorphan

Certain embodiments of the present disclosure are directed to novel transdermal delivery devices comprising dextromethorphan.

Various patch designs can be used for the transdermal delivery device herein. The transdermal delivery device herein typically comprises a backing layer, an adhesive layer (e.g., a drug-in-adhesive layer), which is the skin-contacting layer when in use, and optionally a reservoir layer. The adhesive layer typically comprises dextromethorphan dispersed (e.g., homogenously dispersed, which also includes dissolved) in an adhesive, preferably a pressure sensitive adhesive. More than one adhesive layers can be used for the transdermal delivery device herein. The adhesive layer is typically formulated such that the transdermal delivery device can adhere to the skin of a user for a desired period of time. For example, in some embodiments, the transdermal delivery device is capable of adhering continuously to the skin of a user for about 8 hours, about 12 hours, about 18 hours, about 24 hours, about 2 days, about 3 days, about 4 days, about 5 days, about 6 days, or about 7 days or more.

In some embodiments, the transdermal delivery device can be a drug-in-adhesive (DIA) patch. In some embodiments, the DIA patch is a single layer patch, for example, the single layer includes dextromethorphan homogenously dispersed in the adhesive. In some embodiments, the DIA patch is a multilayer patch. For example, two drug-in-adhesive layers can be included in the patch, which is optionally separated by a membrane, e.g., a rate-controlling membrane, or by a reservoir layer. In some embodiments, one of the drug-in-adhesive layer can be a reservoir layer, for example, with a higher dextromethorphan concentration than the other layer. In some embodiments, the two drug-in-adhesive layers can sandwich a reservoir layer.

A drug-in-reservoir (DIR) design can also be used for the transdermal delivery device herein. In some embodiments, the reservoir layer and the adhesive layer can be laminated to each other or separated, for example, by a rate-controlling membrane. For example, in some embodiments, the reservoir layer, such as a drug matrix, can be laminated with the adhesive layer. Those skilled in the art would understand that such adhesive layer can also contain certain amount of drug, for example, through equilibrium.

Other patch designs can also be used for the transdermal delivery device herein. For example, in some embodiments, the transdermal delivery device can be an active patch, such as an iontophoresis patch. In some embodiments, the transdermal delivery device can be a minimally invasive patch, such as a microneedle based patch.

The transdermal delivery device can include dextromethorphan as the only drug or in combination with another drug. Unless obviously contradictory, in any of the embodiments described herein, dextromethorphan can be the only drug in the transdermal delivery device. Dextromethorphan can exist in various forms, for example, as a free base or a pharmaceutically acceptable salt. As used herein, the weight percentage, concentration, flux, etc. regarding dextromethorphan should be understood as the total amount of dextromethorphan measured and/or calculated, with the value expressed in the equivalent value for dextromethorphan base. Further, all weight percentages, unless otherwise obvious from context, should refer to the weight percentage based on the final formulation (e.g., final adhesive layer or reservoir layer etc.) or transdermal delivery device as appropriate. In any of the embodiments described herein, the dextromethorphan can exist in its free base form, except that it can be protonated through equilibrium with other ingredient(s). For example, in any of the embodiments described herein, the transdermal delivery device or pharmaceutical compositions described herein can be prepared by mixing directly or indirectly the recited amount of dextromethorphan base with the other ingredients.

In any of the embodiments described herein, the dextromethorphan in the transdermal delivery device can be partially or completely replaced with a deuterated dextromethorphan, e.g., the d3 analog ($O—CD_3$, or $N—CD_3$) or d6 analog ($N—CD_3$,$O—CD_3$) see, e.g., claims 1 and 17 of U.S. Pat. No. 7,973,049, the content of which is incorporated by reference in its entirety. Apparently, in such embodiments, the methods using the deuterated dextromethorphan patches would provide deuterated dextromethorphan to the user. As used herein, a deuterated dextromethorphan refers to a compound resulted from substituting one or more hydrogen atoms of dextromethorphan with deuterium such that each substituted position has a deuterium content above the natural abundance, i.e., the substituted position is enriched with deuterium. In some embodiments, the deuterated dextromethorphan has at least one position with deuterium enriched to at least 10% deuterium, at least 50% deuterium, at least 90% deuterium, at least 95% deuterium or at least 98% deuterium. In any of the embodiments described herein, the dextromethorphan in the transdermal delivery device can also be partially or completely replaced with a dextromethorphan analog, such as a fluorinated dextromethorphan or a skin permeable prodrug of dextromethorphan, etc.

The adhesive layer typically includes a pressure sensitive adhesive (PSA). Useful features for pressure sensitive adhesive include adequate tack, good adhesion and cohesive strength. Further useful attributes include biocompatibility (e.g., non-irritating, non-sensitizing non-toxic), formulation compatibility, delivery system compatibility and the like. Useful pressure sensitive adhesive include for example polyacrylates, poly acrylic esters, silicones, polyisobutylenes and the like.

PSAs are generally known in the art. See, e.g., Tan et al., Pharm Sci & Tech Today, 2:60-69 (1999). Non-limiting useful PSAs include polyisobutylenes (PIB), silicone polymers, acrylate copolymers, and combinations thereof. In some embodiments, the pressure sensitive adhesive comprises a polyisobutylene adhesive, a silicone polymer adhesive, an acrylate copolymer adhesive, or a combination thereof. In some embodiments, the pressure sensitive adhesive comprises an acrylate copolymer adhesive. Non-limiting useful acrylate copolymers include, for example, acrylic pressure sensitive adhesives such as a poly acrylate vinyl acetate copolymer, e.g., Duro-Tak 87-2287, Duro-Tak 87-4098, Duro-Tak 87-4287, or Duro-Tak 87-2516, Duro-Tak 87-2852 or Duro-Tak 87-2194, which are manufactured by Henkel Adhesives. PIBs are elastomeric polymers that are commonly used in PSAs, both as primary-base polymers and as tackifiers. PIBs are homopolymers of isobutylene and feature a regular structure of a carbon-hydrogen backbone with only terminal unsaturation. Non-limiting useful PIBs include those marketed under the trade name Oppanol by BASF. The silicone polymers are a high molecular weight polydimethylsiloxane that contains residual silanol functionality (SiOH) on the ends of the polymer chains. Non-limiting useful silicone PSAs for use in pharmaceutical applications include those available from Dow Corning Corporation, for example under the trade name of BIO-PSA, e.g., BIO-7-4202. In some embodiments, the adhesive layer is about 0.1 mils to about 10 mils, e.g., about 1.5 mils to about 10 mils (e.g., about 1.5 mils to about 2 mils) thick.

In some embodiments, suitable adhesives include for example the following silicone adhesives from Dow Corning: BIO-PSA 7-410X, BIO-PSA 7-420X, BIO-PSA 7-430X, BIO-PSA 7-440X, BIO-PSA 7-450X, BIO-PSA 7-460X, and BIO-PSA Hot Melt Adhesive. In some embodiments, suitable adhesives include for example the following polyacrylate/poly acrylic ester adhesives from Henkel Adhesives: Duro-Tak 87-900A, 87-9301, 87-4098, 87-2510, 87-2287, 87-2677, 87-4287, 87-2516, 87-2074, 87-235A, 87-2353, 87-2852, 87-2051, 87-2052, 87-2054, 87-2194, 87-2196, 87-6908, 387-2510, 387-2287, 387-2516, 387-2353, 387-2051, 387-2051 and 387-2054, GELVA GMS 3083, 3253, 788 and 9073. These can for example have hydroxy functional groups, carboxylic groups, hydroxy and carboxylic groups, or no functional groups (as active as the foregoing). These can for example include vinyl acetate monomer, or not. In some embodiments, the pressure sensitive adhesive can be copolymers formed from acrylate monomers and vinyl acetate, including those containing non-acidic hydroxyl functional groups, such as DuroTak® 2287 (87-2287, 387-2287, etc.) adhesives and the alike. A typical composition of DuroTak® 2287 can include random copolymers formed from the following monomers: 2-ethylhexylacrylate (e.g., about 68.2%), vinyl acetate (e.g., about 26.5%), hydroxyethylacrylate (e.g., about 5.2%), and glycidylmethacrylate (e.g., about 0.15%). In some embodiments, the acrylate copolymer adhesive can be formed from monomers including about 5.2 wt % 2-hydroxyethyl acrylate, about 20-40 wt % vinyl acetate, and about 55-75 wt % 2-ethylhexyl acrylate. See also U.S. Published Application No. US20060257462A1 and U.S. Pat. No. 5,693,335, the content of each of which is herein incorporated by reference in its entirety.

Typically, the transdermal delivery device (e.g., a DIA patch) is supported by a backing layer such as an impermeable backing film, and the adhesive surface is protected by a release liner prior to use. Various materials can be used as a backing layer for the transdermal delivery device herein. Typically, the backing layer is impermeable. For example, the backing layer can be comprised of impermeable polymeric films such as polyester (PET) or polyethylene (PE) films. In some embodiments, the backing layer can comprise a polyester, such as Scotchpak 9736 or Scotchpak 1012, a polyurethane film, such as Scotchpak 9701, or a polyethylene film, such as CoTran 9720. In some embodiments, the backing is part of an overlay, and can be a non-woven fabric, a polyurethane film, or other pliable material to provide flexibility and better wear.

The release liner can be manufactured in the desired size for the present invention. The release liner can be comprised of silicone or fluoro-polymer coated polyester film. The release liner protects the transdermal delivery device during storage and is removed before its use. Silicone-coated release liners include those manufactured by Mylan Corporation, Loparex Corporation, and 3M's Drug Delivery Systems. The fluoro-polymer coated release liners include those manufactured and supplied by 3M's Drug Delivery Systems and Loparex. In some embodiments, the release liner comprises 3M's ScotchPak 9744 or Scotchpak 1022.

The transdermal delivery devices herein can also optionally include other suitable excipients such as humectants, plasticizers, antioxidants, anti-irritants, gel-forming agents, crystallization inhibitors, drug release modifiers etc. These excipients are within the knowledge of those skilled in the art, and can be found, for example, in the Handbook of Pharmaceutical Excipients, (7th ed. 2012), the entire content of which is hereby incorporated by reference. In some embodiments, additional active ingredient(s) can also be included in the transdermal delivery device herein.

The transdermal delivery devices (e.g., DIA patches) herein can have different sizes (patch sizes) depending on its application. Typically, the patch sizes can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 80 $cm^2$, about 100 $cm^2$, about 120 $cm^2$, about 150 $cm^2$, about 200 $cm^2$ or any ranges between the specified values), for example, about 10 $cm^2$ to about 100 $cm^2$.

When applying the transdermal delivery devices (e.g., DIA patches) herein to a skin of a subject, all of the adhesive surface can become in contact with the skin in theory. Thus, the area of the adhesive surface defines a skin contact area where the active ingredient from the device can permeate the skin, which is also herein referred to as an active surface area. In some embodiments, the adhesive surface is the only surface of the transdermal delivery device that is in contact with the skin upon application, and the active surface area is the same as the area of the adhesive surface. In some embodiments, the adhesive surface and one or more other surfaces of the transdermal delivery device are in contact with the skin upon application, and the entire skin contact area is the active surface area. In a typical DIA patch, the patch size is the same as the active surface area. Unless otherwise obvious from context, the unit "/$cm^2$" should be understood as per square centimeter of active surface area as defined herein.

The active surface area can determine the doses of the drug to be delivered. Typically, the active surface area can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 80 $cm^2$, about 100 $cm^2$, about 120 $cm^2$, about 150 $cm^2$, about 200 $cm^2$ or any ranges between the specified values), for example, about 10 $cm^2$ to about 100 $cm^2$.

In some embodiments, the transdermal delivery device herein can be configured to provide dextromethorphan to a user (e.g., human subject) at least about 2 mg/day (e.g., about 2 mg/day to about 50 mg/day) for a period of time of 1 day or more, for example, 2 days, 3 days, 4 days, 5 days, 6 days, or 7 days. For example, in some embodiments, the transdermal delivery device is configured to transdermally deliver dextromethorphan to a user about 5 mg/day to about 50 mg/day (e.g., about 5 mg/day, about 10 mg/day, about 20 mg/day, about 30 mg/day, about 40 mg/day, about 50 mg/day, or any ranges between the recited values) for 1 day or more (e.g., 1.5 days, 2 days, 3 days, 4 days, 5 days, 6 days, 7 days, or any ranges between the recited values).

The total dextromethorphan loading for the transdermal delivery device can be adjusted based on the desired total dose. Typically, the total dextromethorphan loading exceeds 0.2 mg/cm$^2$ (e.g., at least 2 mg/cm$^2$, at least 3 mg/cm$^2$, at least 4 mg/cm$^2$, at least 5 mg/cm$^2$, at least 6 mg/cm$^2$, etc.). For example, in some embodiments, the transdermal delivery device can have a total dextromethorphan loading of about 0.2 mg/cm$^2$ to about 8 mg/cm$^2$, e.g., about 0.2 mg/cm$^2$ to about 2 mg/cm$^2$ (e.g., about 0.2 mg/cm$^2$, about 0.3 mg/cm$^2$, about 0.4 mg/cm$^2$, about 0.5 mg/cm$^2$, about 0.6 mg/cm$^2$, about 0.7 mg/cm$^2$, about 0.8 mg/cm$^2$, about 0.9 mg/cm$^2$, about 1 mg/cm$^2$, about 1.2 mg/cm$^2$, about 1.5 mg/cm$^2$, about 1.8 mg/cm$^2$, about 2 mg/cm$^2$, or any ranges between the recited values such as about 0.2-1 mg/cm$^2$, about 0.5-1 mg/cm$^2$, about 0.5-1.5 mg/cm$^2$, etc.), about 0.5 mg/cm$^2$ to about 8 mg/cm$^2$ or about 2 mg/cm$^2$ to about 6 mg/cm$^2$ (e.g., about 2 mg/cm$^2$, about 3 mg/cm$^2$, about 4 mg/cm$^2$, about 5 mg/cm$^2$, about 6 mg/cm$^2$, or any ranges between the recited values). As used herein, the total dextromethorphan loading of a patch can be calculated by dividing the total amount of the dextromethorphan in the patch by the patch's active surface area.

Exemplary Transdermal Delivery Devices and Formulations

In some embodiments, the present disclosure also provides the following non-limiting exemplary transdermal delivery devices, or alternatively referred to herein as transdermal patches or simply patches, and transdermal formulations such as adhesive compositions.

In some embodiments, the present disclosure provides an adhesive composition comprising (1) dextromethorphan; (2) a pressure sensitive adhesive; (3) a skin permeation enhancer (e.g., isopropyl myristate); and optionally (4) a crystallization inhibitor (e.g., a vinylpyrrolidone polymer, such as vinyl pyrrolidone homopolymer (or povidone), for example, Povidone K30, Plasdone K29/32 and the alike). In some embodiments, the dextromethorphan is in an amount of about 2% to about 12%, preferably, about 6% to about 12% (e.g., about 6%, about 7%, about 8%, about 9%, about 10%, about 11%, about 12%, or any ranges between the recited values, such as about 8-12% etc.) by weight of the adhesive composition; the skin permeation enhancer (e.g., isopropyl myristate) is in an amount of about 6% to about 12% (e.g., about 6%, about 7%, about 8%, about 9%, about 10%, about 11%, about 12%, or any ranges between the recited values, such as about 8-12% etc.) by weight of the adhesive composition; and the pressure sensitive adhesive in an amount of about 65% to about 85% (e.g., about 65%, about 70%, about 75%, about 80%, about 85%, or any ranges between the recited values, such as about 65-85%, about 70-85%, about 75-85% etc.) by weight of the adhesive composition. The dextromethorphan and skin permeation enhancer are typically dispersed (e.g., homogenously dispersed or dissolved) in the pressure sensitive adhesive. In some embodiments, the dextromethorphan and skin permeation enhancer are homogeneously mixed with the pressure sensitive adhesive. In some embodiments, the adhesive composition is a homogeneous mixture. In some embodiments, the adhesive composition comprises the crystallization inhibitor in an amount of about 6% to about 12% (e.g., about 6%, about 7%, about 8%, about 9%, about 10%, about 11%, about 12%, or any ranges between the recited values, such as about 8-12% etc.) by weight. In some embodiments, the adhesive composition comprises dextromethorphan as the only active ingredient. In some embodiments, the skin permeation enhancer is isopropyl myristate. The pressure sensitive adhesive can be any of those described herein. Typically, the pressure sensitive adhesive is an acrylate copolymer adhesive, e.g., a poly acrylate vinyl acetate copolymer, such as those having non-acidic hydroxyl functional groups, for example, described herein such as Duro-Tak 87-2287 adhesive and the alike, manufactured by Henkel Adhesives. In some embodiments, the pressure sensitive adhesive comprises an acrylate copolymer adhesive and an additional adhesive. For example, in some embodiments, the pressure sensitive adhesive can be a mixture of an acrylate copolymer adhesive (e.g., Durotak 87-2287) and a silicone adhesive (e.g., BIO-7-4202) in various ratios (e.g., a weight ratio of acrylate adhesive to silicone adhesive ranging from about 1:20 to about 20:1, e.g., about 10:1 to about 1:10, such as about 10:1, about 4:1, about 1:1, about 1:4, or any ranges between the recited value. The crystallization inhibitor, when present, can be a vinylpyrrolidone polymer, such as vinyl pyrrolidone homopolymer (or povidone), for example, Povidone K30, Plasdone K29/32 and the alike. In some embodiments, the crystallization inhibitor is a vinylpyrrolidone polymer with a nominal K value of about 25-35, such as about 29-32. The K-values assigned to various grades of PVP polymer represent a function of the average molecular weight, the degree of polymerization and the intrinsic viscosity. The K-values are derived from viscosity measurements and are calculated according to Fikentscher's formula. As those skilled in the art would understand that any nominal K value allows certain variations from the nominal value, typically, 90-108%. For example, for Povidone K30, i.e., the nominal K value is 30, the US Pharmacopeia and European Pharmacopeia typically allow a 90%-108% variation of the stated value; thus, a povidone having a K value ranging between 27.0-32.4 is within the specification for Povidone K30 polymers. Unless otherwise obvious from context, the K value referred to herein should be understood as nominal K value. In any of the embodiments described herein, unless otherwise specified or contradictory from context, the vinylpyrrolidone polymer, such as vinyl pyrrolidone homopolymer (or povidone), can have a nominal K value of about 25-35, such as about 29-32. Vinylpyrrolidone polymer as used herein should be understood generally as encompassing both homopolymers and copolymers. The adhesive composition is typically used as an adhesive layer (e.g., drug-in-adhesive layer) in the transdermal delivery device described herein.

In some embodiments, the present disclosure provides a transdermal patch comprising a) a backing layer (e.g., described herein); and b) the adhesive composition or adhesive layer disclosed herein. The adhesive surface is typically protected with a release liner prior to use. Suitable release liners are described herein. In some embodiments, the transdermal patch comprises, consists essentially of or consists of a) a backing layer; b) the adhesive composition or adhesive layer disclosed herein; and c) an optionally release liner.

The transdermal patch herein typically comprises a drug-in-adhesive layer, which comprises, consists essentially of, or consists of (1) dextromethorphan; (2) a pressure sensitive adhesive; (3) a skin permeation enhancer (e.g., isopropyl myristate); and optionally (4) a crystallization inhibitor (e.g., a vinylpyrrolidone polymer, such as vinyl pyrrolidone homopolymer (or povidone), for example, Povidone K30, Plasdone K29/32 and the alike), wherein dextromethorphan is in an amount of about 2% to about 12%, preferably, about 6% to about 12% (e.g., about 6%, about 7%, about 8%, about 9%, about 10%, about 11%, about 12%, or any ranges between the recited values, such as about 8-12% etc.) by weight; the skin permeation enhancer (e.g., isopropyl myristate) is in an amount of about 6% to about 12% (e.g., about 6%, about 7%, about 8%, about 9%, about 10%, about 11%, about 12%, or any ranges between the recited values, such as about 8-12% etc.) by weight; and the pressure sensitive adhesive in an amount of about 65% to about 85% (e.g., about 65%, about 70%, about 75%, about 80%, about 85%, or any ranges between the recited values, such as about 65-85%, about 70-85%, about 75-85% etc.) by weight. The dextromethorphan and skin permeation enhancer are typically dispersed (e.g., homogenously dispersed or dissolved) in the pressure sensitive adhesive. In some embodiments, the dextromethorphan and skin permeation enhancer are homogeneously mixed with the pressure sensitive adhesive. In some embodiments, the drug-in-adhesive layer is a homogeneous mixture. In some embodiments, the drug-in-adhesive layer comprises the crystallization inhibitor in an amount of about 6% to about 12% (e.g., about 6%, about 7%, about 8%, about 9%, about 10%, about 11%, about 12%, or any ranges between the recited values, such as about 8-12% etc.) by weight. In some embodiments, the drug-in-adhesive layer comprises dextromethorphan as the only active ingredient. In some embodiments, the skin permeation enhancer is isopropyl myristate. The pressure sensitive adhesive can be any of those described herein. Typically, the pressure sensitive adhesive is an acrylate copolymer adhesive, e.g., a poly acrylate vinyl acetate copolymer such as those having non-acidic hydroxyl functional groups, for example, described herein such as Duro-Tak 87-2287 adhesive and the alike, manufactured by Henkel Adhesives. In some embodiments, the pressure sensitive adhesive comprises an acrylate copolymer adhesive and an additional adhesive. For example, in some embodiments, the pressure sensitive adhesive can be a mixture of an acrylate copolymer adhesive (e.g., Durotak 87-2287) and a silicone adhesive (e.g., BIO-7-4202) in various ratios (e.g., a weight ratio of acrylate adhesive to silicone adhesive ranging from about 1:20 to about 20:1, e.g., about 10:1 to about 1:10, such as about 10:1, about 4:1, about 1:1, about 1:4, or any ranges between the recited value. The crystallization inhibitor, when present, can be a vinylpyrrolidone polymer, such as vinyl pyrrolidone homopolymer (or povidone), for example, Povidone K30, Plasdone K29/32 and the alike. In some embodiments, the crystallization inhibitor is a vinylpyrrolidone homopolymer polymer with a nominal K value of about 25-35, such as about 29-32. In some embodiments, the drug-in-adhesive layer comprises, consists essentially of, or consists of (1) dextromethorphan; (2) a poly acrylate vinyl acetate copolymer pressure sensitive adhesive, such as those having non-acidic hydroxyl functional groups, for example, described herein such as Duro-Tak 87-2287 adhesive and the alike; (3) isopropyl myristate; and (4) a vinylpyrrolidone polymer, such as vinyl pyrrolidone homopolymer (or povidone), for example, Povidone K30, Plasdone K29/32 and the alike, wherein the ranges/amounts of each components can be any of those described herein as suitable in any combination. The transdermal patch typically has an active surface area of about 30 $cm^2$ to about 100 $cm^2$, e.g., about 30 $cm^2$, about 40 $cm^2$, about 50 $cm^2$, about 60 $cm^2$, about 70 $cm^2$, about 80 $cm^2$, about 90 $cm^2$, about 100 $cm^2$, or any ranges between the recited values, such as about 40-60 $cm^2$, about 60-80 $cm^2$, etc. In some embodiments, the transdermal patch has an active surface area of about 70 $cm^2$. In some embodiments, the transdermal patch can also have an active surface area of greater than about 100 $cm^2$, e.g., up to 300 $cm^2$.

The transdermal patch herein can also be configured to contain desired amounts of dextromethorphan. In some embodiments, the transdermal patch comprises a drug-in-adhesive layer comprising, consisting essentially of, or consisting of (1) about 20 mg to about 100 mg of dextromethorphan, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of dextromethorphan; (2) about 30 mg to about 100 mg of isopropyl myristate, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of isopropyl myristate; (3) about 150 mg to about 900 mg of a pressure sensitive adhesive, e.g., about 300 mg, about 350 mg, about 400 mg, about 450 mg, about 500 mg, about 550 mg, about 600 mg, about 700 mg, about 800 mg, about 900 mg, or any ranges between the recited values, such as about 300-500 mg, 350-450 mg, or about 300-550 mg, etc. of the pressure sensitive adhesive; and optionally (4) a crystallization inhibitor in an amount of about 30 mg to about 100 mg, e.g., in an amount of about 30 mg, about 40 mg, about 50 mg, about 60 mg, about 70 mg, about 80 mg, about 90 mg, about 100 mg, or any ranges between the recited values, such as about 40-60 mg, 50-60 mg, or about 50-70 mg, etc. The dextromethorphan and isopropyl myristate are typically dispersed (e.g., homogenously dispersed or dissolved) in the pressure sensitive adhesive. In some embodiments, the dextromethorphan and isopropyl myristate are homogenously mixed with the pressure sensitive adhesive. In some embodiments, the drug-in-adhesive layer is a homogeneous mixture. In some embodiments, the pressure sensitive adhesive is an acrylate based adhesive, e.g., acrylate copolymers. In some embodiments, the pressure sensitive adhesive is a poly acrylate vinyl acetate copolymer such as those having non-acidic hydroxyl functional groups, for example, described herein such as Duro-Tak 87-2287 adhesive and the alike. In some embodiments, the pressure sensitive adhesive comprises an acrylate copolymer adhesive and an additional adhesive. For example, in some embodiments, the pressure sensitive adhesive can be a mixture of an acrylate copolymer adhesive (e.g., Durotak 87-2287) and a silicone adhesive (e.g., BIO-7-4202) in various ratios (e.g., a weight ratio of acrylate adhesive to silicone adhesive ranging from about 1:20 to about 20:1, e.g., about 10:1 to about 1:10, such as about 10:1, about 4:1, about 1:1, about 1:4, or any ranges between the recited value. In some embodiments, the drug-in-adhesive layer comprises the crystallization inhibitor. In some embodiments, the crystallization inhibitor is a vinylpyrrolidone polymer, such as vinyl pyrrolidone homopolymer (or povidone), for example, Povidone K30, Plasdone K29/32 and the alike. In some embodiments, the crystallization inhibitor is a vinylpyrrolidone homopolymer polymer with a nominal K value of about 25-35, such as about 29-32. Typically, the drug-in-adhesive layer comprises dextromethorphan in an amount of about 6% to about 12% (e.g., described herein, such as about 10%) by weight; isopropyl myristate in an amount of about 6% to about 12%

(e.g., described herein, such as about 10%) by weight; the pressure sensitive adhesive in an amount of about 65% to about 85% (e.g., described herein, such as about 70% or about 80%) by weight; and the crystallization inhibitor, when present, in an amount of about 6% to about 12% (e.g., described herein, such as about 10%) by weight. In some embodiments, the drug-in-adhesive layer comprises dextromethorphan as the only active ingredient. In some embodiments, the drug-in-adhesive layer comprises about 56 mg of dextromethorphan. In some embodiments, the transdermal patch comprises about 56 mg of dextromethorphan. The transdermal patch typically has an active surface area of about 30 $cm^2$ to about 100 $cm^2$, e.g., about 30 $cm^2$, about 40 $cm^2$, about 50 $cm^2$, about 60 $cm^2$, about 70 $cm^2$, about 80 $cm^2$, about 90 $cm^2$, about 100 $cm^2$, or any ranges between the recited values, such as about 40-60 $cm^2$, about 60-80 $cm^2$, etc. In some embodiments, the transdermal patch has an active surface area of about 70 $cm^2$. In some embodiments, the transdermal patch can also have an active surface area of greater than about 100 $cm^2$, e.g., up to 300 $cm^2$. In any of the embodiments described herein, the transdermal patch can be in the form of a monolithic patch.

The transdermal patch herein typically has a total dextromethorphan loading of about 0.2 mg/$cm^2$ to about 5 mg/$cm^2$, such as about 0.2 mg/$cm^2$, about 0.3 mg/$cm^2$, about 0.4 mg/$cm^2$, about 0.5 mg/$cm^2$, about 0.6 mg/$cm^2$, about 0.7 mg/$cm^2$, about 0.8 mg/$cm^2$, about 0.9 mg/$cm^2$, about 1 mg/$cm^2$, about 2 mg/$cm^2$, about 5 mg/$cm^2$, or any ranges between the recited values, such as about 0.2-1 mg/$cm^2$, 0.2-2 mg/$cm^2$, about 0.5-1 mg/$cm^2$, etc. Typically, for use in a once-a-day dosing regimen, the transdermal patch herein can have a lower total dextromethorphan loading, for example, ranging from about 0.2 mg to about 1 mg/$cm^2$. On the other hand, when the dosing intervals are longer, such as a once-a-week dosing regimen, or between once-a-day to once-a-week, the transdermal patch herein can have a relatively higher total dextromethorphan loading, for example, ranging from about 1 mg to about 5 mg/$cm^2$.

Typically, the amount of dextromethorphan included in the transdermal patch herein is sufficient to deliver a therapeutically effective amount of dextromethorphan to a subject in need thereof. In some embodiments, the amount of dextromethorphan included in the transdermal patch herein is sufficient to transdermally deliver a daily dose of about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan to a subject in need thereof. Preferably, one single patch is used to deliver the daily dose herein. For example, for a once daily dosing regimen, preferably, one single patch is applied once a day to deliver the daily dose; however, in some cases, two or more patches can be applied at substantially the same time, once a day, to satisfy the desired daily dose. In some embodiments, the transdermal patch can be suitable for use as a 1-day patch, 2-day patch, 3-day patch, 4-day patch, 5-day patch, 6-day patch, or 7-day patch, wherein the patch includes a sufficient amount of dextromethorphan such that when the patch is applied to the subject for the designed duration (e.g., 1 day for 1-day patch, 2 days for 2-day patch, etc.), it delivers a daily dose of about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan to a subject in need thereof.

In some preferred embodiments, the transdermal patch herein (e.g., a 1-day patch) can include an amount of dextromethorphan sufficient to deliver about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan to a subject in need thereof when the patch is applied to the subject for 24 hours. The required amount of dextromethorphan for the transdermal patches herein to achieve the desired daily dose typically does not exceed twice the amount of the desired daily dose. For example, in some embodiments, the desired daily dose is about 35 mg, and the transdermal patch can include less than 70 mg of dextromethorphan, such as less than 60 mg of dextromethorphan. Thus, the transdermal bioavailability (i.e., the delivered dextromethorphan divided by initial dextromethorphan in the patch) is generally higher than 50%, up to 80% or higher. This high bioavailability is made possible in part due to the unexpected discovery that it is possible to achieve continuously high flux of dextromethorphan for the transdermal patches herein. In some embodiments, the patches are designed to be worn for a longer duration such as 2 days and up to a week. And in such embodiments, the residue dextromethorphan at the end of the application typically is also less than the desired daily dose.

The transdermal patches herein typically have a dextromethorphan flux suitable for delivering a therapeutically effective amount to a subject in need thereof. For example, in some embodiments, the transdermal patch has a dextromethorphan flux of at least about 200 ug/$cm^2$/day, when measured in vitro using human cadaver skin, such as about 200 ug/$cm^2$/day, about 300 ug/$cm^2$/day, about 400 ug/$cm^2$/day, about 500 ug/$cm^2$/day, about 600 ug/$cm^2$/day, about 700 ug/$cm^2$/day, about 800 ug/$cm^2$/day, about 1000 ug/$cm^2$/day, or any ranges between the recited values, such as about 200-800 ug/$cm^2$/day, about 300-800 ug/$cm^2$/day, about 400-800 ug/$cm^2$/day, about 500-800 ug/$cm^2$/day, etc. As discussed herein, it was found that a crystallization inhibitor vinylpyrrolidone polymer (Plasdone K29/32) can significantly enhance the flux of dextromethorphan from the transdermal patches herein, both in vitro and in vivo. In any of the embodiments described herein, unless directly contradictory from context, the transdermal patch herein preferably includes in the drug-in-adhesive layer a crystallization inhibitor described herein, such as a vinylpyrrolidone polymer, such as vinyl pyrrolidone homopolymer (or povidone), for example, Povidone K30, Plasdone K29/32 and the like. The crystallization inhibitor is typically included in an amount of about 6% to about 12% (e.g., about 6%, about 7%, about 8%, about 9%, about 10%, about 11%, about 12%, or any ranges between the recited values, such as about 8-12% etc.) by weight of the drug-in-adhesive layer. In some embodiments, the crystallization inhibitor can also be included in an amount higher than about 12%, for example, up to 50%, so long as the adhesive layer can still maintain sufficient adhesion suitable for the subject to wear it for a desired duration, such as 24 hours.

In some embodiments, the present disclosure also provides a method of selecting a transdermal patch for the methods herein (e.g., methods of treating PBA), the method comprises measuring in vitro dextromethorphan flux from a transdermal patch disclosed herein (e.g., those shown in [18]-[35] in the Brief Summary Section), e.g., using human cadaver skin, and selecting a transdermal patch having dextromethorphan flux of at least about 200 ug/$cm^2$/day, when measured in vitro using human cadaver skin, such as about 200 ug/$cm^2$/day, about 300 ug/$cm^2$/day, about 400 ug/$cm^2$/day, about 500 ug/$cm^2$/day, about 600 ug/$cm^2$/day, about 700 ug/cm$^2$/day, about 800 ug/cm$^2$/day, about 1000 ug/cm$^2$/day, or any ranges between the recited values, such as about 200-800 ug/cm$^2$/day, about 300-800 ug/cm$^2$/day, about 400-800 ug/cm$^2$/day, about 500-800 ug/cm$^2$/day, etc.

In some specific embodiments, the transdermal patch comprises, consists essentially of, or consists of a) a backing layer (e.g., described herein), b) a drug-in-adhesive layer, and c) an optional release liner, wherein the drug-in-adhesive layer comprises (1) dextromethorphan in an amount of about 6% to about 12% (e.g., described herein, such as about 10%) by weight; (2) a poly acrylate vinyl acetate copolymer pressure sensitive adhesive, such as those having non-acidic hydroxyl functional groups, for example, described herein such as Duro-Tak 87-2287 adhesive and the alike, in an amount of about 65% to about 85% (e.g., described herein, such as about 70%) by weight; (3) isopropyl myristate in an amount of about 6% to about 12% (e.g., described herein, such as about 10%) by weight; and (4) a vinylpyrrolidone polymer, such as vinyl pyrrolidone homopolymer (or povidone), for example, Povidone K30, Plasdone K29/32 and the like, in an amount of about 6% to about 12% (e.g., described herein, such as about 10%) by weight. In some embodiments, the transdermal patch has a dextromethorphan flux of at least about 400 ug/cm$^2$/day (e.g., about 500 ug/cm$^2$/day to about 800 ug/cm$^2$/day) when measured in vitro using human cadaver skin.

In some specific embodiments, the present disclosure provides a monolithic transdermal patch, which comprises, consists essentially of, or consists of a) a backing layer (e.g., described herein), b) a drug-in-adhesive layer, and c) an optional release liner, wherein the drug-in-adhesive layer comprises, consists essentially of, or consists of (1) about 20 mg to about 100 mg (e.g., described herein, such as about 56 mg) of dextromethorphan; (2) about 150 mg to about 900 mg (e.g., described herein, such as about 392 mg) a poly acrylate vinyl acetate copolymer pressure sensitive adhesive, such as those having non-acidic hydroxyl functional groups, for example, described herein such as Duro-Tak 87-2287 adhesive and the alike; (3) about 30 mg to about 100 mg (e.g., described herein, such as about 56 mg) of isopropyl myristate; and (4) about 30 mg to about 100 mg (e.g., described herein, such as about 56 mg) of a vinylpyrrolidone polymer, such as vinyl pyrrolidone homopolymer (or povidone), for example, Povidone K30, Plasdone K29/32 and the like. In some embodiments, the weigh percentage of ingredients in the drug-in-adhesive layer can be (1) dextromethorphan in an amount of about 6% to about 12% (e.g., described herein, such as about 10%) by weight; (2) the poly acrylate vinyl acetate copolymer pressure sensitive adhesive, such as those having non-acidic hydroxyl functional groups, for example, described herein such as Duro-Tak 87-2287 adhesive and the alike, in an amount of about 65% to about 85% (e.g., described herein, such as about 70%) by weight; (3) isopropyl myristate in an amount of about 6% to about 12% (e.g., described herein, such as about 10%) by weight; and (4) the vinylpyrrolidone polymer, such as vinyl pyrrolidone homopolymer (or povidone), for example, Povidone K30, Plasdone K29/32 and the like, in an amount of about 6% to about 12% (e.g., described herein, such as about 10%) by weight. In some embodiments, the transdermal patch has an active surface area of about 30 cm$^2$ to about 100 cm$^2$ (e.g., described herein, such as about 70 cm$^2$). In some embodiments, the transdermal patch has a dextromethorphan flux of at least about 400 ug/cm$^2$/day (e.g., about 500 ug/cm$^2$/day to about 800 ug/cm$^2$/day) when measured in vitro using human cadaver skin.

In some embodiments, the present disclosure also provides a transdermal patch comprising, consisting essentially of, or consisting of a backing layer, a drug-in-adhesive layer, and optionally a release liner, wherein the drug-in-adhesive layer comprises a formulation selected from Formulation A, B, C1, C2, C3, D0, D1, D2, and E1, as shown in the Examples section. In some specific embodiments, the drug-in-adhesive layer comprises, consists essentially of, or consists of Formulation E1 which contains, by dry weight percentage, about 10% of dextromethorphan base, about 10% of isopropyl myristate, about 70% of polyacrylate adhesive (DuroTak 387-2287), and about 10% of crystallization inhibitor Plasdone K-29/32. In some specific embodiments, the drug-in-adhesive layer comprises, consists essentially of, or consists of Formulation E1 produced by the method according to the process described in Example 1. In some embodiments, the transdermal patch has about 56 mg of dextromethorphan base and a size of about 70 cm$^2$. In any of the embodiments described herein, unless otherwise contradictory from context, the transdermal patch herein can have a drug-in-adhesive layer comprising, consisting essentially of, or consisting of Formulation E1, which contains, by dry weight percentage, about 10% of dextromethorphan base, about 10% of isopropyl myristate, about 70% of polyacrylate adhesive (DuroTak 387-2287), and about 10% of crystallization inhibitor Plasdone K-29/32; or Formulation E1 produced by the method according to the process described in Example 1.

The transdermal patches and formulations are preferably storage stable when stored at room temperature (25±2° C.) at 60% relative humidity (RH)±5% RH for about 1 month, 3 months, 6 months or longer. By storage stable, it is to be meant that the transdermal patches or formulations would be accepted by those skilled in the art as equivalent to the initial transdermal patches or formulations, i.e., at the beginning of the storage. Storage stable is typically characterized by one or more of the following: (1) substantially same amount of drug related impurities, no significant increased amount of either individual or total impurities; (2) substantially same amount of dextromethorphan; (3) substantially same physical properties such as peel adhesion, shear adhesion, task force, release force, etc.; and (4) substantially same drug release rate and/or dextromethorphan permeation rate. "Substantially same" should be understood as meaning within 80-125% or measurement error margin. For example, patches prepared from Formulation E1 which contain 56 mg dextromethorphan with an active surface area of about 70 cm$^2$ were found to be storage stable after storage at room temperature (25±2° C.) at 60% relative humidity (RH)±5% RH for 6 months or longer.

In some embodiments, the present disclosure also provides a method of preparing a transdermal delivery device or adhesive composition. In some embodiments, the method comprises: a) mixing dextromethorphan, an adhesive (e.g., a pressure sensitive adhesive described herein such as Duro-Tak 87-2287), a permeation enhancer (e.g., isopropyl myristate) and an optional crystallization inhibitor (e.g., described herein such as a vinylpyrrolidone polymer, such as vinyl pyrrolidone homopolymer (or povidone), for example, Povidone K30, Plasdone K29/32 and the alike) in a suitable solvent (e.g., an organic solvent such as an ester solvent or an alcohol solvent, typically volatile, e.g., ethyl acetate or isopropanol or combinations thereof) to form a homogenous mixture; b) casting the homogenous mixture onto a release liner; and c) drying the casting to remove the solvent to form an adhesive composition on the release liner. In some embodiments, the method further comprises laminating the adhesive composition to a backing layer. Suitable amount of dextromethorphan and suitable adhesive, optional crystallization inhibitor, permeation enhancer and their respective amount, can include any of those described herein in any combination. The adhesive composition, with or without the release liner, and transdermal delivery device prepared by the methods herein are also novel aspects of the present disclosure. Some exemplary procedures are described herein in the Examples section.

TDD with an Optional Reservoir Layer

In some embodiments, a reservoir layer can be optionally included in the transdermal delivery device herein. For example, for high daily doses and/or application for an extended period of time (e.g., 1 day or more), the reservoir layer can provide more sustained flux of dextromethorphan to a user.

In some embodiments, the transdermal delivery device comprises an adhesive layer comprising an adhesive and optionally a reservoir layer comprising dextromethorphan. In some embodiments, the adhesive layer optionally comprises dextromethorphan dispersed in the adhesive. In some embodiments, the adhesive layer does not include dextromethorphan, other than through equilibrium with the reservoir layer. In some embodiments, the adhesive layer comprises dextromethorphan dispersed in the adhesive. In some embodiments, the reservoir layer comprises dextromethorphan in an adhesive. In some embodiments, the reservoir layer and the adhesive layer are the same layer. In some embodiments, the reservoir layer is sandwiched between the adhesive layer and a backing layer. In some embodiments, the reservoir layer can be sandwiched between two adhesive layers which can be the same or different. For example, in some embodiments, the two adhesive layers can have the same ingredients with the same concentrations, and in some embodiments, can also have the same thickness. However, in some embodiments, the two adhesive layers can have different ingredients, or same ingredients with different concentrations, or have different thickness, etc. An exemplary configuration can be seen in FIG. 5, where the adhesive layer is the top layer, and the backing layer or an adhesive layer, which can be the same as or different from the top layer, is the bottom layer, and the reservoir layer is the middle layer.

In some embodiments, the reservoir layer is separated from the adhesive layer by a membrane, e.g., a rate controlling membrane such as a microporous membrane. The reservoir layer preferably contains an adhesive; however, other designs of the reservoir layer are also suitable when compatible with the adhesive layer and the backing layer. For example, in some embodiments, the reservoir layer can be a scrim/nonwoven fabric saturated with dextromethorphan, or having dextromethorphan dispersed in other suitable carrier/substrate.

Dextromethorphan can be included in the adhesive layer and reservoir layer in various concentrations. Typically, the concentration of dextromethorphan in the reservoir layer is higher than that in the adhesive layer. For example, in some embodiments, the adhesive layer can comprise dextromethorphan in an amount of about 2% to about 12% (e.g., about 2%, about 4%, about 6%, about 8%, about 10%, about 12%, or any range between the recited values) by weight of the adhesive layer; whereas the reservoir layer can comprise dextromethorphan in an amount of about 20% or more, for example, about 30% or more, about 40% or more, about 50% or more, such as about 20% to about 60%, about 30% to about 50%, by weight of the reservoir layer. In some embodiments, the adhesive layer comprises dextromethorphan in an amount of about 6% to about 12% (e.g., about 6%, about 7%, about 8%, about 9%, about 10%, about 11%, about 12%, or any ranges between the recited values) by weight of the adhesive layer. In some embodiments, the adhesive layer comprises dextromethorphan at or near the saturation concentration in the adhesive, for example, about 10% by weight in an acrylate adhesive. In some embodiments, the reservoir layer comprises dextromethorphan above the saturation concentration in the adhesive. In other words, the dextromethorphan in the reservoir layer is over-saturated and can therefore contain solid dextromethorphan, which can serve as a drug depot.

Suitable adhesives for the adhesive layer and the reservoir layer, as applicable, include any of those described herein, preferably pressure sensitive adhesives. The adhesives included in the adhesive layer and reservoir layer can be the same or different. In some embodiments, the adhesives included in the adhesive layer and reservoir layer are the same, for example, acrylate based adhesives. Other suitable adhesives include a polyisobutylene adhesive, a silicone polymer adhesive, an acrylate copolymer adhesive (e.g., a poly acrylate vinyl acetate copolymer, such as those having non-acidic hydroxyl functional groups, for example, described herein such as Duro-Tak 87-2287 adhesive and the alike), or a combination thereof. For example, in any of the embodiments described herein, unless directly contrary from context, the pressure sensitive adhesive can be a poly acrylate vinyl acetate copolymer, e.g., containing non-acidic hydroxyl functional groups, such as DuroTak® 2287 adhesives as described herein. In some embodiments, the adhesive can be a mixture of an acrylate copolymer adhesive (e.g., Durotak 87-2287) and a silicone adhesive (e.g., BIO-7-4202) in various ratios (e.g., a weight ratio of acrylate adhesive to silicone adhesive ranging from about 1:20 to about 20:1). In some embodiments, the weight ratio of the acrylate adhesive to silicon adhesive ranges from about 10:1 to about 1:10 (e.g., about 10:1, about 4:1, about 1:1, about 1:4, or any ranges between the recited value). In any of the embodiments described herein, the adhesive layer can be configured for adhering to a user's skin continuous for at least 1 day (e.g., at least 2 days, at least 3 days, at least 4 days, at least 5 days, at least 6 days, at least 7 days).

The adhesive (e.g., a pressure sensitive adhesive) typically is the main ingredient for the adhesive layer and reservoir layer (as applicable). For example, in some embodiments, the adhesive layer comprises a pressure sensitive adhesive in an amount of about 50% to about 90% by weight of the adhesive layer. In some embodiments, the pressure sensitive adhesive is present in an amount of about 60% to about 85% (e.g., about 60%, about 70%, about 75%, about 80%, about 85%, or any ranges between the recited values) by weight of the adhesive layer. In some embodiments, the reservoir layer can include a pressure sensitive adhesive in an amount of about 20% to about 80% by weight of the reservoir layer. For example, in some embodiments, the pressure sensitive adhesive is present in an amount of about 20% to about 65% (e.g., about 20%, about 30%, about 35%, about 40%, about 50%, about 60%, about 65%, or any ranges between the recited values) by weight of the reservoir layer.

Suitable sizes for the transdermal delivery device are described herein. In some embodiments, the transdermal delivery device has an active surface area of about 5 $cm^2$ to about 200 $cm^2$. In some embodiments, the transdermal delivery device has an active surface area of about 10 $cm^2$ to about 150 $cm^2$. In some embodiments, the transdermal delivery device has an active surface area of about 30 $cm^2$ to about 100 $cm^2$ (e.g., about 30 $cm^2$, about 40 $cm^2$, about 50 $cm^2$, about 60 $cm^2$, about 70 $cm^2$, about 80 $cm^2$, about 90 $cm^2$, about 100 $cm^2$, or any ranges between the recited values).

The adhesive layer and reservoir layer can be of various thickness. For example, in some embodiments, the adhesive layer is about 0.1 mil to about 10 mils thick (e.g., about 0.5 mil to about 10 mils, about 1 mil to 10 mils). In some embodiments, the reservoir layer can also be about 0.1 mil to about 10 mils thick (e.g., about 0.5 mil to about 10 mils, about 1 mil to 10 mils).

Skin permeation enhancers can also be included in the adhesive layer and the reservoir layer. For example, in some embodiments, the adhesive layer comprises a skin permeation enhancer selected from isopropyl myristate, oleyl oleate, oleic acid, glycerol monooleate, other fatty acids and fatty acid esters with carbon chain lengths of C12 to C18, and combinations thereof. In some embodiments, the adhesive layer comprises isopropyl myristate. Similarly, in some embodiments, the reservoir layer comprises a skin permeation enhancer selected from isopropyl myristate, oleyl oleate, oleic acid, glycerol monooleate, other fatty acids and fatty acid esters with carbon chain lengths of C12 to C18, and combinations thereof. In some embodiments, the reservoir layer comprises isopropyl myristate.

Various amounts of skin permeation enhancers can be used for the adhesive layer and the reservoir layer. Typically, the skin permeation enhancer can be present in an amount of about 2% to about 15% by weight of the adhesive layer or reservoir layer. For example, in some embodiments, the skin permeation enhancer is present in an amount of about 6% to about 12% (e.g., about 6%, about 7%, about 8%, about 9%, about 10%, about 11%, about 12%, or any ranges between the recited values) by weight of the adhesive layer. In some embodiments, the skin permeation enhancer is present in an amount of about 6% to about 12% (e.g., about 6%, about 7%, about 8%, about 9%, about 10%, about 11%, about 12%, or any ranges between the recited values) by weight of the reservoir layer. However, in some embodiments, the adhesive layer and/or the reservoir layer can also be substantially free of a skin permeation enhancer selected from isopropyl myristate, oleyl oleate, oleic acid, glycerol monooleate, other fatty acids and fatty acid esters with carbon chain lengths of C12 to C18, and combinations thereof.

In some embodiments, the adhesive layer and/or the reservoir layer can include an agent selected from a vinylpyrrolidone polymer (e.g., a vinylpyrrolidone-vinyl acetate copolymers), Kollidon (e.g., Kollidon 30 LP, Kollidon 90, or Kollidon VA64), silicone dioxide, titanium dioxide, and combinations thereof. In some embodiments, the agent can be present in an amount of about 2% to about 20% (e.g., about 2%, about 2.5%, about 3%, about 4%, about 5%, about 6%, about 10%, about 15%, about 20%, or any ranges between the recited values) by weight of the adhesive layer or reservoir layer. Without wishing to be bound by theories, it is believed that such agents can improve the cohesive strength of the adhesive layer or reservoir layer. Further, such agents can have other functions such as inhibiting crystallization. In some embodiments, the adhesive layer comprises an agent effective for improving cohesive strength of the adhesive layer. In some embodiments, the reservoir layer comprises an agent effective for improving cohesive strength of the reservoir layer.

It should be noted that the identities of ingredients such as adhesives, skin permeation enhancers, agents, and amounts thereof, for the adhesive layer and the reservoir layer are independently selected, which can be the same or different. Typically, the amounts can vary whereas the identity can be the same. In some embodiments, the adhesive layer can be a drug-in-adhesive layer described herein (e.g., as shown in [18]-[35] in the Brief Summary section). The thickness of the adhesive layer and the reservoir layer can also be the same or different.

As detailed in the Examples section, varying the adhesive components can affect the flux characteristics of the transdermal delivery device comprising dextromethorphan. Thus, in some embodiments, the present disclosure also provides a transdermal delivery device comprising an adhesive layer, wherein the adhesive layer comprises two or more adhesives. Typically, the adhesive layer comprises dextromethorphan dispersed (e.g., homogeneously dispersed) in the two or more adhesives. The dextromethorphan is typically present in an amount of about 6% to about 12% (e.g., about 6%, about 7%, about 8%, about 9%, about 10%, about 11%, about 12%, or any ranges between the recited values) by weight of the adhesive layer.

In some embodiments, the adhesive layer can include a mixture of an acrylate copolymer adhesive (e.g., Durotak 87-2287) and a silicone adhesive (e.g., BIO-7-4202) in various ratios (e.g., a weight ratio of acrylate adhesive to silicone adhesive ranging from about 1:20 to about 20:1). In some embodiments, the weight ratio of the acrylate adhesive to silicon adhesive ranges from about 10:1 to about 1:10 (e.g., about 10:1, about 4:1, about 1:1, about 1:4, or any ranges between the recited value). In some embodiments, unless obvious to the contrary from context, the mixture of acrylate copolymer adhesive and silicone adhesive can be used in any of the drug-in-adhesive layer described herein. Other ingredients and suitable amounts that can be optionally included in the adhesive layer, such as skin permeation enhancers, include those described herein.

The adhesive layer with two or more adhesives can be included/used in any of the transdermal delivery device herein. For example, in some embodiments, the transdermal delivery device comprising a reservoir layer described herein can have an adhesive layer with a mixture of an acrylate copolymer adhesive (e.g., Durotak 87-2287) and a silicone adhesive (e.g., BIO-7-4202) in various ratios described herein. In some embodiments, the transdermal delivery device comprises the adhesive layer with a mixture of an acrylate copolymer adhesive (e.g., Durotak 87-2287) and a silicone adhesive (e.g., BIO-7-4202) in various ratios described herein with or without the reservoir layer described herein.

Skin permeation enhancers (transdermal enhancers) can enhance the skin permeability of dextromethorphan through the skin and can be optionally included in the transdermal delivery device herein. Various skin permeation enhancers can be included. Non-limiting useful skin permeation enhancers include, for example, sulfoxides (e.g., dimethylsulfoxide, DMSO), Azones (e.g., laurocapram), pyrrolidones (e.g., 2-pyrrolidone, 2P), alcohols and alkanols (e.g., ethanol or decanol), esters, glycols (e.g., propylene glycol (PG)), surfactants (e.g., Tween 80), terpenes, and combinations thereof. See, e.g., Williams et al., Adv Drug Deliv Rev. 27; 56(5):603-18 (2004). In some embodiments, the permeation enhancer comprises one or more compounds chosen from sulfoxides, alcohols, alkanols, esters, glycols, and surfactants. In some embodiments, the permeation enhancer comprises one or more compounds chosen from dimethyl sulfoxide (DMSO), oleic alcohol, oleayl oleate, oleic acid, levulinic acid, other fatty acids and fatty-acid esters, propylene glycol, dipropylene glycol, ethanol, and surfactants such as Tween 80. In some embodiments, the transdermal device can include one or more compounds chosen from DMSO, N-methyl-2-pyrolidone, azone, myristic acid, sesquiterpene oil, 4-decyloxazolidin-2-one, urea, and the like. In some embodiments, the skin permeation enhancer is selected from isopropyl myristate, oleyl oleate, oleic acid, glycerol monooleate, other fatty acids and fatty acid esters with carbon chain lengths of C12 to C18, and combinations thereof. In any of the embodiments described herein, unless otherwise directly contrary from context, the skin permeation enhancer can be isopropyl myristate.

The skin permeation enhancer is typically included in the amount of about 1% to about 25% by weight of an adhesive layer, for example, about 2%, about 5%, about 10%, about 15%, about 20%, about 25%, or any ranges between the specified values, by weight of the adhesive layer. In some embodiments, the transdermal device can be substantially free of a transdermal enhancer. In some embodiments, the transdermal device is substantially free of a transdermal enhancer if the amount of any potential such enhancers is about 20% or less than the least amount that has been shown to enhance transdermal flux by about 50% or more.

In some embodiments, the skin permeation enhancer and its amount are chosen to provide certain improved flux characteristics. For example, in some embodiments, the present disclosure provides a transdermal delivery device comprising an adhesive layer comprising dextromethorphan dispersed in an adhesive, wherein the adhesive layer comprises a skin permeation enhancer in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin. The dextromethorphan is typically present in an amount of about 6% to about 12% (e.g., about 6%, about 7%, about 8%, about 9%, about 10%, about 11%, about 12%, or any ranges between the recited values) by weight of the adhesive layer. The pressure sensitive adhesive is typically present in an amount of about 60% to about 85% (e.g., about 60%, about 65%, about 70%, about 75%, about 80%, about 85%, or any ranges between the recited values such as about 65-85%, about 60-80%, etc.) by weight of the adhesive layer. The term "otherwise equivalent transdermal delivery device without the skin permeation enhancer" should be understood as a control transdermal delivery device, wherein the content of the skin permeation enhancer in the adhesive layer is replaced with the adhesive, with all other aspects the same. For example, a transdermal delivery device includes an adhesive layer comprising 10% by weight of a skin permeation enhancer and 10% by weight dextromethorphan dispersed in 80% by weight acrylate adhesive, the otherwise equivalent device would include a respective adhesive layer with 10% by weight dextromethorphan dispersed in 90% by weight of the same acrylate adhesive, with all other aspects of the two devices being the same.

The skin permeation enhancer and its amount can also be adjusted to achieve flux enhancement at different time points post application. For example, in some embodiments, the permeation enhancer is in an amount to provide one or more of the following: 1) a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer; 2) a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer; and 3) a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin. As detailed in the Examples, in one example, when the amount of permeation enhancer, isopropyl myristate, is increased to about 10% by weight, significant enhancement of flux was observed even at or before 4 hours post application.

In some embodiments, the present disclosure also provides a method of selecting skin permeation enhancer and its amount for the transdermal patches herein, the method comprises measuring in vitro dextromethorphan flux from a test transdermal patch having a test skin permeation enhancer, e.g., using human cadaver skin, and selecting a skin permeation enhancer in an amount that provides one or more of the following: 1) a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer; 2) a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer; and 3) a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin.

The adhesive layer with a skin permeation enhancer can be included/used in any of the transdermal delivery devices herein. For example, in some embodiments, the transdermal delivery device comprising a reservoir layer described herein can have an adhesive layer with the adhesive layer with a skin permeation enhancer. Other ingredients and suitable amounts that can be optionally included in the adhesive layer include those described herein.

In some specific embodiments, the transdermal delivery device can include an adhesive layer and a reservoir layer, wherein the adhesive layer and reservoir layer can, for example, have the ingredients and amounts shown in the table below.

| | Example | Typical amount | Preferred Amount |
|---|---|---|---|
| Adhesive Layer Ingredients | | | |
| Adhesive | Duro-Tak 87-2287 | about 65% to about 85% | about 75% to about 77.5% |
| Drug | Dextromethorphan base | about 2% to about 12% | about 10% |
| Permeation enhancer | isopropyl myristate | about 6% to about 12% | about 10% |

-continued

| | Example | Typical amount | Preferred Amount |
|---|---|---|---|
| Others | Kollidon, e.g., Kollidon VA64 | about 1% to about 20% | about 2.5% to about 5% |
| Reservoir Layer Ingredients | | | |
| Adhesive | Duro-Tak 87-2287 | about 20% to about 70% | about 20% to about 57.5% |
| Drug | Dextromethorphan base | about 20% to about 60% | about 30% to about 50% |
| Permeation enhancer | isopropyl myristate | about 6% to about 12% | about 10% |
| Others | Kollidon, e.g., Kollidon VA64 | about 1% to about 20% | about 2.5% to about 20% |

All amounts in the table refer to the weight percentage of the respective layer (based on final formulation) with the total amount of each layer being 100%. In some embodiments, the transdermal delivery device can have an active surface area of about 60 $cm^2$ or more, e.g., about 70 $cm^2$. In some embodiments, the transdermal delivery device is configured to provide dextromethorphan about 15 mg/day to about 40 mg/day to a user, for example, about 15 mg/day, about 20 mg/day, about 25 mg/day, about 30 mg/day, about 35 mg/day, about 40 mg/day, or any ranges between the recited values. In some embodiments, the transdermal delivery device comprises about 50 mg to about 700 mg (e.g., about 50 mg, about 100 mg, about 150 mg, about 200 mg, about 300 mg, about 400 mg, about 500 mg, about 600 mg, about 700 mg, or any range between the recited values) dextromethorphan. In some embodiments, the reservoir layer can be sandwiched between two adhesive layers which can be the same or different. Typically, such transdermal delivery device also includes a backing layer and a release liner which protects the adhesive surface prior to use. Typically, these patches can be used for a dosing frequency of less than once a day, for example, once in one day, or two days or more, e.g., once a week, or 2, 3, 4, 5, or 6 times a week, such as twice a week.

In some specific embodiments, the transdermal delivery device can include an adhesive layer, which can, for example, have the ingredients and amounts shown in the table below.

| Adhesive Layer Ingredients | | | |
|---|---|---|---|
| | Example | Typical amount | Preferred Amount |
| Adhesive | Duro-Tak 87-2287 | about 65% to about 85% | about 80%, or about 75% to about 77.5% |
| Drug | Dextromethorphan base | about 2% to about 12% | about 10% |
| Permeation enhancer | isopropyl myristate | about 6% to about 12% | about 10% |
| Others | Kollidon, e.g., Kollidon VA64 | 0% to about 20% | 0%, or about 2.5% to about 5% |

All amounts in the table refer to the weight percentage of the final adhesive layer with the total amount being 100%. In some embodiments, the transdermal delivery device can have an active surface area of about 10 $cm^2$ or more, e.g., about 30 $cm^2$, about 45 $cm^2$, about 60 $cm^2$, about 75 $cm^2$, about 90 $cm^2$. In some embodiments, the transdermal delivery device is configured to provide dextromethorphan about 15 mg/day to about 40 mg/day to a user, for example, about 15 mg/day, about 20 mg/day, about 25 mg/day, about 30 mg/day, about 35 mg/day, about 40 mg/day, or any ranges between the recited values. In some embodiments, the transdermal delivery device comprises about 5 mg to about 100 mg (e.g., about 15 mg, about 30 mg, about 45 mg, about 60 mg, about 90 mg, or any range between the recited values) of dextromethorphan. Typically, such transdermal delivery device also includes a backing layer and a release liner which protects the adhesive surface prior to use. Typically, these patches can be used for a dosing frequency of no less than once a day, for example, once daily, or once in 12 hours, etc.

In Vitro Flux Characteristics

In some embodiments, the transdermal delivery device herein is configured to provide certain in vitro dextromethorphan flux profile, e.g., when tested using human cadaver skin. For example, in some embodiments, any of the transdermal delivery devices herein can be configured to provide 1) a mean cumulative dextromethorphan permeated of at least about 200 ug/$cm^2$ (ug refers to micrograms) (e.g., about 200 ug/$cm^2$ to about 2000 ug/$cm^2$) at 24 hours post application; and/or 2) a mean average flux of dextromethorphan of at least about 5 ug/$cm^2$*h (e.g., about 5 ug/$cm^2$*h to about 20 ug/$cm^2$*h, about 10 ug/$cm^2$*h to about 18 ug/$cm^2$*h) from 8 hours to 24 hours post application, when tested in vitro using human cadaver skin. In some embodiments, the present disclosure also provides a method of selecting a transdermal patch for the methods herein (e.g., methods of treating PBA), the method comprises measuring in vitro dextromethorphan flux from a transdermal patch disclosed herein (e.g., those shown in [18]-[35] in the Brief Summary Section), e.g., using human cadaver skin, and selecting a transdermal patch having dextromethorphan flux characterized in 1) a mean cumulative dextromethorphan permeated of at least about 200 ug/$cm^2$ (ug refers to micrograms) (e.g., about 200 ug/$cm^2$ to about 2000 ug/$cm^2$) at 24 hours post application; and/or 2) a mean average flux of dextromethorphan of at least about 5 ug/$cm^2$*h (e.g., about 5 ug/$cm^2$*h to about 20 ug/$cm^2$*h, about 10 ug/$cm^2$*h to about 18 ug/$cm^2$*h) from 8 hours to 24 hours post application, when tested in vitro using human cadaver skin.

In some embodiments, the transdermal delivery device can transdermally deliver to a subject in need thereof at least about 200 ug/$cm^2$ (e.g., about 200 ug/$cm^2$ to about 2000 ug/$cm^2$) per day. In some embodiments, the transdermal delivery device is configured to have a flux characteristic such that applying the transdermal delivery device to a subject in need thereof transdermally delivers dextromethorphan about 2 mg/day to about 50 mg/day to the subject. In some embodiments, the transdermal delivery device can transdermally deliver to the subject about 5 mg/day to about 50 mg/day (e.g., about 5 mg/day, about 10 mg/day, about 20 mg/day, about 30 mg/day, about 40 mg/day, about 50 mg/day, or any ranges between the recited values) to the subject for 1 day or more (e.g., 1.5 days, 2 days, 3 days, 4 days, 5 days, 6 days, 7 days, or any ranges between the recited values). The size of the transdermal delivery device is typically about 5 $cm^2$ to about 200 $cm^2$, for example, about 10 $cm^2$ to about 100 $cm^2$.

Transdermal delivery devices with the above flux characteristics can be prepared by those skilled in the art in view of the present disclosure. Preparations of a few transdermal delivery devices are also exemplified in the Examples section. The cumulative drug (dextromethorphan, deuterated dextromethorphan, or a combination thereof) permeated can be adjusted, for example, by varying the composition of the adhesive layer (e.g., drug concentration, permeation enhancer, drug load, types of adhesives etc.).

It should be noted that the pharmaceutical composition formulated for the adhesive layer and/or the reservoir layer described herein is also a novel aspect of the present disclosure.

The transdermal delivery device herein can also be characterized by certain in vivo release profile, e.g., to provide a desired pharmacokinetic (PK) profile, e.g., any of those described herein. In some embodiments, the transdermal delivery device can be configured to provide a PK profile in a subject in need thereof, e.g., any of the PK profile described herein (e.g., as shown in [46]-[62] in the Brief Summary section). In some embodiments, the transdermal delivery device is configured to provide a PK profile effective, for example, for treating a disease or disorder (e.g., described herein, such as PBA) in the subject.

The various aspects of transdermal delivery devices and formulations of the present disclosure can be combined in all possible combinations.

Methods of Administering Dextromethorphan and Treatment

In various embodiments, the present disclosure also provides a method of using the transdermal delivery device or pharmaceutical compositions described herein, for example, for administering dextromethorphan to a subject in need thereof, e.g., those suffering from any of the diseases or disorders described herein.

Some embodiments are directed to a method of administering dextromethorphan to a subject (e.g., human subject) in need thereof. In some embodiments, the subject is sensitive to or otherwise intolerant to CYP2D6 inhibitors such as quinidine, e.g., having one or more side effects associated with quinidine, and/or is co-administered (or in need of) a drug whose metabolism is affected by CYP2D6 inhibitors such as quinidine. In some embodiments, the subject is sensitive to or otherwise intolerant to quinidine, e.g., with QTc prolongation. In some embodiments, the method comprises applying any of the transdermal delivery devices (e.g., those shown in [18]-[35] in the Brief Summary section) or pharmaceutical compositions to the subject, for example, to the skin of the subject. In some embodiments, the subject is not administered dextromethorphan through another source, for example, through oral administration. However, in some embodiments, the subject can also be supplemented with another source of dextromethorphan, for example, by co-administering an oral formulation of dextromethorphan to the subject. In some embodiments, the subject does not suffer from a cough and/or does not need an antitussive. In some embodiments, the subject is characterized as an extensive metabolizer. In some embodiments, the subject is characterized as a poor metabolizer. In some embodiments, the subject is not co-administered a CYP2D6 inhibitor. In some embodiments, the subject is not co-administered quinidine. In some embodiments, the subject is co-administered a CYP2D6 inhibitor such as quinidine, bupropion, etc.

Various dosing regimen are suitable for the methods herein. For example, in some embodiments, the method comprises administering a transdermal delivery device (e.g., described herein, such as those shown in [18]-[35] in the Brief Summary section) to the subject once daily (e.g., replaced every 24 hours) for a desired period of time. In some embodiments, the transdermal delivery device comprises about 5 mg to about 100 mg of dextromethorphan. In some embodiments, the method can also comprise administering a transdermal delivery device (e.g., described herein) to the subject once in two days or more (e.g., once in two days, once in three days, once in four days, once in five days, once in six days, once in a week, etc.) for a desired period of time. In some embodiments, the method can also comprise administering a transdermal delivery device (e.g., described herein) to the subject once in at least one day, for example, once in two days or more (e.g., once a week), or 1, 2, 3, 4, 5, or 6 times a week for a desired period of time. In some embodiments, the method can also comprise administering a transdermal delivery device (e.g., described herein, such as those shown in [18]-[35] in the Brief Summary section) to the subject once a week. In some embodiments, the transdermal delivery device comprises about 50 mg to about 700 mg of dextromethorphan. While the methods herein typically apply the transdermal delivery device to the subject in a frequency of once a day or once in more than 1 day, in some embodiments, the methods can also apply the transdermal delivery device to the subject in a frequency of once in less than 1 day, such as twice a day or three times a day. For the avoidance of doubt, when it is said that the transdermal delivery device is applied to a subject once a day, it should mean that each application of the transdermal delivery device has a duration of about 24 hours or that it is replaced every 24 hours for the treatment period. Similarly, when it is said that the transdermal delivery device is applied to a subject once a week, it should mean that each application of the transdermal delivery device has a duration of about 1 week or that it is replaced every week for the treatment period. Other expressions should be understood similarly.

The methods of administering dextromethorphan herein typically provide certain pharmacokinetic profile in a subject (e.g., human subject) in need thereof that is suitable (e.g., effective), for example, for treating a disease or disorder (e.g., any of those described herein such as PBA) in the subject. PCT/US2018/054178 describes some of such pharmacokinetic profile, examples are shown in embodiments B1, B3-7, B9, B11-21, and B15-18 in the Exemplary embodiments section. Additional pharmacokinetic profiles are described herein, see e.g., [46]-[62] in the Brief Summary Section.

The methods herein are not limited to a particular subject or a particular class of subjects. In some embodiments, the subject is characterized as an extensive metabolizer. In some embodiments, the subject is characterized as a poor metabolizer. In some embodiments, the subject is not co-administered a CYP2D6 inhibitor. In some embodiments, the subject is not co-administered quinidine. In some embodiments, the subject is co-administered a CYP2D6 inhibitor such as quinidine, bupropion, etc. However, in any of the embodiments described herein, the subject does not suffer from a cough and/or does not need an antitussive.

In some embodiments, the subject (e.g., human subject) is characterized as having a neurological disease or disorder. In some embodiments, the subject (e.g., human subject) is characterized as having one or more diseases or disorders selected from affective disorders, psychiatric disorders, cerebral function disorders, movement disorders, dementias, motor neuron diseases, neurodegenerative diseases, seizure disorders, and headaches. In some embodiments, the subject suffers from one or more diseases or disorders selected from depression, major depressive disorder, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability. In some embodiments, the subject suffers from one or more diseases or disorders selected from Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia. In any of the embodiments herein, the subject can suffer from pseudobulbar affect, depression (e.g., major depressive disorder or treatment resistant depression), stroke, traumatic brain injury, seizure, pain (e.g., post-operative pain, neuropathic pain), methotrexate neurotoxicity, Parkinson's disease, autism, or combinations thereof. In any of the embodiments herein, the subject can suffer from pseudobulbar affect.

Methods of Treatment

Dextromethorphan are known to be useful for treating a variety of diseases or disorders. See e.g., Nguyen, L. et al., *Pharmacology & Therapeutics* 159:1022 (2016). Thus, in some embodiments, the present disclosure is also directed to a method of treating a disease or disorder in a subject in need thereof, for which administering dextromethorphan is beneficial. In some embodiments, the method comprises transdermally administering to the subject a therapeutically effective amount of dextromethorphan. In some embodiments, the administering comprises applying the transdermal delivery device (e.g., described herein, such as those shown in [18]-[35] in the Brief Summary section) to the skin of the subject. In some embodiments, the administering results in a PK profile described herein (e.g., as shown in [46]-in the Brief Summary section). In some embodiments, the subject does not suffer from a cough and/or does not need an antitussive agent. In some embodiments, the subject is an extensive metabolizer of dextromethorphan. In some embodiments, the subject is a poor metabolizer of dextromethorphan. In some embodiments, the subject is sensitive or intolerant to CYP2D6 inhibitors. In some embodiments, the subject is sensitive to or otherwise intolerant to quinidine, e.g., with QTc prolongation. In some embodiments, the subject has one or more side effects associated with quinidine. In some embodiments, the subject is co-administered (or in need of) a drug whose metabolism is affected by a CYP2D6 inhibitor.

Various diseases and disorders are suitable to be treated by the methods herein. In some embodiments, the disease or disorder is a neurological disorder. Non-limiting exemplary neurological diseases or disorders include affective disorders, psychiatric disorders, cerebral function disorders, movement disorders, dementias, motor neuron diseases, neurodegenerative diseases, seizure disorders, and headaches.

Affective disorders that can be treated by methods herein include, but are not limited to, depression, major depressive disorder, treatment resistant depression and treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Psychiatric disorders that can be treated by the methods herein include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease.

Substance addiction abuse that can be treated by the methods herein include, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

Cerebral function disorders that can be treated by the methods herein include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Movement disorders that can be treated by the methods herein include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that can be treated by the methods herein include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that can be treated by the methods herein include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that can be treated by the methods herein include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that can be treated by the methods herein include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that can be treated by the methods herein include, but are not limited to, migraine, tension, and cluster headaches.

Other neurological disorders that can be treated by the methods herein include, but are not limited to, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the disease or disorder is pain, joint pain, pain associated with sickle cell disease, pseudobulbar affect, depression (including major depressive disorder, treatment resistant depression, etc.), disorders related to memory and cognition, schizophrenia, Parkinson's disease, amyotrophic lateral sclerosis (ALS), Rhett's syndrome, seizures, cough (including chronic cough), etc.

The methods herein can also be used to treat, or provide relief to, any type of pain including, but not limited to, musculoskeletal pain, neuropathic pain, cancer-related pain, acute pain, nociceptive pain, inflammatory pain, arthritis pain, complex regional pain syndrome, etc.

In some embodiments, the disease or disorder can be allodynia, treatment refractory hyperalgesia, dermatitis, pain, inflammation or inflammatory conditions, such as Crohn's disease, including pain associated with inflammation, psoriasis, cancer, viral infection, or as an adjuvant treatment for multiple myeloma.

In any of the embodiments described herein, the method can be for treating pseudobulbar affect, depression (e.g., major depressive disorder, treatment resistant depression, etc.), stroke, traumatic brain injury, seizure, pain (e.g., post-operative pain, neuropathic pain), methotrexate neurotoxicity, Parkinson's disease, autism, or a combination thereof.

Suitable dosing regimen, dosing amount, duration, transdermal delivery devices, etc. include any of those described herein in any combination. In any of the embodiments described herein, the subject can be a human subject.

In some specific embodiments, the present disclosure provides a method of treating pseudobulbar affect comprising applying the transdermal delivery device herein (e.g., those shown in [18]-[35] in the Brief Summary section) to a subject in need thereof. In some embodiments, the transdermal delivery device comprises about 5 mg to about 100 mg of dextromethorphan. In some embodiments, the transdermal delivery device is applied once daily, e.g., for a period of time up to 7 days, at least 7 days, 1 month, or any period of time desired. In some embodiments, the transdermal delivery device comprises about 50 mg to about 700 mg of dextromethorphan. In some embodiments, the transdermal delivery device is applied once a week, e.g., for 1 week, 1 month, or any period of time desired. In some embodiments, the transdermal delivery device is applied 1, 2, 3, 4, 5, or 6 times in a week, e.g., for 1 week, 1 month, or any period of time desired. In some embodiments, the transdermal delivery device is applied to achieve any of the pharmacokinetic profile described herein (e.g., as shown in [46]-[62] in the Brief Summary section or those shown in embodiments B1, B3-7, B9, B11-21, and B15-18 in the Exemplary embodiments section). In some embodiments, the subject is not administered a CYP2D6 inhibitor. In some embodiments, the subject is not administered quinidine. In some embodiments, the subject does not suffer from a cough or need an antitussive effect. In some embodiments, the subject is characterized as a poor metabolizer. In some embodiments, the subject is characterized as an extensive metabolizer.

In some embodiments, the methods herein can further comprise administering to the subject an active agent other than dextromethorphan. For example, in some embodiments, the method described herein further comprises administering to the subject an antidepressant. In some embodiments, the antidepressant is selected from bupropion, hydroxybupropion, erythrohydroxybupropion, threohydroxybupropion, a metabolite or prodrug of any of these compounds, and combinations thereof. Other suitable antidepressants are described for example in U.S. Pat. No. 9,861,595, the content of which is incorporated by reference in its entirety. In some embodiments, the method described herein further comprises administering to the subject quinidine. In some embodiments, the method described herein further comprises administering to the subject a CYP2D6 inhibitor. In some embodiments, the method described herein further comprises administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof. These additional agents can be administered simultaneously or sequentially. Further, these additional agents can be administered via the same or a different route. For example, in some embodiments, the additional agent can be administered transdermally or orally. However, in some embodiments, the additional agent can also be combined with dextromethorphan in the same transdermal delivery device.

Because the transdermal application described herein bypasses the first-pass liver metabolism, the methods herein can provide dextromethorphan to subjects who are on medications that might interfere with liver metabolism of dextromethorphan. In some embodiments, the method comprises administering to the subject desipramine, paroxetine, thioridazine, pimozide, digoxin, atazanavir, clarithromycin, indinavir, itraconazole, ketoconazole, and combinations thereof. However, in some embodiments, the subject is not administered any of desipramine, paroxetine, thioridazine, pimozide, digoxin, atazanavir, clarithromycin, indinavir, itraconazole, ketoconazole, and combinations thereof. In some embodiments, the method does not require determining whether the subject is an extensive metabolizer or poor metabolizer of dextromethorphan.

Exemplary Methods

The present disclosure provides the following non-limiting exemplary methods of transdermally administering dextromethorphan.

Typically, the methods herein are for treating a disease or disorder where administering dextromethorphan is beneficial. Suitable diseases or disorders that can be treated with the methods herein are described herein. In some embodiments, the methods herein are for treating a neurological disease or disorder in a subject in need thereof. Such neurological diseases or disorders include but not limited affective disorders, psychiatric disorders, cerebral function disorders, movement disorders, dementias, motor neuron diseases, neurodegenerative diseases, seizure disorders, and headaches. In some embodiments, the methods are for treating pseudobulbar affect, depression (e.g., major depressive disorder or treatment resistant depression), stroke, traumatic brain injury, seizure, pain, methotrexate neurotoxicity, Parkinson's disease, autism, or a combination thereof. In some embodiments, the subject does not suffer from a cough and/or does not need an antitussive.

Nuedexta® tablets were approved by the FDA for treating pseudobulbar affect or PBA, see the Prescribing Information of Nuedexta®, June 2019 version, the content of which is herein incorporated by reference in its entirety. As stated in the Nuedexta Prescribing Information, PBA occurs secondary to a variety of otherwise unrelated neurologic conditions, and is characterized by involuntary, sudden, and frequent episodes of laughing and/or crying. PBA episodes typically occur out of proportion or incongruent to the underlying emotional state. PBA is a specific condition, distinct from other types of emotional lability that may occur in patients with neurological disease or injury.

In some specific embodiments, the methods herein are for treating PBA in a subject in need thereof. In some embodiments, the subject also suffers from a neurodegenerative disease such as amyotrophic lateral sclerosis, multiple sclerosis, Parkinson's disease, and/or Alzheimer's disease, stroke, or a brain injury, such as traumatic brain injury.

The methods herein typically comprise transdermally delivering to the subject in need thereof a therapeutically effective amount of dextromethorphan. In some embodiments, the method comprises transdermally delivering to the subject in need thereof a daily dose of about 15 mg to about 50 mg (e.g., about 15 mg, about 20 mg, about 30 mg, about 40 mg, about 50 mg, or any ranges between the recited values, such as about 20-50 mg, about 30-50 mg, or about 20-40 mg, etc.) of dextromethorphan. In some embodiments, the daily dose is about 20 mg to 40 mg of dextromethorphan, such as about 35 mg. In some embodiments, the daily dose can also be higher than 50 mg, such as about 60 mg, up to about 100 mg of dextromethorphan. In some embodiments, the daily dose can be lower than 15 mg, for example, about 5 mg, about 10 mg, or about 5-10 mg of dextromethorphan. The daily dose of dextromethorphan is typically delivered by applying a transdermal delivery device or patch or adhesive composition/formulation herein, e.g., any of those described herein (e.g, those shown in [18]-[35] in the Brief Summary section), to the subject.

In some embodiments, the daily dose of dextromethorphan is delivered to the subject by applying a transdermal delivery device comprising a drug-in-adhesive layer, wherein the drug-in-adhesive layer comprises dextromethorphan in an amount of about 2% to about 12%, preferably about 6% to about 12% (e.g., about 6%, about 7%, about 8%, about 9%, about 10%, about 11%, about 12%, or any ranges between the recited values, such as about 6-12%, 8-12% etc.) by weight, a pressure sensitive adhesive, and a skin permeation enhancer. The dextromethorphan and skin permeation enhancer are typically dispersed (e.g., homogeneously dispersed) in the pressure sensitive adhesive. In some embodiments, the dextromethorphan and skin permeation enhancer can be homogenously mixed with the pressure sensitive adhesive. In some embodiments, the drug-in-adhesive layer is a homogenous mixture. The pressure sensitive adhesive is typically an acrylate adhesive, e.g., a poly acrylate vinyl acetate copolymer, such as those having non-acidic hydroxyl functional groups, for example, described herein such as Duro-Tak 87-2287 adhesive and the alike. The pressure sensitive adhesive is typically present in an amount of about 65% to about 85% (e.g., about 65%, about 70%, about 75%, about 80%, or about 85%, by weight, or any ranges between the recited values, such as about 70-85%, about 75-85% etc.) by weight of the drug-in-adhesive layer. The skin permeation enhancer is typically isopropyl myristate. The skin permeation enhancer is typically present in an amount of about 6% to about 12% (e.g., about 6%, about 7%, about 8%, about 9%, about 10%, about 11%, about 12%, or any ranges between the recited values, such as about 8-12% etc.) by weight of the drug-in-adhesive layer. Preferably, the drug-in-adhesive layer further comprises a crystallization inhibitor, e.g., a vinylpyrrolidone polymer, such as vinyl pyrrolidone homopolymer (or povidone), for example, Povidone K30, Plasdone K29/32 and the alike. Preferably, the crystallization inhibitor is present in an amount of about 6% to about 12% (e.g., about 6%, about 7%, about 8%, about 9%, about 10%, about 11%, about 12%, or any ranges between the recited values, such as about 8-12% etc.) by weight of the drug-in-adhesive layer. As discussed herein, the inclusion of vinylpyrrolidone polymer can significantly enhance the dextromethorphan flux both in vitro and in vivo compared to an otherwise same patch without the vinylpyrrolidone polymer. The transdermal delivery device typically has an active surface area of about 30 $cm^2$ to about 100 $cm^2$, e.g., about 30 $cm^2$, about 40 $cm^2$, about 50 $cm^2$, about 60 $cm^2$, about 70 $cm^2$, about 80 $cm^2$, about 90 $cm^2$, about 100 $cm^2$, or any ranges between the recited values, such as about 40-60 $cm^2$, about 60-80 $cm^2$, etc.

The transdermal delivery device typically is configured to include a sufficient amount of dextromethorphan to deliver the desired daily dose. For example, in some embodiments, the transdermal delivery device has a total dextromethorphan loading of about 0.2 $mg/cm^2$ to about 5 $mg/cm^2$, such as about 0.2 $mg/cm^2$, about 0.3 $mg/cm^2$, about 0.4 $mg/cm^2$, about 0.5 $mg/cm^2$, about 0.6 $mg/cm^2$, about 0.7 $mg/cm^2$, about 0.8 $mg/cm^2$, about 0.9 $mg/cm^2$, about 1 $mg/cm^2$, about 2 $mg/cm^2$, about 5 $mg/cm^2$, or any ranges between the recited values, such as about 0.2-1 $mg/cm^2$, about 0.5-1 mg/cm$^2$, etc. Typically, the transdermal delivery device can be applied to the subject in need thereof once daily with the duration of each application of about 24 hours. For once daily dosing regimen, the total dextromethorphan loading can be typically in the lower range, such as about 0.2-1 mg/cm$^2$, about 0.5-1 mg/cm$^2$. In some embodiments, the transdermal delivery device can be applied to the subject in need thereof with a dosing frequency of once in more than a day, such as once in 1.5 days, 2 days, 3 days, 4 days, 5 days, or once a week, and in such embodiments, to deliver a desired daily dose, the transdermal delivery device can typically have a higher total dextromethorphan loading, such as about 1-5 mg/cm$^2$ or even higher than 5 mg/cm$^2$ and up to 8 mg/cm$^2$.

In some preferred embodiments, the transdermal delivery device is applied to the subject in need thereof once daily to deliver a daily dose of about 15 mg to 40 mg of dextromethorphan. Typically, the drug-in-adhesive layer of the transdermal delivery device includes about 20 mg to about 100 mg of dextromethorphan, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of dextromethorphan. In some embodiments, the daily dose is about 20 mg to 40 mg (such as about 35 mg) dextromethorphan, and the drug-in-adhesive layer comprises about 50 mg to about 70 mg of dextromethorphan, for example, about 56 mg of dextromethorphan. The drug-in-adhesive layer typically also include about 30 mg to about 100 mg of isopropyl myristate, e.g., about 30 mg, about 40 mg, about 50 mg, about 60 mg, about 70 mg, about 80 meg, about 90 mg, about 100 mg, or any ranges between the recited values, such as about 40-60 mg, 50-60 mg, or about 50-70 mg, etc. of isopropyl myristate. The pressure sensitive adhesive is typically included in the drug-in-adhesive layer in an amount of about 150 mg to about 900 mg, e.g., about 300 mg, about 350 mg, about 400 mg, about 450 mg, about 500 mg, about 550 mg, about 600 mg, about 700 mg, about 800 mg, about 900 mg, or any ranges between the recited values, such as about 300-500 mg, 350-450 mg, or about 300-550 mg, etc. In some embodiments, the crystallization inhibitor is preferably included in the drug-in-adhesive layer in an amount of about 30 mg to about 100 mg, e.g., in an amount of about 30 mg, about 40 mg, about 50 mg, about 60 mg, about 70 mg, about 80 mg, about 90 mg, about 100 mg, or any ranges between the recited values, such as about 40-60 mg, 50-60 mg, or about 50-70 mg, etc. While the ingredients of the drug-in-adhesive layer are described in ranges of absolute amounts, it should be understood that in some embodiments, the ingredients can have a relative weight percentage in the drug-in-adhesive layer as described herein. The dextromethorphan and isopropyl myristate are typically dispersed (e.g., homogeneously dispersed) in the pressure sensitive adhesive. In some embodiments, the dextromethorphan and isopropyl myristate are homogeneously mixed with the pressure sensitive adhesive. In some embodiments, the drug-in-adhesive layer is a homogenous mixture. The pressure sensitive adhesive is typically an acrylate adhesive, e.g., a poly acrylate vinyl acetate copolymer, such as those having non-acidic hydroxyl functional groups, for example, described herein such as Duro-Tak 87-2287 adhesive and the alike. The crystallization inhibitor is typically a vinylpyrrolidone polymer, such as vinyl pyrrolidone homopolymer (or povidone), for example, Povidone K30, Plasdone K29/32 and the alike. In some embodiments, the transdermal delivery device has an active surface area of about 30 cm$^2$ to about 100 cm$^2$, e.g., about 30 cm$^2$, about 40 cm$^2$, about 50 cm$^2$, about 60 cm$^2$, about 70 cm$^2$, about 80 cm$^2$, about 90 cm$^2$, about 100 cm$^2$, or any ranges between the recited values, such as about 40-60 cm$^2$, about 60-80 cm$^2$, etc. In some embodiments, the transdermal delivery device has about 50-70 mg of dextromethorphan and an active surface area of about 60-80 cm$^2$, such as about 70 cm$^2$. In some embodiments, the transdermal delivery device has about 56 mg of dextromethorphan and an active surface area of about 70 cm$^2$.

The transdermal delivery device herein typically has a dextromethorphan flux of at least about 200 ug/cm$^2$/day, when measured in vitro using human cadaver skin, such as about 200 ug/cm$^2$/day, about 300 ug/cm$^2$/day, about 400 ug/cm$^2$/day, about 500 ug/cm$^2$/day, about 600 ug/cm$^2$/day, about 700 ug/cm$^2$/day, about 800 ug/cm$^2$/day, about 1000 ug/cm$^2$/day, or any ranges between the recited values, such as about 200-800 ug/cm$^2$/day, about 300-800 ug/cm$^2$/day, about 400-800 ug/cm$^2$/day, about 500-800 ug/cm$^2$/day, etc. In some embodiments, the transdermal delivery devices herein comprises a vinylpyrrolidone polymer in the drug-in-adhesive layer in an amount of about 6% to about 12% (e.g., about 10%) by weight, such as a vinyl pyrrolidone homopolymer (or povidone), for example, Povidone K30, Plasdone K29/32 and the alike, and the transdermal delivery device can typically have a dextromethorphan flux, for example, about 400-800 ug/cm$^2$/day or about 500-800 ug/cm$^2$/day when measured in vitro using human cadaver skin.

In some preferred embodiments, the methods herein can be characterized as having a high transdermal bioavailability (i.e., the delivered dextromethorphan divided by initial dextromethorphan in the patch). For example, as shown in Example 4B, the initial (i.e., prior to application) dextromethorphan amount in an exemplary patch (containing Plasdone K29/32) is about 56 mg, and applying the exemplary patch to the subjects for 24 hours delivered about 32.4 mg to about 41.1 mg of dextromethorphan to the subjects, thus, the transdermal bioavailability from the patch is about 58% (32.4/56) to about 73% (41.1/56). This high percentage of delivery is made possible in part due to the unexpected discovery that it is possible to achieve continuously high flux of dextromethorphan from the transdermal patches herein. In some embodiments of the methods herein, the transdermal delivery device or patch (e.g., described herein) is applied to the subject once a day, and the residue amount of dextromethorphan in the transdermal delivery device or patch, i.e., the device or patch removed after being worn for about 24 hours, is less than 50% (e.g., less than 40%) of the initial dextromethorphan amount in the transdermal delivery device or patch. In some embodiments, the transdermal delivery device or patch is applied once a day, and the percentage of dextromethorphan delivered to the subject is about 50% to about 80% of the initial dextromethorphan amount in the transdermal delivery device or patch. In some embodiments, the transdermal delivery device or patch is applied once in more than a day, such as once in 1.5 days, 2 days, 3 days, or a week, and the residue amount of dextromethorphan in the transdermal delivery device or patch is less than the desired daily dose delivered to the subject, for example, less than 90% (e.g., less than 80%, or less than 60%). In some embodiments, the transdermal delivery device or patch is applied once in 1.5 days, 2 days, 3 days, or a week, and the percentage of dextromethorphan delivered to the subject is about 60% to about 90% of the initial dextromethorphan amount in the transdermal delivery device or patch. Typically, the transdermal delivery device or patch comprises a drug-in-adhesive layer which comprises (1) dextromethorphan in an amount of about 6% to about 12% (e.g., described herein, such as about 10%) by weight; (2) a poly acrylate vinyl acetate copolymer pressure sensitive adhesive, such as those having non-acidic hydroxyl functional groups, for example, described herein such as Duro-Tak 87-2287 adhesive and the alike, in an amount of about 65% to about 85% (e.g., described herein, such as about 70%) by weight; (3) isopropyl myristate in an amount of about 6% to about 12% (e.g., described herein, such as about 10%) by weight; and (4) a vinylpyrrolidone polymer, such as vinyl pyrrolidone homopolymer (or povidone), for example, Povidone K30, Plasdone K29/32 and the like, in an amount of about 6% to about 12% (e.g., described herein, such as about 10%) by weight. For a once daily dosing regimen, the transdermal delivery device or patch typically comprises about 30 mg to about 100 mg dextromethorphan with a patch size of about 30 $cm^2$ to about 100 $cm^2$.

In some embodiments, the methods herein can also be characterized by a unique in vivo pharmacokinetic (PK) profile described herein. As shown in more details in the Examples section, applying an exemplary patch to human subjects once daily provided a therapeutically effective plasma concentrations for a sustained period of time. Treatment of the diseases or disorders herein with the novel PK profiles described herein is by itself a novel feature of the present disclosure. These unique PK profiles provide many advantages, which include but not limited to a more accurate dosing, less frequent dosing, reduced potential for side effects associated with quinidine and/or higher exposure (e.g., $C_{max}$) of dextromethorphan, reduced pill burden, and better patient compliance.

Some embodiments of the methods herein are directed to the novel PK profile described herein. As would be understood by those skilled in the art, although the present disclosure focuses primarily on transdermal delivery of dextromethorphan, other delivery routes that by-pass the first-pass metabolism and deliver, such as continuously or substantially continuously deliver, dextromethorphan to the subject can achieve similar PK profiles. Accordingly, the present disclosure also specifically contemplates such methods of delivering dextromethorphan, which for example can include administering dextromethorphan intravenously, subcutaneously, intramuscularly, or via a depot.

In some embodiments, the present disclosure provides a method of treating a neurological disease or disorder (e.g., any of those described herein such as PBA) in a subject in need thereof, the method comprising applying a transdermal patch to the subject at a dosing frequency of once a day to once a week, wherein the transdermal patch comprises about 15 mg to about 700 mg (e.g., about 15 mg, about 30 mg, about 50 mg, about 75 mg, about 100 mg, about 150 mg, about 200 mg, about 300 mg, about 400 mg, about 500 mg, about 600 mg, about 700 mg, or any ranges between the recited values, such as about 15-100 mg, about 30-100 mg, about 30-75 mg, or about 150-500 mg, etc.) of dextromethorphan, and wherein the applying results in a therapeutically effective plasma concentration of dextromethorphan in the subject at steady state. In some embodiments, the transdermal patch comprises about 30 mg to about 100 mg of dextromethorphan. In some embodiments, the dosing frequency is once a day.

In some embodiments, the method is characterized by the PK profile resulted from the application of the transdermal patch. For example, in some embodiments, the present disclosure provides a method of treating a neurological disease or disorder (e.g., any of those described herein such as PBA) in a subject in need thereof, the method comprises applying a transdermal patch comprising about 30 mg to about 100 mg of dextromethorphan to the subject, preferably once daily, to deliver a daily dose of about 15 mg to about 50 mg of dextromethorphan, and the applying results in a pharmacokinetic profile in the subject characterized by one or more of the following:

a) an $AUC_{0\text{-}24,\ DXM}$ at day-7 or steady state stage between about 180 h*ng/ml to about 2000 h*ng/mL, for example, about 200 h*ng/mL to about 600 h*ng/ml or about 300 h*ng/mL to about 500 h*ng/ml;

b) a $C_{Avg,\ DXM}$ at day-7 or steady state stage between about 8 ng/ml to about 100 ng/mL, e.g., about 10 ng/ml to about 20 ng/mL, such as about 15 ng/ml;

c) a $C_{min,\ DXM}$ at day-7 or steady state stage between about 6 ng/ml to about 65 ng/ml, e.g., about 6 ng/mL to about 20 ng/ml;

d) a $C_{max,\ DXM}$ at day-7 or steady state stage between about 8 ng/ml to about 90 ng/ml, e.g., about 10 ng/ml to about 30 ng/ml;

e) a degree of fluctuation $[(C_{max}-C_{min})/C_{avg}]$ for dextromethorphan at day-7 or steady state stage between about 0.18 to about 0.8, e.g., about 0.18 to about 0.8, such as about 0.3 to about 0.5;

f) a swing $[(C_{max}-C_{min})/C_{min}]$ for dextromethorphan at day-7 or steady state stage between about 0.2 to about 1.35, e.g., about 0.3 to about 1, such as about 0.4 to 0.7;

g) a ratio of $AUC_{0\text{-}24,\ DXM}$ at steady state stage to $AUC_{0\text{-}24,\ DXM,\ D1}$ about 1.5 to about 5, e.g., about 1.5 to about 3, such as about 1.5-2.5;

h) a ratio of $AUC_{0\text{-}24,\ DXM}$ to $AUC_{0\text{-}24,\ DOR}$ at steady state stage of about 12 to about 35;

i) a ratio of $C_{max,\ DXM}$ to $C_{max,\ DOR}$ at steady state stage of about 12 to about 35; and j) a ratio of $C_{Avg,\ DXM}$ to $C_{Avg,\ DOR}$ at steady state stage of about 12 to about 35.

It should be understood that the dextrophan (Dor) concentrations and related parameters are based on free dextrophan, i.e., not conjugated. In some embodiments, the applying results in a pharmacokinetic profile in the subject characterized a) an $AUC_{0\text{-}24,\ DXM}$ at day-7 or steady state stage between about 200 h*ng/mL to about 600 h*ng/ml; b) a $C_{Avg,\ DXM}$ at day-7 or steady state stage about 10 ng/mL to about 20 ng/mL, such as about 15 ng/ml; c) a $C_{min,\ DXM}$ at day-7 or steady state stage between about 6 ng/mL to about 20 ng/ml; and/or d) a $C_{max,\ DXM}$ at day-7 or steady state stage between about 10 ng/mL to about 30 ng/mL. These levels of dextromethorphan exposure can be advantageous. As shown in Example 4B, at day-7 or steady state following oral administration of Nuedexta® tablets twice a day, the dextromethorphan plasma concentration were much higher than those described above. Thus, it is expected that the methods herein would at least produce a reduced incidence of side effects associated with high exposure (e.g., $C_{max}$, AUC, etc.) of dextromethorphan. In some embodiments, the applying results in a pharmacokinetic profile in the subject characterized by e) a degree of fluctuation $[(C_{max}-C_{min})/C_{avg}]$ for dextromethorphan at day-7 or steady state stage between about 0.18 to about 1; and/or f) a swing $[(C_{max}-C_{min})/C_{min}]$ for dextromethorphan at day-7 or steady state stage between about 0.3 to about 1. In some embodiments, the applying results in a pharmacokinetic profile in the subject characterized by g) a ratio of $AUC_{0\text{-}24,\ DXM}$ at steady state stage to $AUC_{0\text{-}24,\ DXM,\ D1}$ about 1.5 to about 3. In some embodiments, the applying results in a pharmacokinetic profile in the subject characterized by h) a ratio of $AUC_{0\text{-}24,\ DXM}$ to $AUC_{0\text{-}24,\ DOR}$ at steady state stage of about 12 to about 35; i) a ratio of $C_{max,\ DXM}$ to $C_{max,\ DOR}$ at steady state stage of about 12 to about 35; and/or j) a ratio of $C_{Avg,\ DXM}$ to $C_{Avg,\ DOR}$ at steady state stage of about 12 to about 35. Typically, for each application of the transdermal patch other than the first dose, the pre-dosing plasma concentration of dextromethorphan does not go below about 20% of the average concentration ($C_{Avg,\ DXM}$) observed from the immediate previous dose, for example, the pre-dosing concentration of the $2^{nd}$ dose does not go below about 20% of the average concentration observed from the $1^{st}$ dose. In some embodiments, the accumulation factor of dextromethorphan ranges from about 1 to about 5, e.g., about 1.2 to about 3, wherein the subject is an extensive metabolizer or ultra-extensive metabolizer. In some embodiments, the applying results in a pharmacokinetic profile in the subject characterized by k) a half-life of dextromethorphan at steady state stage between about 11 to about 29 hours, e.g., about 11 to about 24 hours, such as about 17 hours, in an extensive metabolizer or ultra-extensive metabolizer; and/or l) an Apparent first-order terminal disposition rate constant ($\lambda_z$) following the last dose after achieving steady state stage between about 0.018 $h^{-1}$ to about 0.065 $h^{-1}$, e.g., about 0.020 $h^{-1}$ to about 0.06 $h^{-1}$, in an extensive metabolizer or ultra-extensive metabolizer. The PK profile described hereinabove is suitable for treating various neurological diseases or disorders. In some embodiments, the neurological disease or disorder is pseudobulbar affect, depression (e.g., major depressive disorder or treatment resistant depression), stroke, traumatic brain injury, seizure, pain, methotrexate neurotoxicity, Parkinson's disease, autism, or a combination thereof. In some embodiments, the neurological disease or disorder is pseudobulbar affect. In some embodiments, the subject does not suffer from a cough and/or does not need an antitussive. Suitable patches that can be used to provide the PK profile include any of those described herein (e.g., those shown in [18]-[35] in the Brief Summary section). Those skilled in the art could select or design appropriate patches for achieving the PK profile described herein in view of the teachings of the present disclosure. For example, by choosing patches with appropriate dextromethorphan flux rate and daily dose, such as those similar to the exemplary patch shown in Example 4B, those skilled in the art could achieve the PK profiles described herein.

In some embodiments, the methods herein can be particularly useful and advantageous for treating certain subjects. Patients having neurological disorder(s) often have multiple comorbidities and/or are being treated with numerous other medications. For example, the clinical trials (controlled or uncontrolled) conducted for PBA were based on patient population having also Amyotrophic lateral sclerosis (ALS), Multiple sclerosis (MS) and a variety of other underlying neurological conditions including stroke and traumatic brain injury. Thus, patients having PBA are typically also treated with other medications such as medications for treating ALS, MS, stroke, and traumatic brain injury, etc. The use of Nuedexta® tablets, or similar strategies of using a CYP2D6 inhibitor to enhance dextromethorphan plasma concentration, is limited and may cause various restrictions and drug-drug interactions for such patients. Some of the side effects or drugs that are affected by a CYP2D6 inhibitor are described in the Prescribing Information of Nuedexta®, June 2019 version, the content of which is herein incorporated by reference in its entirety. For example, the Prescribing Information of Nuedexta® describes the following contraindications: 1) Patients with a history of quinidine, quinine or mefloquine-induced thrombocytopenia, hepatitis, or other hypersensitivity reactions such as bone marrow depression or lupus-like syndrome; 2) Patients with known hypersensitivity to dextromethorphan; 3) Use with an MAOI or within 14 days of stopping an MAOI. Allow 14 days after stopping NUEDEXTA before starting an MAOI; 4) Prolonged QT interval, congenital long QT syndrome, history suggestive of torsades de pointes, or heart failure; 5) Complete atrioventricular (AV) block without implanted pacemaker, or patients at high risk of complete AV block; and 6) Concomitant use with drugs that both prolong QT interval and are metabolized by CYP2D6 (e.g., thioridazine or pimozide). The Prescribing Information of Nuedexta® also describes various warnings and precautions including a) thrombocytopenia or other hypersensitivity reactions; b) Hepatitis; c) QT prolongation; d) Left ventricular hypertrophy (LVH) or left ventricular dysfunction (LVD); e) CYP2D6 substrate; f) dizziness; g) serotonin syndrome; and h) anticholinergic effects of quinidine. Many of these contraindications, warnings and precautions are associated with quinidine. For example, the Prescribing Information of Nuedexta® describes that "Quinidine can cause immune-mediated thrombocytopenia that can be severe or fatal"; "Quinidine has also been associated with a lupus-like syndrome involving polyarthritis"; "Other associations include rash, bronchospasm, lymphadenopathy, hemolytic anemia, vasculitis, uveitis, angioedema, agranulocytosis, the sicca syndrome, myalgia, elevation in serum levels of skeletal-muscle enzymes, and pneumonitis"; "Hepatitis, including granulomatous hepatitis, has been reported in patients receiving quinidine;" quinidine can also cause "accumulation of parent drug and/or failure of active metabolite formation may decrease the safety and/or the efficacy of drugs used concomitantly with NUEDEXTA that are metabolized by CYP2D6"; "potentially fatal cardiac arrhythmia, including torsades de pointes, can occur at quinidine exposures that are possible from NUEDEXTA overdose". Chronic quinidine toxicity may be possible with NUEDEXTA treatment. Further, a variety of drug s can have an effect on the pharmacological effect of quinidine, such as CYP3A4 Inhibitor, P-glycoprotein blocker, drugs have direct effects on QTc or are arrhythmogenic themselves, low serum potassium or moderately low potassium levels in association with diuretics, which can restrict the use of NUEDEXTA. Because quinidine inhibits CYP2D6, a variety of drug-drug interaction is also possible for CYP2D6 substrates such as desipramine, paroxetine. As described in the Prescribing Information of Nuedexta®, "in cases of prodrugs whose actions are mediated by the CYP2D6-produced metabolites (for example, codeine and hydrocodone, whose analgesic and antitussive effects appear to be mediated by morphine and hydromorphone, respectively), it may not be possible to achieve the desired clinical benefits in the presence of NUEDEXTA due to quinidine-mediated inhibition of CYP2D6." Quinidine is also an inhibitor of p-glycoprotein, which can significantly affect the plasma level of drugs that are p-glycoprotein substrates, such as digoxine. In sum, because of the various potential side effects associated with quinidine, there exists an unmet medical need, at least with respect to the treatment of PBA in patient populations that have one or more restrictions and/or side effects associated with quinidine or in general CYP2D6 inhibitors.

The transdermal delivery route described herein does not require the use of quinidine or other CYP2D6 inhibitors and thus can be advantageously used for treating patients without the restrictions associated with quinidine or CYP2D6 inhibitors. For example, in some embodiments, the methods herein can treat subjects that are sensitive or intolerant to quinidine or in general to CYP2D6 inhibitors. In some embodiments, the subject can be sensitive or intolerant to CYP2D6 inhibitors. In some embodiments, the subject can be sensitive or intolerant to quinidine. In some embodiments, the subject has one or more side effects associated with quinidine. In some embodiments, the subject is co-administered a drug whose metabolism is affected by a CYP2D6 inhibitor. In some embodiments, the subject is co-administered a drug whose metabolism is affected by quinidine. In some embodiments, the subject is co-administered a drug that can affect the pharmacological effect of quinidine, such as a CYP3A4 inhibitor (e.g., atazanavir, clarithromycin, indinavir, itraconazole, ketoconazole, nefazodone, nelfinavir, ritonavir, saquinavir, telithromycin, amprenavir, aprepitant, diltiazem, erythromycin, fluconazole, fosamprenavir, grapefruit juice, and verapamil). In some embodiments, the subject can be further treated with a Selective Serotonin Reuptake Inhibitor (such as fluoxetine), a tricyclic antidepressant (such as clomipramine and imipramine), and/or a monoamine oxidase inhibitor (MAOI).

Further, as the transdermal delivery route described herein does not require the use of quinidine or other CYP2D6 inhibitors, the transdermal delivery devices or formulations herein can be conveniently administered to transdermally deliver dextromethorphan to a subject with or without first determining whether the subject is a poor metabolizer, an intermediate metabolizer, or an extensive metabolizer of dextromethorphan. In a poor metabolizer, the addition of quinidine or other CYP2D6 inhibitors is not expected to have a significant effect on the plasma exposure of dextromethorphan, but such addition would nonetheless expose the subject to the potential side effects associated with quinidine or other CYP2D6 inhibitors. The transdermal delivery methods described herein do not suffer from such drawbacks. In some embodiments, the methods herein can treat a subject without first determining whether the subject is a poor metabolizer, an intermediate metabolizer, or an extensive metabolizer of dextromethorphan. In some embodiments, the method herein can treat a subject that is an extensive metabolizer. In some embodiments, the method herein can treat a subject that is a poor metabolizer. In some embodiments, the method herein can also comprise determining whether a subject is a poor metabolizer, an intermediate metabolizer, or an extensive metabolizer of dextromethorphan, and administering to the subject an appropriate daily dose of dextromethorphan to the subject. For example, in some embodiments, the daily dose can be adjusted such that the transdermal delivery results in a therapeutically effective plasma concentration of dextromethorphan in the subject. In some embodiments, the daily dose can be adjusted such that the transdermal delivery results in any of the PK profile described herein (e.g., those shown in [46]-[62] in the Brief Summary section). For example, in some embodiments, the present disclosure provides a method of treating a neurological disease or disorder (e.g., any of those described herein) in a subject in need thereof, the method comprising (a) applying a first transdermal patch (e.g., those shown in [18]-[35] in the Brief Summary Section) to the subject at a dosing frequency of once a day to once a week to deliver a first daily dose (typically about 15 mg to about 50 mg) of dextromethorphan to the subject; (b) determining whether the applying results in any of the pharmacokinetic profile disclosed herein (e.g., those shown in [46]-[62] in the Brief Summary section); and optionally (c) adjusting the first daily dose upper or lower such that the applying results in one or more of the pharmacokinetic profile disclosed herein (e.g., those shown in [46]-[62] in the Brief Summary section). Suitable transdermal patches and dosing regimens include any of those described herein.

As discussed herein, it is expected that the methods herein would at least produce a reduced incidence of side effects associated with high exposure (e.g., $C_{max}$, AUC, etc.) of dextromethorphan. Thus, in some embodiments, the methods herein can also be advantageously used to treat a subject who has one or more side effects associated with high exposure (e.g., $C_{max}$, AUC, etc.) of dextromethorphan.

The methods herein can be used in combination with other medications. For example, in some embodiments, the method can further comprise administering to the subject an antidepressant. In some embodiments, the antidepressant is bupropion, hydroxybupropion, erythrohydroxybupropion, threohydroxybupropion, a metabolite or prodrug of any of these compounds, and combinations thereof. In some embodiments, the method can further comprise administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof. Typically, the methods herein do not administer to the subject quinidine. However, in some embodiments, quinidine can also be administered. These additional agents can be administered simultaneously or sequentially. Further, these additional agents can be administered via the same or a different route. For example, in some embodiments, the additional agent can be administered transdermally or orally. However, in some embodiments, the additional agent can also be combined with dextromethorphan in the same transdermal delivery device.

Definitions

As used herein, the term "about" modifying an amount related to the invention refers to variation in the numerical quantity that can occur, for example, through routine testing and handling; through inadvertent error in such testing and handling; through differences in the manufacture, source, or purity of ingredients/materials employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the term "cumulative drug permeated" refers to the total amount of drug permeated per square centimeter during a given period of time. Unless otherwise obvious from context, "cumulative drug permeated" at a given time (e.g., at 24 hours post administration) refers to the total amount of drug permeated per square centimeter from time 0 (i.e., time of administration) to the given time. Unless otherwise obvious from context, "cumulative drug permeated" refers to the arithmetic mean value measured and/or calculated in accordance with the methods described herein. The term "mean value" as used herein, when not specified, also refers to arithmetic mean value, unless contradictory to common practice in the field.

As used herein, the term "flux" refers to the quantity of the drug permeated skin per unit area per unit time. Unless otherwise obvious from context, "flux" refers to the arithmetic mean value measured and/or calculated in accordance with the methods described herein. A typical unit of flux is milligram per square centimeter per hour or per day. Dextromethorphan flux per day as used herein should be understood as the arithmetic mean value of the cumulative dextromethorphan permeated at 24 hours post application, measured and/or calculated in accordance with the methods described herein.

Flux rate as referenced in this patent application can mean that measured by either in vivo or in vitro methods. One way to measure flux is to place the transdermal delivery device or formulation on a known skin area of a human volunteer and measure how much drug can permeate across skin within certain time constraints. Those skilled in the art would understand that in some cases, the absolute value of in vitro flux can be several fold different when measured using a different cadaver source. As used herein, when specifically referenced as measured by in vitro method using human cadaver skin, the flux rate should be understood as measured in accordance with the method described in Example 2. For example, a patch tested in Example 2 can be used as a reference patch, which when tested in a method in accordance with Example 2, should yield the same flux as observed in Example 2, within experimental error generally accepted by those skilled in the art. Although an in vitro method uses human epidermal membrane obtained from a cadaver, rather than measure drug flux across the skin using human volunteers, it is generally accepted by those skilled in the art that results from a properly designed and executed in vitro test can be used to estimate or predict the results of an in vivo test with reasonable reliability.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated.

The term "therapeutically effective amount," as used herein, refers to that amount of a therapeutic agent (e.g., dextromethorphan) sufficient to result in amelioration of one or more symptoms of a disorder or condition (e.g., PBA), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment.

As used herein, applying or administering the transdermal delivery device herein should be understood as in accordance with how such transdermal delivery device is normally applied or administered, e.g., to the skin of a human subject.

EXEMPLARY EMBODIMENTS

Exemplary Embodiments A1-55

The following shows non-limiting exemplary embodiments A1-55:

1. A transdermal delivery device comprising
   a. an adhesive layer comprising an adhesive, which optionally comprises dextromethorphan dispersed in the adhesive in an amount of about 2% to about 12% by weight of the adhesive layer; and optionally
   b. a reservoir layer comprising dextromethorphan in an amount of at least 10% (e.g., about 20% to about 60%) by weight of the reservoir layer.
2. The transdermal delivery device of embodiment A1, wherein the transdermal delivery device is configured to transdermally deliver dextromethorphan to a user about 2 mg/day to about 50 mg/day.
3. The transdermal delivery device of embodiment A1 or 2, wherein the transdermal delivery device is configured to transdermally deliver dextromethorphan to a user about 5 mg/day to about 50 mg/day (e.g., about 5 mg/day, about 10 mg/day, about 20 mg/day, about 30 mg/day, about 40 mg/day, about 50 mg/day, or any ranges between the recited values) for 1 day or more (e.g., 1.5 days, 2 days, 3 days, 4 days, 5 days, 6 days, 7 days, or any ranges between the recited values).
4. The transdermal delivery device of any one of embodiments A1-3, which has a total dextromethorphan loading of about 0.5 mg/cm$^2$ to about 8 mg/cm$^2$.
5. The transdermal delivery device of any one of embodiments A1-4, which has a total dextromethorphan loading of about 2 mg/cm$^2$ to about 6 mg/cm$^2$ (e.g., about 2 mg/cm$^2$, about 3 mg/cm$^2$, about 4 mg/cm$^2$, about 5 mg/cm$^2$, about 6 mg/cm$^2$, or any ranges between the recited values).
6. The transdermal delivery device of any one of embodiments A1-5, which has an active surface area of about 5 cm$^2$ to about 200 cm$^2$.
7. The transdermal delivery device of any one of embodiments A1-6, which has an active surface area of about 10 cm$^2$ to about 150 cm$^2$.
8. The transdermal delivery device of any one of embodiments A1-7, which has an active surface area of about 30 cm$^2$ to about 100 cm$^2$ (e.g., about 30 cm$^2$, about 40 cm$^2$, about 50 cm$^2$, about 60 cm$^2$, about 70 cm$^2$, about 80 cm$^2$, about 90 cm$^2$, about 100 cm$^2$, or any ranges between the recited values).
9. The transdermal delivery device of any one of embodiments A1-8, wherein the adhesive layer comprises dextromethorphan in an amount of about 6% to about 12% (e.g., about 6%, about 7%, about 8%, about 9%, about 10%, about 11%, about 12%, or any ranges between the recited values) by weight of the adhesive layer.
10. The transdermal delivery device of any one of embodiments A1-9, wherein the adhesive layer further comprises a skin permeation enhancer.
11. The transdermal delivery device of embodiment A10, wherein the skin permeation enhancer is selected from isopropyl myristate, oleyl oleate, oleic acid, glycerol monooleate, other fatty acids and fatty acid esters with carbon chain lengths of C12 to C18, and combinations thereof.
12. The transdermal delivery device of embodiment A10 or 11, wherein the skin permeation enhancer is present in an amount of about 2% to about 15% by weight of the adhesive layer.
13. The transdermal delivery device of any one of embodiments A10-12, wherein the skin permeation enhancer is present in an amount of about 6% to about 12% (e.g., about 6%, about 7%, about 8%, about 9%, about 10%, about 11%, about 12%, or any ranges between the recited values) by weight of the adhesive layer.
14. The transdermal delivery device of any one of embodiments A1-13, wherein the adhesive layer further comprises an agent to improve cohesive strength of the adhesive layer.
15. The transdermal delivery device of any one of embodiments A1-13, wherein the adhesive layer further comprises an agent selected from a vinylpyrrolidone polymer (e.g., a vinylpyrrolidone-vinyl acetate copolymers), Kollidon (e.g., Kollidon 30 LP, Kollidon 90, or Kollidon VA64), silicone dioxide, titanium dioxide, and combinations thereof.

16. The transdermal delivery device of embodiment A14 or 15, wherein the agent is present in an amount of about 1% to about 20% by weight of the adhesive layer.

17. The transdermal delivery device of any one of embodiments A14-16, wherein the agent is present in an amount of about 2% to about 20% (e.g., about 2%, about 2.5%, about 3%, about 4%, about 5%, about 6%, about 10%, about 15%, about 20%, or any ranges between the recited values), for example, about 2% to about 6% (e.g., about 2%, about 2.5%, about 3%, about 4%, about 5%, or any ranges between the recited values) by weight of the adhesive layer.

18. The transdermal delivery device of any one of embodiments A1-17, wherein the adhesive comprises a pressure sensitive adhesive.

19. The transdermal delivery device of embodiment A18, wherein the pressure sensitive adhesive comprises a polyisobutylene adhesive, a silicone polymer adhesive, an acrylate copolymer adhesive (e.g., a poly acrylate vinyl acetate copolymer, such as those having non-acidic hydroxyl functional groups, for example, described herein such as Duro-Tak 87-2287 adhesive and the alike), or a combination thereof.

20. The transdermal delivery device of embodiment A18 or 19, wherein the pressure sensitive adhesive is present in an amount of about 50% to about 90% by weight of the adhesive layer.

21. The transdermal delivery device of any one of embodiments A18-20, wherein the pressure sensitive adhesive is present in an amount of about 60% to about 85% (e.g., about 60%, about 70%, about 75%, about 80%, about 85%, or any ranges between the recited values) by weight of the adhesive layer.

22. The transdermal delivery device of any one of embodiments A1-21, wherein the adhesive layer is capable of adhering to a user's skin continuously for at least 1 day (e.g., at least 2 days, at least 3 days, at least 4 days, at least 5 days, at least 6 days, at least 7 days).

23. The transdermal delivery device of any one of embodiments A1-22, wherein the adhesive layer is about 0.1 mil to about 10 mils thick (e.g., about 0.5 mil to about 10 mils, about 1 mil to 10 mils).

24. The transdermal delivery device of any one of embodiments A1-23, wherein the reservoir layer comprises dextromethorphan in an amount of about 30% to about 50% (e.g., about 30%, about 35%, about 40%, about 45%, about 50%, or any ranges between the recited values) by weight of the reservoir layer.

25. The transdermal delivery device of any one of embodiments A1-24, wherein the reservoir layer further comprises a skin permeation enhancer.

26. The transdermal delivery device of embodiment A25, wherein the skin permeation enhancer is selected from isopropyl myristate, oleyl oleate, oleic acid, glycerol monooleate, other fatty acids and fatty acid esters with carbon chain lengths of C12 to C18, and combinations thereof.

27. The transdermal delivery device of embodiment A25 or 26, wherein the skin permeation enhancer is present in an amount of about 2% to about 15% by weight of the reservoir layer.

28. The transdermal delivery device of any one of embodiments A25-27, wherein the skin permeation enhancer is present in an amount of about 6% to about 12% (e.g., about 6%, about 7%, about 8%, about 9%, about 10%, about 11%, about 12%, or any ranges between the recited values) by weight of the reservoir layer.

29. The transdermal delivery device of any one of embodiments A1-28, wherein the reservoir layer further comprises an agent to improve cohesive strength of the reservoir layer.

30. The transdermal delivery device of any one of embodiments A1-28, wherein the reservoir layer further comprises an agent selected from a vinylpyrrolidone polymer (e.g., a vinylpyrrolidone-vinyl acetate copolymers), Kollidon (e.g., Kollidon 30 LP, Kollidon 90, or Kollidon VA64), silicone dioxide, titanium dioxide, and combinations thereof.

31. The transdermal delivery device of embodiment A29 or 30, wherein the agent is present in an amount of about 1% to about 20% by weight of the reservoir layer.

32. The transdermal delivery device of any one of embodiments A29-31, wherein the agent is present in an amount of about 2% to about 20% (e.g., about 2%, about 2.5%, about 3%, about 4%, about 5%, about 6%, about 10%, about 15%, about 20%, or any ranges between the recited values), for example, about 2% to about 6% (e.g., about 2%, about 2.5%, about 3%, about 4%, about 5%, or any ranges between the recited values) by weight of the reservoir layer.

33. The transdermal delivery device of any one of embodiments A1-32, wherein the reservoir layer comprises dextromethorphan dispersed, e.g., homogenously dispersed, in a pressure sensitive adhesive.

34. The transdermal delivery device of embodiment A33, wherein the pressure sensitive adhesive comprises a polyisobutylene adhesive, a silicone polymer adhesive, an acrylate copolymer adhesive (e.g., a poly acrylate vinyl acetate copolymer, such as those having non-acidic hydroxyl functional groups, for example, described herein such as Duro-Tak 87-2287 adhesive and the alike), or a combination thereof.

35. The transdermal delivery device of embodiment A33 or 34, wherein the pressure sensitive adhesive is present in an amount of about 20% to about 80% by weight of the reservoir layer.

36. The transdermal delivery device of any one of embodiments A33-35, wherein the pressure sensitive adhesive is present in an amount of about 20% to about 65% (e.g., about 20%, about 30%, about 35%, about 40%, about 50%, about 60%, about 65%, or any ranges between the recited values) by weight of the reservoir layer.

37. The transdermal delivery device of any one of embodiments A1-36, wherein the reservoir layer is about 0.1 mil to about 10 mils thick (e.g., about 0.5 mil to about 10 mils, about 1 mil to about 10 mils).

38. The transdermal delivery device of any one of embodiments A1-37, wherein the adhesive layer and reservoir layer are separated by a rate-controlling membrane.

39. A method of administering dextromethorphan to a subject in need thereof, the method comprising applying the transdermal delivery device/patch of any one of embodiments A1-38, C1-21, and those shown in [18]-[35] in the Brief Summary section to the subject, or the method comprising applying to the subject a transdermal delivery device comprising an adhesive layer having the same or substantially the same ingredients as in Formulation A, B, C1, C2, C3, D0, D1, D2, or E1 in the Examples.

40. The method of embodiment A39, wherein the subject does not suffer from a cough and/or does not need an antitussive.
41. The method of embodiment A39 or 40, wherein the subject is characterized as an extensive metabolizer.
42. The method of any one of embodiments A39-41, wherein the subject suffers from a neurological disease or disorder.
43. The method of any one of embodiments A39-41, wherein the subject suffers from one or more diseases or disorders selected from affective disorders, psychiatric disorders, cerebral function disorders, movement disorders, dementias, motor neuron diseases, neurodegenerative diseases, seizure disorders, and headaches.
44. The method of any one of embodiments A39-41, wherein the subject suffers from one or more diseases or disorders selected from depression, major depressive disorder, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.
45. The method of any one of embodiments A39-41, wherein the subject suffers from one or more diseases or disorders selected from Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.
46. The method of any one of embodiments A39-41, wherein the subject suffers from pseudobulbar affect, depression (e.g., major depressive disorder or treatment resistant depression), stroke, traumatic brain injury, seizure, pain (e.g., post-operative pain, neuropathic pain), methotrexate neurotoxicity, Parkinson's disease, autism, or combinations thereof.
47. The method of any one of embodiments A39-46, further comprising administering to the subject an antidepressant.
48. The method of embodiment A47, wherein the antidepressant is selected from bupropion, hydroxybupropion, erythrohydroxybupropion, threohydroxybupropion, a metabolite or prodrug of any of these compounds, and combinations thereof.
49. The method of any one of embodiments A39-46, further comprising administering to the subject quinidine.
50. The method of any one of embodiments A39-46, wherein the subject is not administered a CYP2D6 inhibitor.
51. The method of any one of embodiments A39-46, wherein the subject is not administered quinidine.
52. The method of any one of embodiments A39-46, wherein the subject is not administered any of desipramine, paroxetine, thioridazine, pimozide, digoxin, atazanavir, clarithromycin, indinavir, itraconazole, ketoconazole, and combinations thereof.
53. The method of any one of embodiments A39-46, further comprising administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof.
54. The method of any one of embodiments A39-53, wherein the transdermal delivery device is applied once daily, e.g., for a period of up to 7 days or more, or for at least 7 days or any desired period of time.
55. The method of any one of embodiments A39-53, wherein the transdermal delivery device is applied once a week or 2, 3, 4, 5, or 6 times a week.

Exemplary Embodiments B1-26

The following shows non-limiting exemplary embodiments B1-26:

1. A method of administering dextromethorphan to a human subject in need thereof, the method comprising applying a transdermal delivery device comprising dextromethorphan to the skin of the subject once daily, wherein the applying results in one or more of the following pharmacokinetic profile in the human subject:
   a. a mean $C_{max}$ of dextromethorphan of at least about 3 ng/ml (e.g., about 3 ng/ml to about 12 ng/ml) at day 1 post application;
   b. a mean $AUC_{0-24}$ of dextromethorphan of at least about 40 ng*h/ml (e.g., about 40 ng*h/ml to about 150 ng*h/ml) at day 1 post application;
   c. a mean ratio of $C_{24\ h}/C_{12\ h}$ of dextromethorphan of not more than about 1.5 (e.g., about 1 to about 1.5) at day 1 post application;
   d. a mean ratio of $C_{24\ h}/C_{6\ h}$ of dextromethorphan of at least about 1.2 (e.g., about 1.5 to about 2.5) at day 1 post application;
   e. a mean ratio of $C_{24\ h}/C_{18\ h}$ of dextromethorphan of about 0.85 to about 1.3 at day 1 post application;
   f. a mean $C_{max}$ of dextrorphan of not more than 2 ng/ml (e.g., not more than 2 ng/ml, not more than 1 ng/ml, or not more than 0.5 ng/ml) at day 1 post application;
   g. a mean $AUC_{0-24}$ of dextrorphan of not more than 10 ng*h/ml (e.g., not more than 10 ng*h/ml or not more than 5 ng*h/ml) at day 1 post application;
   h. a mean ratio of $C_{max}$ of dextromethorphan to $C_{max}$ of dextrophan of at least about 5 (e.g., at least about 10, at least about 15, at least about 20) at day 1 post application; and i. a mean ratio of $AUC_{0-24}$ of dextromethorphan to $AUC_{0-24}$ of dextrophan of at least about 5 (e.g., at least about 10, at least about 15, at least about 20, or at least about 25) at day 1 post application.

2. The method of embodiment B1, wherein the human subject does not suffer from a cough and/or does not need an antitussive.

3. The method of embodiment B1 or 2, wherein the human subject is characterized as an extensive metabolizer.

4. The method of any one of embodiments B1-3, wherein the applying results in a mean $C_{max}$ of dextromethorphan of at least about 30% (e.g., about 30% to about 80%) of that observed from orally administering a combination of 20 mg dextromethorphan and 10 mg quinidine twice a day to the human subject, when measured at day 1 post application.

5. The method of any one of embodiments B1-4, wherein the applying results in a mean $AUC_{0-24}$ of dextromethorphan of at least about 30% (e.g., about 30% to about 80%) of that observed from orally administering a combination of 20 mg dextromethorphan and 10 mg quinidine twice a day to the human subject, when measured at day 1 post application.

6. The method of any one of embodiments B1-5, wherein the applying results in a mean $C_{max}$ of dextrorphan of not more than about 50% (e.g., about 10% to about 30%) of that observed from orally administering a combination of 20 mg dextromethorphan and 10 mg quinidine twice a day to the human subject, when measured at day 1 post application.

7. The method of any one of embodiments B1-6, wherein the applying results in a mean $AUC_{0-24}$ of dextrorphan of not more than about 50% (e.g., about 10% to about 30%) of that observed from orally administering a combination of 20 mg dextromethorphan and 10 mg quinidine twice a day to the human subject, when measured at day 1 post application.

8. The method of any one of embodiments B1-7, wherein the human subject suffers from pseudobulbar affect, depression (e.g., major depressive disorder or treatment resistant depression), stroke, traumatic brain injury, seizure, pain (e.g., post-operative pain, neuropathic pain), methotrexate neurotoxicity, Parkinson's disease, autism, or a combination thereof.

9. The method of any one of embodiments B1-8, comprising applying the transdermal delivery device once a day for a period of time up to seven days or for at least 7 days or any desired period of time, wherein the applying results in one or both of the following pharmacokinetic profile in the human subject:

a. a mean $C_{max}$ of dextromethorphan of at least about 8 ng/ml (e.g., about 8 ng/ml to about 20 ng/ml) at day 7 post application; and b. a mean $C_{max}$ of dextrorphan of not more than 2 ng/ml (e.g., not more than 2 ng/ml, not more than 1 ng/ml, or not more than 0.5 ng/ml) at day 7 post application.

10. The method of any one of embodiments B1-9, wherein the transdermal delivery device comprises about 5 mg to about 100 mg of dextromethorphan.

11. A method of administering dextromethorphan to a human subject in need thereof, the method comprising applying a transdermal delivery device comprising dextromethorphan to the skin of the subject once a week or 2, 3, 4, 5, or 6 times a week, wherein the applying results in one or more of the following pharmacokinetic profile in the human subject:

a. a mean $C_{max}$ of dextromethorphan of at least about 3 ng/ml (e.g., about 3 ng/ml to about 12 ng/ml) at day 1 post application;

b. a mean $AUC_{0-24}$ of dextromethorphan of at least about 40 ng*h/ml (e.g., about 40 ng*h/ml to about 150 ng*h/ml) at day 1 post application;

c. a mean ratio of $C_{24\ h}/C_{12\ h}$ of dextromethorphan of not more than about 1.5 (e.g., about 1 to about 1.5) at day 1 post application;

d. a mean ratio of $C_{24\ h}/C_{6\ h}$ of dextromethorphan of at least about 1.2 (e.g., about 1.5 to about 2.5) at day 1 post application;

e. a mean ratio of $C_{24\ h}/C_{18\ h}$ of dextromethorphan of about 0.85 to about 1.3 at day 1 post application;

f. a mean $C_{max}$ of dextrorphan of not more than 2 ng/ml (e.g., not more than 2 ng/ml, not more than 1 ng/ml, or not more than 0.5 ng/ml) at day 1 post application;

g. a mean $AUC_{0-24}$ of dextrorphan of not more than 10 ng*h/ml (e.g., not more than 10 ng*h/ml or not more than 5 ng*h/ml) at day 1 post application;

h. a mean ratio of $C_{max}$ of dextromethorphan to $C_{max}$ of dextrophan of at least about 5 (e.g., at least about 10, at least about 15, at least about 20) at day 1 post application; and i. a mean ratio of $AUC_{0-24}$ of dextromethorphan to $AUC_{0-24}$ of dextrophan of at least about 5 (e.g., at least about 10, at least about 15, at least about 20, or at least about 25) at day 1 post application.

12. The method of embodiment B11, wherein the applying further results in one or both of the following pharmacokinetic profile in the human subject:

a. a mean $C_{max}$ of dextromethorphan of at least about 8 ng/ml (e.g., about 8 ng/ml to about 20 ng/ml) at day 7 post application; and b. a mean $C_{max}$ of dextrorphan of not more than 2 ng/ml (e.g., not more than 2 ng/ml, not more than 1 ng/ml, or not more than 0.5 ng/ml) at day 7 post application.

13. The method of embodiment B11 or 12, wherein the human subject does not suffer from a cough and/or does not need an antitussive.

14. The method of any one of embodiments B11-13, wherein the human subject is characterized as an extensive metabolizer.

15. The method of any one of embodiments B11-14, wherein the applying results in a mean $C_{max}$ of dextromethorphan of at least about 30% (e.g., about 30% to about 80%) of that observed from orally administering a combination of 20 mg dextromethorphan and 10 mg quinidine twice a day to the human subject for 7 days, when measured at day 7 post application.

16. The method of any one of embodiments B11-15, wherein the applying results in a mean $AUC_{0-24}$ of dextromethorphan of at least about 30% (e.g., about 30% to about 80%) of that observed from orally administering a combination of 20 mg dextromethorphan and 10 mg quinidine twice a day to the human subject for 7 days, when measured at day 7 post application.

17. The method of any one of embodiments B11-16, wherein the applying results in a mean $C_{max}$ of dextrorphan of not more than about 50% (e.g., about 10% to about 30%) of that observed from orally administering a combination of 20 mg dextromethorphan and 10 mg quinidine twice a day to the human subject for 7 days, when measured at day 7 post application.

18. The method of any one of embodiments B11-17, wherein the applying results in a mean $AUC_{0-24}$ of dextrorphan of not more than about 50% (e.g., about 10% to about 30%) of that observed from orally administering a combination of 20 mg dextromethorphan and 10 mg quinidine twice a day to the human subject for 7 days, when measured at day 7 post application.

19. The method of any one of embodiments B11-18, wherein the human subject suffers from pseudobulbar affect.
20. The method of any one of embodiments B11-19, wherein the transdermal delivery device comprises about 50 mg to about 700 mg of dextromethorphan.
21. A method of treating a disease or disorder in a subject in need thereof, the method comprising administering a transdermal delivery device comprising dextromethorphan to the skin of the subject once daily, wherein the applying results in one or more of the pharmacokinetic profile recited in embodiments B1, B3-7 and B9, wherein the disease or disorder is any of those described herein.
22. The method of embodiment B21, wherein the disease or disorder is a neurological disease or disorder, e.g., pseudobulbar affect.
23. A method of treating a disease or disorder in a subject in need thereof, the method comprising administering a transdermal delivery device comprising dextromethorphan to the skin of the subject once a week or 2, 3, 4, 5, or 6 times a week, wherein the applying results in one or more of the pharmacokinetic profile recited in embodiments B11-12 and B15-18, wherein the disease or disorder is any of those described herein.
24. The method of embodiment 21, wherein the disease or disorder is a neurological disease or disorder, e.g., pseudobulbar affect.
25. The method of any one of embodiments B1-24, wherein the transdermal delivery device is selected from the transdermal delivery device of any of embodiments A1-38, C1-21, and those shown in [18]-[35] in the Brief Summary section.
26. The method of any one of embodiments B1-24, wherein the transdermal delivery device comprises an adhesive layer having the same or substantially the same ingredients as in Formulation A, B, C1, C2, C3, D0, D1, D2, or E1 in the Examples.

Exemplary Embodiments C1-32

The following shows non-limiting exemplary embodiments C1-32:

1. A transdermal delivery device comprising:
   an adhesive layer comprising dextromethorphan dispersed in an adhesive comprising an acrylate adhesive and a silicone adhesive,
   wherein the weight ratio of the acrylate adhesive to silicon adhesive ranges from about 20:1 to about 1:20.
2. The transdermal delivery device of embodiment C1, wherein the weight ratio of the acrylate adhesive to silicon adhesive ranges from about 10:1 to about 1:10 (e.g., about 10:1, about 4:1, about 1:1, about 1:4, or any ranges between the recited value).
3. The transdermal delivery device of embodiment C1 or 2, which is configured to provide a mean cumulative dextromethorphan permeated of at least about 200 ug/cm$^2$ (e.g., about 200 ug/cm$^2$ to about 2000 ug/cm$^2$) at 24 hours post application, when tested in vitro using human cadaver skin.
4. The transdermal delivery device of any one of embodiments C1-3, which is configured to provide a mean average flux of dextromethorphan of at least about 5 ug/cm$^2$*h (e.g., about 5 ug/cm$^2$*h to about 20 ug/cm$^2$*h, about 10 ug/cm$^2$*h to about 18 ug/cm$^2$*h) from 8 hours to 24 hours post application, when tested in vitro using human cadaver skin.
5. The transdermal delivery device of any one of embodiments C1-4, wherein the adhesive layer further comprises a skin permeation enhancer in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.
6. The transdermal delivery device of any one of embodiments C1-5, wherein the adhesive layer comprises a skin permeation enhancer in an amount to provide a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.
7. The transdermal delivery device of any one of embodiments C1-6, wherein the adhesive layer comprises a skin permeation enhancer in an amount to provide a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer, when tested in vitro using human cadaver skin.
8. The transdermal delivery device of any one of embodiments C1-7, wherein the adhesive layer comprises a skin permeation enhancer in an amount to provide a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin.
9. The transdermal delivery device of any one of embodiments C1-8, which is suitable for 1-day, 2-day, 3-day, 4-day, 5-day, 6-day, or 7-day application.
10. The transdermal delivery device of embodiment C9, which is configured to provide dextromethorphan to a user of at least about 200 ug/cm$^2$ (e.g., about 200 ug/cm$^2$ to about 2000 ug/cm$^2$) per day.
11. The transdermal delivery device of any one of embodiments C1-10, which has a size of about 5 cm$^2$ to about 200 cm$^2$.
12. The transdermal delivery device of any one of embodiments C1-11, which has a size of about 10 cm$^2$ to about 100 cm$^2$.
13. A transdermal delivery device comprising:
   an adhesive layer comprising dextromethorphan dispersed in an adhesive, wherein the adhesive layer comprises a skin permeation enhancer in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

14. The transdermal delivery device of embodiment C13, wherein the skin permeation enhancer is in an amount to provide a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

15. The transdermal delivery device of embodiment C13 or 14, wherein the skin permeation enhancer is in an amount to provide a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer, when tested in vitro using human cadaver skin.

16. The transdermal delivery device of any one of embodiments C13-15, wherein the skin permeation enhancer is in an amount to provide a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin.

17. The transdermal delivery device of any one of embodiments C13-16, which is suitable for 1-day, 2-day, 3-day, 4-day, 5-day, 6-day, or 7-day application.

18. The transdermal delivery device of embodiment C17, which is configured to provide dextromethorphan to a user of at least about 200 ug/cm$^2$ (e.g., about 200 ug/cm$^2$ to about 2000 ug/cm$^2$) per day.

19. The transdermal delivery device of any one of embodiments C13-18, which has a size of about 5 cm$^2$ to about 200 cm$^2$.

20. The transdermal delivery device of any one of embodiments C13-19, which has a size of about 10 cm$^2$ to about 100 cm$^2$.

21. The transdermal delivery device of any one of embodiments C13-20, wherein the skin permeation enhancer is selected from isopropyl myristate, oleyl oleate, oleic acid, glycerol monooleate, other fatty acids and fatty acid esters with carbon chain lengths of $C_{12}$ to $C_{18}$, and combinations thereof.

22. A method of administering dextromethorphan to a subject in need thereof, the method comprising applying a transdermal delivery device to the skin of the subject, wherein the transdermal delivery device comprises an adhesive layer, wherein the adhesive layer comprises dextromethorphan dispersed in an adhesive, and a skin permeation enhancer, wherein the skin permeation enhancer is in an amount such that the applying results in a mean cumulative dextromethorphan permeated at 24 hours post application of at least about 25% (e.g., about 25%, about 50%, about 100%, about 150%, about 200%, or any ranges between the recited value) higher than that from applying an otherwise equivalent transdermal delivery device without the skin permeation enhancer.

23. The method of embodiment C22, wherein the skin permeation enhancer is in an amount such that the applying results in a mean average flux of dextromethorphan from 8 hours to 24 hours post application of at least about 25% (e.g., about 25%, about 50%, about 100%, about 150%, about 200%, or any ranges between the recited value) higher than that from applying an otherwise equivalent transdermal delivery device without the skin permeation enhancer.

24. The method of embodiment C22 or 23, wherein the skin permeation enhancer is in an amount such that the applying results in a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that from applying an otherwise equivalent transdermal delivery device without the skin permeation enhancer.

25. The method of any one of embodiments C22-24, wherein the skin permeation enhancer is in an amount such that the applying results in a mean average flux of dextromethorphan from 0 hours to 4 hours post application of at least about 5-fold (e.g., about 5-fold, about 8-fold, about 10-fold, about 20-fold, or any ranges between the recited value) of that from applying an otherwise equivalent transdermal delivery device without the skin permeation enhancer.

26. The method of any one of embodiments C22-25, wherein the transdermal delivery device is applied once a day for 1 day or more, (e.g., 1 day, 2 days, 3 days, 4 days, 5 days, 6 days, or 7 days, or more).

27. The method of embodiment C26, which transdermally delivers dextromethorphan to the subject at least about 200 ug/cm$^2$ (e.g., about 200 ug/cm$^2$ to about 2000 ug/cm$^2$) per day.

28. The method of any one of embodiments C22-27, wherein the transdermal delivery device has a size of about 5 cm$^2$ to about 200 cm$^2$.

29. The method of any one of embodiments C22-28, wherein the transdermal delivery device has a size of about 10 cm$^2$ to about 100 cm$^2$.

30. The method of any one of embodiments C22-29, wherein the skin permeation enhancer is selected from isopropyl myristate, oleyl oleate, oleic acid, glycerol monooleate, other fatty acids and fatty acid esters with carbon chain lengths of $C_{12}$ to $C_{18}$, and combinations thereof.

31. A method of administering dextromethorphan to a subject in need thereof, the method comprising applying a transdermal delivery device to the skin of the subject, wherein the transdermal delivery device is configured to have a flux characteristic such that the applying transdermally delivers dextromethorphan about 2 mg/day to about 50 mg/day to the subject.

32. The method of embodiment C31, wherein the transdermal delivery device is configured to have a flux characteristic such that the applying transdermally delivers dextromethorphan about 5 mg/day to about 50 mg/day (e.g., about 5 mg/day, about 10 mg/day, about 20 mg/day, about 30 mg/day, about 40 mg/day, about 50 mg/day, or any ranges between the recited values) to the subject for 1 day or more (e.g., 1.5 days, 2 days, 3 days, 4 days, 5 days, 6 days, 7 days, or any ranges between the recited values).

EXAMPLES

Example 1. Preparation of Dextromethorphan Transdermal Patch

This example shows one procedure for preparing dextromethorphan drug-in-adhesive patch. Dextromethorphan base is generally commercially available. Alternatively, dextromethorphan base can be prepared by conversion of dextromethorphan hydrobromide into the free base, for example, using a 1:1 molar ratio of NaOH.

Preparation of Formulation A, which uses acrylate adhesive with no skin permeation enhancers. In a 150-mL beaker was added in 10 g of ethyl acetate, followed by 2.5 g of DXM. The blend was mixed to dissolve the DXM. While mixing, it was added in acrylic PSA, 50 g of DuroTak 87-2287 (Henkel Adhesives) which has 50.5% of solids. Mixed the batch content for 30 minutes or till the content is homogeneous. The resulting wet solution was then casted onto a release liner (Loparex Corp.), using a casting applicator of 10 mils. The casting was dried in a forced-air oven at 80° C. for 10 min. After drying, the dried casting was laminated to a patch backing film, Scotchpak 1012 (3 M Drug Delivery Systems). The patch was die-cut into a 30 $cm^2$ shape. The resulting transdermal patch has adhesive matrix thickness of 2.5 mils (weighs about 180 mg of adhesive matrix per patch), and contains 9% DXM. HPLC analysis confirmed that a patch contains about 16 mg of DXM. The patch has good skin adhesion and adhered snugly on skin for more than 48 hours. The patch was die-cut to fix on the Franz cells for skin permeation study. No crystals were observed on the patch for 6 months at 25° C., indicating good stability of the transdermal patch formulation.

Preparation of Formulation B, which uses silicone adhesive with no skin permeation enhancers. In a 150-mL beaker was added in 10 g of ethyl acetate, followed by 2.5 g of DXM. The blend was mixed to dissolve the DXM. While mixing, it was added in silicone PSA, 50 g of Bio-PSA DC7-4502 (Dow Corning) which has 60.0% of solids. The batch content was mixed for 30 minutes or till the content is homogeneous. The resulting wet solution was casted onto a fluoropolymer-coated release liner (3M's 1022) using a casting applicator of 15 mils. The casting was dried in a forced-air oven at 80° C. for 10 min. After drying, the dried casting was laminated to a patch backing film, Scotchpak 1012 (3 M Drug Delivery Systems). The patch was die-cut into a 30 $cm^2$ shape. The resulting transdermal patch has adhesive matrix thickness of 3.5 mils. The patch has good skin adhesion and adhered snugly on skin for more than 48 hours. The patch was die-cut to fix on the Franz cells for skin permeation study. No crystals were observed on the patch for 6 months at 25° C., indicating good stability of the transdermal patch formulation.

Preparation of Formulation C, which uses a mixture of acrylate and silicone adhesive with no skin permeation enhancers, with the concentration of dextromethorphan being kept 9%. Following similar procedures above, three formulations were prepared, Formulation C1-$C_3$, with a blend of silicone/acrylic PSA at a ratio of 54/46, 18/82, and 9/91, respectively.

Preparation of Formulation D, Following similar procedures above, formulations with various amounts of permeation enhancers are also prepared. Formulation D1 contains isopropyl myristate in an amount of 7.7%; Formulation D2 contains isopropyl myristate in an amount of 10%. As a control, Formulation D0 was also prepared, which contains no isopropyl myristate.

The following table 1 summarizes the ingredients of different formulations prepared above, with weight percentages. (The percentages in the table refers to dry weight.)

TABLE 1

| Formulation No. | A | B | C1 | C2 | C3 | D0 | D1 | D2 |
|---|---|---|---|---|---|---|---|---|
| DXM | 9 | 8 | 9 | 9 | 9 | 10 | 10 | 10 |
| DuroTak 87-2287 | 91 | 92 | 49 | 16 | 8 | 90 | 82.3 | 80 |
| DC 7-4502 | | | 42 | 75 | 83 | | | |
| IPM | | | | | | 0 | 7.7 | 10 |
| Total | 100 | 100 | 100 | 100 | 100 | 100 | 100 | 100 |

Preparation of Formulation E, Following similar procedures above, formulations with a crystallization inhibitor was also prepared. Formulation E1 contains, by dry weight percentage, about 10% of dextromethorphan base, about 10% of isopropyl myristate, about 70% of polyacrylate adhesive (DuroTak 387-2287), and about 10% of crystallization inhibitor Plasdone K-29/32 (a polyvinylpyrrolidone). The ingredients were blended with isopropanol to form a homogenous solution. This wet formulation has the following ingredients, about 63.1% of polyacrylate adhesive (DuroTak 387-2287, has about 50% solid content), about 4.5% Plasdone K-29/32 (a polyvinylpyrrolidone), about 4.5% isopropyl myristate, about 4.5% dextromethorphan base, and about 23.4% isopropyl alcohol. This wet formulation was casted onto a release liner (3 Mil PET 8310, silicone coated polyester film) and then dried. The dried casting was then laminated to a patch backing film, Scotchpak 9733 PET film. The patch was die-cut into desired size. In one example, this formulation was used to prepare transdermal patches, for example, with about 56 mg of dextromethorphan base and a size of about 70 $cm^2$.

Example 2. Transdermal Flux Test

Transdermal flux of Dextromethorphan from the patch was tested using human cadaver skin by Franz Diffusion Cell method.

Patch formulations A, B, and C prepared in Example 1 were used for a skin permeation study using the following protocol:

- Franz cell assembly—Logan Instruments (6-cell unit)
- Each cell has 12 mL volume, 1.5 cm diameter orifice
- Receptor medium is a phosphate buffer solution (PBS) pH 7.4
- Cell temperature is maintained at 37° C.
- Sampling method: take 1.5 mL for HPLC assay, empty cell, replace with fresh medium
- Sampling time points: 4, 8, 12, 24 and 48 hours
- Cadaver skin is used and is obtained from New York Fire Fighters Skin Bank. Skin No. MM07116, White, Age 58, male, skin site: left posterior leg.
- Assay method for media: HPLC based.

RESULTS of the study for Formulations A and B are presented in Table 1 below (See also FIG. 1). The skin permeation experiments were conducted up to 48 hours (2 days). The values presented are cumulative amount of DXM permeated per $cm^2$ (i.e., ug/$cm^2$).

TABLE 2

| Hours | Formulation A Acrylic PSA DuroTak 87-2287 | Formulation B Silicone PSA DC7-4502 |
|---|---|---|
| 0 | 0.0 | 0.0 |
| 4 | 48.6 | 25.8 |
| 8 | 124.9 | 79.8 |
| 12 | 201.3 | 138.1 |
| 24 | 424.3 | 294.4 |
| 48 | 625.1 | 597.0 |

RESULTS of the study for Formulations C1-C3 are presented in Table 3 below (See also FIG. 2). The skin permeation experiments were conducted up to 7 days. The values presented are cumulative amount of DXM permeated per cm$^2$ (i.e., ug/cm$^2$).

TABLE 3

| | Formulation | | |
|---|---|---|---|
| | C1 | C2 | C3 |
| | Sil:Acrylic ratio | | |
| Day | 54/46 | 18/82 | 9/91 |
| 0.33 | 71.0 | 34.8 | 159.5 |
| 1 | 308.1 | 215.9 | 487.0 |
| 2 | 536.5 | 433.3 | 768.8 |
| 3 | 667.8 | 584.1 | 902.6 |
| 4 | 755.2 | 703.7 | 979.1 |
| 5 | 815.8 | 784.0 | 1023.5 |
| 6 | 866.3 | 854.6 | 1060.6 |
| 7 | 906.7 | 910.2 | 1086.1 |

Example 3A. Dextromethorphan Transdermal Patch with Permeation Enhancers

Formulations D0-D2 were also tested for their in vitro skin flux characteristics following the same protocol as described in Example 2. The results are shown in Table 4A (see also FIG. 3A).

TABLE 4A

| | Formulation D0 | Formulation D1 | Formulation D2 |
|---|---|---|---|
| IPM % | 0 | 7.7 | 10.0 |
| 24-h flux, mg/cm2 | 141.3 | 240.0 | 334.6 |

The results clearly indicate that increased level of IPM, up to 10%, significantly enhance the skin permeation of DXM.

Example 3B. Dextromethorphan Transdermal Patch with Plasdone (PVP)

Formulation E1 was also tested for their in vitro skin flux characteristics using dermatomed human cadaver skins.

| | |
|---|---|
| Apparatus: | Vertical diffusion cells |
| Skin Type: | Human cadaver skin (dermatomed) |
| Dose Area: | 1.767 $cm_2$ (1-cm diameter opening for diffusion cell) |
| Diffusion Cell Volume: | 12 mL |

-continued

| | |
|---|---|
| Receiving Medium: | Phosphate buffered saline pH 7.4 |
| Medium Temperature: | 37° C. ± 1.0° C. |
| Sampling Intervals: | 4, 8, 24, and 48 hours |
| Sampling Volume: | 1.5-2.0 mL |

The protocol described in Example 2 was followed to test the permeability of Formulation E1. Permeation of drugs into the receptor compartment at various time points (calculated from concentration of the permeated drugs in each cell), per unit area (i.e., ug/cm$^2$) is reported.

The results are shown in Table 4B (see also FIG. 3B).

TABLE 4B

| In vitro Permeation on Franz Cell of Dextromethophan patch | |
|---|---|
| Time points (hours) | Average DXM Permeated (μg/cm2) |
| 4 | 119.6 |
| 8 | 250.5 |
| 24 | 681.0 |
| 48 | 1062.4 |

It was surprising to observe that the in vitro permeation of dextromethorphan was significantly enhanced with the addition of Plasdone. According to Example 3A, the same formulation without Plasdone achieved a 24-hour flux of only about 334 ug/cm$^2$. Thus, the inclusion of Plasdone more than doubled the cumulative in vitro permeation of dextromethorphan at 24 hours. Both studies were conducted for freshly prepared patches. This enhancement of permeation was also observed in the in vivo study, see Example 4.

Example 4. In Vivo Pharmacokinetic Studies

Example 4A. Single-Dose Pharmacokinetic Studies

This example concerns an open-label, randomized, two-treatment, two-period, two-sequence crossover study that was conducted with 16 healthy adult male and female subjects to evaluate the comparative bioavailability of a test dextromethorphan patch, 15 mg/24 hr relative to that of NUEDEXTA® (dextromethorphan hydrobromide and quinidine sulfate) capsules, 20 mg/10 mg (Avanir Pharmaceuticals, Inc.) under fasted conditions. The 16 subjects in this study were all genotyped to determine CYP2D6 genotype. All 16 subjects can be characterized as dextromethorphan extensive metabolizer. See e.g., Treducu A. L. D. et al. *Frontiers in Pharmacology*, vol. 9, Article 305 (April 2018).

The pharmacokinetic profile for both dextromethorphan and dextrorphan (one metabolite of dextromethorphan) were measured in this study.

In one period of the study, one (1) dextromethorphan patch, a 45 cm$^2$ patch with 35 mg DXM, which is a drug-in-adhesive patch, with the DIA layer containing about 80% by weight of an adhesive (Duro-Tak 87-2287), about 10% by weight of dextromethorphan base and about 10% by weight of permeation enhancer isopropyl myristate, which was designed to transdermally deliver about 15 mg/24 hr, was applied on the upper outer left arm of healthy subjects for 24 hours following an overnight fast of at least 10 hours. In the other study period, a single NUEDEXTA® (dextromethorphan hydrobromide and quinidine sulfate) capsule, 20 mg/10 mg, was administered every 12 hours (0 and 12 hours) (for a total dose of 40 mg/20 mg over a 24-hour period) following an overnight fast of at least 10 hours (0-hour).

For NUEDEXTA® treatment, the subjects were overnight fasted of at least 10 hours only prior to the 0-hour dose. The order of administration follows a two-sequence randomization schedule. Blood samples were collected pre-dose and at intervals over 96 hours after dosing (0-hour) with the study drug in each study period. Subjects were confined at the clinical facility from at least 10 hours before dosing (0-hour) until after the 36-hour blood sample collection in each study period and returned to the clinical facility for the 48-, 72- and 96-hour blood sample collections. The interval between doses (0-hour) were at least 10 days.

The plasma concentrations of dextromethorphan and its active metabolite dextrorphan were measured by a fully validated analytical procedure. Statistical analysis using average bioequivalence methodology was performed to evaluate the bioavailability of the test formulation relative to that of the reference product for dextromethorphan and dextrorphan only.

The study was designed based on the known pharmacokinetics of NUEDEXTA® (dextromethorphan hydrobromide and quinidine sulfate) Capsules, the FDA Draft Guidance on dextromethorphan hydrobromide and quinidine sulfate capsules, and generally accepted standards for the conduct of bioavailability/bioequivalence studies under fasted conditions and adhesion studies. To minimize any possibility of a carry-over effect, a washout period of at least 10 days was selected for this study.

The study was also designed to minimize potential drug-drug-interaction that may affect the results of this study. For example, the subjects were screened and monitored for taking drugs such as MAO inhibitors, tricyclic antidepressants, SSRIs, drugs that are implicated in TdP or cardiac arrhythmia, inducers or inhibitors of CYP3A4, or CYP2D6 etc.

Pharmacokinetic Results

Blood samples were collected at these time points (relative to dosing minute): Pre-dose (0-hour) and at 0.5, 1.0, 1.5, 2.0, 3.0, 4.0, 5.0, 6.0, 7.0, 9.0, 12.0, 13.0, 14.0, 15.0, 16.0, 17.0, 18.0, 20.0, 24.0, 24.5, 25.0, 26.0, 30.0, 36.0, 48.0*, 72.0* and 96.0* hours post-dose (* return sample). The samples were then processed and analyzed for both dextromethorphan and dextrophan concentrations using validated analytical methods. SAS®, Version 9.4 or higher was used for all pharmacokinetic and statistical calculations.

Tables 5A-5D show the results from this study. Tables 5A and 5C show the dextromethorphan and dextrophan plasma concentrations, respectively, in subjects orally administered Neudextra (Reference) twice a day. Tables 5B and 5D show the dextromethorphan and dextrophan plasma concentrations, respectively, in subjects treated with dextromethorphan patch for 24 hours.

TABLE 5A

Dextromethorphan PK Profile in Subjects Treated Nuedexta

| Sub. | Per. | Seq. | AUC 0-t/ AUC 0-∞ | AUC 0-∞ | AUC 0-t (h · ng/mL) | AUC 0-24 | Cmax (ng/mL) | Tmax (h) |
|---|---|---|---|---|---|---|---|---|
| 2001 | 1 | 2 | 0.993 | 351.9471 | 349.606 | 184.0613 | 16.601 | 15 |
| 2002 | 2 | 1 | 0.964 | 195.315 | 188.2605 | 125.9288 | 10.095 | 18 |
| 2003 | 1 | 2 | 0.968 | 678.6678 | 657.1278 | 261.3503 | 18.961 | 15 |
| 2004 | 2 | 1 | 0.925 | 1179.091 | 1090.282 | 413.963 | 25.246 | 18 |
| 2005 | 1 | 2 | 0.985 | 241.7969 | 238.2765 | 139.581 | 10.527 | 16 |
| 2006 | 2 | 1 | 0.988 | 113.702 | 112.3683 | 71.981 | 5.179 | 18 |
| 2007 | 1 | 2 | 0.988 | 212.503 | 209.9133 | 120.7003 | 9.266 | 16 |
| 2008 | 2 | 1 | 0.987 | 199.7647 | 197.2488 | 115.1745 | 8.949 | 17 |
| 2009 | 1 | 2 | 0.977 | 61.9881 | 60.5778 | 41.9003 | 3.009 | 17 |
| 2010 | 2 | 1 | 0.992 | 420.076 | 416.5713 | 198.18 | 14.367 | 16 |
| 2011 | 2 | 1 | 0.991 | 146.6518 | 145.3553 | 94.6668 | 7.912 | 16 |
| 2012 | 1 | 2 | 0.987 | 630.2464 | 622.358 | 258.1298 | 17.371 | 18 |
| 2013 | 2 | 1 | 0.96 | 1127.656 | 1082.814 | 391.2635 | 27.377 | 17 |
| 2014 | 1 | 2 | 0.99 | 209.3143 | 207.2588 | 119.782 | 9.519 | 18 |
| 2015 | 2 | 1 | 0.989 | 203.16 | 200.8948 | 123.0515 | 11.967 | 15 |
| 2016 | 1 | 2 | 0.994 | 413.279 | 410.8915 | 188.3373 | 13.428 | 16 |
| N | | | 16 | 16 | 16 | 16 | 16 | 16 |
| Mean | | | 0.98 | 399.0725 | 386.8627 | 178.0032 | 13.1109 | 16.625 |
| St. Dev. | | | 0.0182 | 341.34 | 321.0667 | 106.3368 | 6.6888 | 1.1475 |
| CV(%) | | | 1.8534 | 85.5333 | 82.9924 | 59.7387 | 51.0169 | 6.902 |
| Min. | | | 0.9247 | 61.9881 | 60.5778 | 41.9003 | 3.009 | 15 |
| Median | | | 0.9876 | 227.15 | 224.0949 | 132.7549 | 11.247 | 16.5 |
| Max. | | | 0.9942 | 1179.091 | 1090.282 | 413.963 | 27.377 | 18 |
| Geometric Mean | | | — | 293.6809 | 287.7623 | 151.5212 | 11.4739 | — |
| Geometric CV(%) | | | — | 96.1162 | 94.5644 | 65.4088 | 60.9954 | — |

TABLE 5B

Dextromethorphan PK Profile in Subjects Treated DXM Patch

| Sub. | Per. | Seq. | AUC 0-t/ AUC 0-∞ | AUC 0-∞ | AUC 0-t (h · ng/mL) | AUC 0-24 | Cmax (ng/mL) | Tmax (h) | Kel (h-1) |
|---|---|---|---|---|---|---|---|---|---|
| 2001 | 2 | 2 | 0.995 | 343.5848 | 341.9338 | 225.8408 | 12.168 | 13 | 0.0521 |
| 2002 | 1 | 1 | 0.979 | 157.7533 | 154.4763 | 83.966 | 5.918 | 24 | 0.0598 |
| 2003 | 2 | 2 | 0.993 | 254.6006 | 252.7 | 138.4305 | 7.924 | 13 | 0.0558 |
| 2004 | 1 | 1 | 0.909 | 762.9419 | 693.3915 | 227.2223 | 15.069 | 25 | 0.028 |
| 2005 | 2 | 2 | 0.981 | 108.1344 | 106.0843 | 39.8225 | 3.565 | 24 | 0.0449 |
| 2006 | 1 | 1 | 0.976 | 155.7666 | 152.0265 | 76.285 | 5.39 | 24 | 0.0406 |
| 2007 | 2 | 2 | 0.974 | 76.1848 | 74.1835 | 37.4935 | 2.768 | 24 | 0.0655 |
| 2008 | 1 | 1 | 0.953 | 160.8027 | 153.2865 | 101.7265 | 5.729 | 9 | 0.089 |
| 2009 | 2 | 2 | 0.983 | 135.951 | 133.5808 | 60.496 | 5.299 | 24.5 | 0.0464 |
| 2010 | 1 | 1 | 0.989 | 170.5676 | 168.6183 | 93.6805 | 5.488 | 24.5 | 0.0487 |
| 2011 | 1 | 1 | 0.981 | 150.6617 | 147.8318 | 88.5355 | 5.359 | 13 | 0.0594 |
| 2012 | 2 | 2 | 0.991 | 175.1153 | 173.5208 | 89.2915 | 5.41 | 24 | 0.0583 |
| 2013 | 1 | 1 | 0.972 | 135.1146 | 131.3655 | 59.5475 | 5.058 | 24.5 | 0.0501 |
| 2014 | 2 | 2 | 0.988 | 103.1524 | 101.9025 | 51.8775 | 3.747 | 13 | 0.0448 |
| 2015 | 1 | 1 | 0.99 | 89.5274 | 88.629 | 49.1685 | 3.503 | 24.5 | 0.0601 |
| 2016 | 2 | 2 | 0.98 | 118.201 | 115.859 | 56.2235 | 3.982 | 24.5 | 0.0418 |
| N | | | 16 | 16 | 16 | 16 | 16 | 16 | 16 |
| Mean | | | 0.9771 | 193.6287 | 186.8369 | 92.4755 | 6.0236 | 20.5313 | 0.0528 |
| St. Dev. | | | 0.0208 | 165.2082 | 149.9839 | 58.4479 | 3.2516 | 5.8807 | 0.0135 |
| CV(%) | | | 2.1321 | 85.3221 | 80.2753 | 63.2036 | 53.9815 | 28.6425 | 25.5494 |
| Min. | | | 0.9088 | 76.1848 | 74.1835 | 37.4935 | 2.768 | 9 | 0.028 |
| Median | | | 0.9811 | 153.2141 | 149.9291 | 80.1255 | 5.3745 | 24 | 0.0511 |
| Max. | | | 0.9952 | 762.9419 | 693.3915 | 227.2223 | 15.069 | 25 | 0.089 |
| Geometric Mean | | | — | 160.6092 | 156.8942 | 79.6881 | 5.4375 | — | — |
| Geometric CV(%) | | | — | 60.1868 | 58.6836 | 58.0178 | 46.2616 | — | — |

TABLE 5C

Dextrorphan PK Profile in Subjects Treated Nuedexta

| Sub. | Per. | Seq. | AUC 0-t/ AUC 0-∞ | AUC 0-∞ | AUC 0-t (h · ng/mL) | AUC 0-24 | Cmax (ng/mL) | Tmax (h) |
|---|---|---|---|---|---|---|---|---|
| 2001 | 1 | 2 | 0.91 | 54.6319 | 49.7395 | 37.0408 | 2.508 | 15 |
| 2002 | 2 | 1 | 0.95 | 54.7694 | 52.0113 | 44.3253 | 4.736 | 3 |
| 2003 | 1 | 2 | 0.79 | 44.4308 | 35.1195 | 19.2823 | 1.375 | 3 |
| 2004 | 2 | 1 | 0.758 | 45.5979 | 34.5633 | 16.5818 | 0.997 | 18 |
| 2005 | 1 | 2 | 0.933 | 49.1071 | 45.8165 | 37.2095 | 2.842 | 2 |
| 2006 | 2 | 1 | 0.846 | 21.7259 | 18.3733 | 17.4788 | 1.763 | 2 |
| 2007 | 1 | 2 | 0.923 | 34.5947 | 31.9278 | 25.6383 | 1.927 | 15 |
| 2008 | 2 | 1 | 0.863 | 27.3844 | 23.634 | 20.3403 | 1.463 | 3 |
| 2009 | 1 | 2 | 0.977 | 61.0768 | 59.6648 | 50.6268 | 4.251 | 16 |
| 2010 | 2 | 1 | 0.88 | 47.2853 | 41.614 | 29.7973 | 2.385 | 5 |
| 2011 | 2 | 1 | 0.944 | 44.4111 | 41.9088 | 38.2585 | 4.014 | 2 |
| 2012 | 1 | 2 | 0.773 | 35.9404 | 27.7748 | 18.5353 | 1.369 | 4 |
| 2013 | 2 | 1 | — | — | 24.2913 | 9.816 | 0.709 | 18 |
| 2014 | 1 | 2 | 0.907 | 33.6648 | 30.522 | 24.7718 | 1.804 | 3 |
| 2015 | 2 | 1 | 0.872 | 42.554 | 37.1155 | 29.618 | 2.482 | 2 |
| 2016 | 1 | 2 | 0.877 | 37.8946 | 33.2445 | 26.2825 | 2.035 | 4 |
| N | | | 15 | 15 | 16 | 16 | 16 | 16 |
| Mean | | | 0.8802 | 42.338 | 36.7075 | 27.8502 | 2.2913 | 7.1875 |
| St. Dev. | | | 0.0657 | 10.6596 | 11.2148 | 11.1675 | 1.1676 | 6.5138 |
| CV(%) | | | 7.469 | 25.1775 | 30.5518 | 40.0985 | 50.9602 | 90.6263 |
| Min. | | | 0.758 | 21.7259 | 18.3733 | 9.816 | 0.709 | 2 |
| Median | | | 0.8801 | 44.4111 | 34.8414 | 25.9604 | 1.981 | 3.5 |
| Max. | | | 0.9769 | 61.0768 | 59.6648 | 50.6268 | 4.736 | 18 |
| Geometric Mean | | | — | 40.9614 | 35.0859 | 25.6926 | 2.0294 | — |
| Geometric CV(%) | | | — | 28.0586 | 32.3114 | 44.7726 | 55.4075 | — |

TABLE 5D

| Dextrorphan PK Profile in Subjects Treated DXM Patch | | | | | | | | | |
|---|---|---|---|---|---|---|---|---|---|
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) | Kel (h-1) |
| 2001 | 2 | 2 | 0.816 | 23.5515 | 19.2253 | 9.77 | 0.665 | 26 | 0.0495 |
| 2002 | 1 | 1 | — | — | 13.3518 | 7.81 | 0.658 | 13 | — |
| 2003 | 2 | 2 | 0.786 | 15.0118 | 11.7988 | 7.563 | 0.478 | 20 | 0.071 |
| 2004 | 1 | 1 | — | — | 16.3933 | 6.348 | 0.58 | 24.5 | — |
| 2005 | 2 | 2 | — | — | 1.5003 | 0 | 0.279 | 30 | — |
| 2007 | 2 | 2 | — | — | 2.594 | 0.955 | 0.286 | 30 | — |
| 2008 | 1 | 1 | — | — | 7.8075 | 5.6295 | 0.431 | 24 | — |
| 2009 | 2 | 2 | — | — | 4.7703 | 3.265 | 0.354 | 12 | — |
| 2010 | 1 | 1 | — | — | 11.3405 | 6.759 | 0.539 | 26 | — |
| 2011 | 1 | 1 | — | — | 1.6505 | 1.102 | 0.312 | 26 | — |
| 2012 | 2 | 2 | — | — | 4.957 | 2.741 | 0.401 | 24 | — |
| 2013 | 1 | 1 | — | — | 13.1663 | 6.377 | 0.683 | 24 | — |
| 2014 | 2 | 2 | — | — | 6.6303 | 4.4165 | 0.393 | 26 | — |
| 2015 | 1 | 1 | — | — | 10.327 | 5.9315 | 0.588 | 14 | — |
| 2016 | 2 | 2 | — | — | 4.1193 | 2.386 | 0.319 | 26 | — |
| N | | | 2 | 2 | 15 | 15 | 15 | 15 | 2 |
| Mean | | | 0.8011 | 19.2816 | 8.6421 | 4.7369 | 0.4644 | 23.0333 | 0.0602 |
| St. Dev. | | | 0.0215 | 6.0384 | 5.5101 | 2.8797 | 0.1446 | 5.7273 | 0.0152 |
| CV(%) | | | 2.6783 | 31.317 | 63.7586 | 60.7921 | 31.1453 | 24.8654 | 25.2412 |
| Min. | | | 0.786 | 15.0118 | 1.5003 | 0 | 0.279 | 12 | 0.0495 |
| Median | | | 0.8011 | 19.2816 | 7.8075 | 5.6295 | 0.431 | 24.5 | 0.0602 |
| Max. | | | 0.8163 | 23.5515 | 19.2253 | 9.77 | 0.683 | 30 | 0.071 |
| Geometric Mean | | | — | 18.8029 | 6.7033 | 4.1953 | 0.4433 | — | — |
| Geometric CV(%) | | | — | 32.6691 | 96.3776 | 82.6752 | 32.64 | — | — |

Based on this study, it was also unexpectedly found that for subjects treated with DXM patch, the ratios of $AUC_{0-24}$, $AUC_{0-t}$, and $C_{max}$ of DXM to DRP observed for the patch treatment were significantly higher than the respective ratios observed for the Nuedexta treatment. For example, the mean ratio of $AUC_{0-24}$ of DXM to DRP observed for the patch treatment is close to 3× of that observed for Nuedexta treatment (24.54:9.03), see table 6 below.

TABLE 6

| Comparison of PK Profiles for Patch Nuedexta Treatments | | | | | | | | | | |
|---|---|---|---|---|---|---|---|---|---|---|
| | Nuedexta Treatment | | | | | Patch Treatment | | | | |
| Sub. | Per. | Seq. | AUC 0-t (DXM/ DRP) | AUC 0-24 (DXM/ DRP) | Cmax (DXM/ DRP) | Per. | Seq. | AUC 0-t (DXM/ DRP) | AUC 0-24 (DXM/ DRP) | Cmax (DXM/ DRP) |
| 2001 | 1 | 2 | 7.03 | 4.97 | 6.62 | 2 | 2 | 17.79 | 23.12 | 18.30 |
| 2002 | 2 | 1 | 3.62 | 2.84 | 2.13 | 1 | 1 | 11.57 | 10.75 | 8.99 |
| 2003 | 1 | 2 | 18.71 | 13.55 | 13.79 | 2 | 2 | 21.42 | 18.30 | 16.58 |
| 2004 | 2 | 1 | 31.54 | 24.96 | 25.32 | 1 | 1 | 42.30 | 35.79 | 25.98 |
| 2005 | 1 | 2 | 5.20 | 3.75 | 3.70 | 2 | 2 | 70.71 | — | 12.78 |
| 2006 | 2 | 1 | 6.12 | 4.12 | 2.94 | 1 | 1 | — | — | — |
| 2007 | 1 | 2 | 6.57 | 4.71 | 4.81 | 2 | 2 | 28.60 | 39.26 | 9.68 |
| 2008 | 2 | 1 | 8.35 | 5.66 | 6.12 | 1 | 1 | 19.63 | 18.07 | 13.29 |
| 2009 | 1 | 2 | 1.02 | 0.83 | 0.71 | 2 | 2 | 28.00 | 18.53 | 14.97 |
| 2010 | 2 | 1 | 10.01 | 6.65 | 6.02 | 1 | 1 | 14.87 | 13.86 | 10.18 |
| 2011 | 2 | 1 | 3.47 | 2.47 | 1.97 | 1 | 1 | 89.57 | 80.34 | 17.18 |
| 2012 | 1 | 2 | 22.41 | 13.93 | 12.69 | 2 | 2 | 35.01 | 32.58 | 13.49 |
| 2013 | 2 | 1 | 44.58 | 39.86 | 38.61 | 1 | 1 | 9.98 | 9.34 | 7.41 |
| 2014 | 1 | 2 | 6.79 | 4.84 | 5.28 | 2 | 2 | 15.37 | 11.75 | 9.53 |
| 2015 | 2 | 1 | 5.41 | 4.15 | 4.82 | 1 | 1 | 8.58 | 8.29 | 5.96 |
| 2016 | 1 | 2 | 12.36 | 7.17 | 6.60 | 2 | 2 | 28.13 | 23.56 | 12.48 |
| N | | | 16 | 16 | 16 | | | 15 | 16 | |
| Mean | | | 12.07 | 9.03 | 8.88 | | | 29.43 | 24.54 | 13.12 |
| St. Dev. | | | 11.78 | 10.15 | 9.96 | | | 22.93 | 18.82 | 5.06 |
| CV(%) | | | 97.60% | 112.45% | 112.10% | | | 77.89% | 76.70% | 38.60% |

FIGS. 4A and 4B show the graph of dextromethorphan and dextrorphan concentrations from 0-96 hours.

Example 4B. Multiple-Dose Pharmacokinetic Studies

This example concerns an open-label, randomized, multiple-dose, two-treatment, two-period, two-sequence crossover study was conducted with 20 healthy adult male and female subjects to evaluate the bioavailability of a test dextromethorphan patch, 35 mg/24 hr (1×patch applied/replaced, as applicable, every 24 hours for 7 days (7 doses) from Day 1 to Day 7 [final patch removal on the morning of Day 8]) relative to that of the NUEDEXTA® (dextromethorphan hydrobromide and quinidine sulfate) capsules, 20 mg/10 mg (Avanir Pharmaceuticals, Inc.; 1×capsule administered every 12 hours for 7 days [14 doses] from Day 1 through Day 7 for a total daily dose of 40 mg/20 mg over a 24-hour period). The test dextromethorphan patches have a drug-in-adhesive layer according to Formulation E1. The test dextromethorphan patches each include about 56 mg of dextromethorphan base, about 392 mg of Duro-Tak polyacrylate (Duro-Tak 387-2287) adhesive, about 56 mg of Plasdone K-29/32, and about 56 mg of isopropyl myristate, and have a size of about 70 $cm^2$.

Both dextromethorphan and dextrorphan were measured in this study.

In one period of the study, the subjects received Treatment A: 1×test dextromethorphan patch, 35 mg/24 hr applied/replaced on the designated application site, as applicable, every 24 hours for 7 days (7 doses) from Day 1 to Day 7 (final patch removal on the morning of Day 8). The Day 1, 0-hour dose was administered following an overnight fast of at least 10 hours; subsequent doses were administered following a fast of at least 6 hours. Blood samples were collected before each patch application, at intervals over 24 hours after patch application on Days 1 and 7, and over 72 hours post-patch removal on Day 7.

In the other study period, the subjects received Treatment B: 1×20 mg/10 mg NUEDEXTA® (dextromethorphan hydrobromide and quinidine sulfate) capsule administered every 12 hours for 7 days (14 doses) from Day 1 through Day 7 (total daily dose of 40 mg/20 mg, equivalent to 29.31 mg of dextromethorphan base over a 24-hour period). The Day 1, 0-hour dose was administered following an overnight fast of at least 10 hours; subsequent doses were administered following a fast of at least 4 hours. Blood samples were collected before the 0-hour dose on Day 1, at intervals over the first 12-hour dosing interval on Day 1, before the morning (0-hour) and evening (12-hour) doses on Days 5 and 6, before the morning dose on Day 7 (0-hour), and at intervals over the two 12-hour dosing intervals on Day 7 (i.e., for 24 hours after the morning dose on Day 7).

Subjects were confined at the clinical facility from at least 10 hours before Day 1, 0 hour dosing until at least 36 hours after Day 7, 0-hour dosing (i.e., 180 hours after Day 1, 0-hour dosing) in each study period. Subjects receiving Treatment A returned to the clinical facility for the 48-, 72- and 96-hour blood sample collections. The interval between the last dose in Period I and the first dose in Period II was 16 days.

The plasma concentrations of dextromethorphan and its active metabolite dextrorphan (unconjugated) were measured by a fully validated analytical procedure. Statistical analysis using analysis of variance (ANOVA) methodology was performed to evaluate the bioavailability of the test formulation relative to that of the reference product on Day 7 following administration of the two products for 7 days.

The site of patch application was on either the subject's upper outer arm, front chest or upper back. The patch was removed 24 hours (+5 minutes) after application.

Pharmacokinetic Sample Collections

Treatment A: On Day 1, 7 mL venous blood was collected in chilled K3EDTA vacutainers within 60 minutes before patch application at 0-hour and at 1.0, 2.0, 4.0, 6.0, 8.0, 10.0, 12.0, 14.0, 16.0, 18.0, 20.0, 22.0 and 23.0 hours post-application. On Day 2, a pre-dose sample was collected before patch application.† This sample is equivalent to the 24.0 hour post-application sample from Day 1. On Days 3 through 6, a pre-dose sample was collected before each patch application.† On Day 7, a pre-dose sample was collected within 5 minutes before patch application (0-hour)† and at 1.0, 2.0, 4.0, 6.0, 8.0, 10.0, 12.0, 14.0, 16.0, 18.0, 20.0, 22.0, 23.0, 24.0 (within 5 minutes before patch removal), 24.5, 25.0, 26.0, 28.0, 30.0, 32.0, 36.0, 48.0*, 72.0* and 96.0* hours post-dose (*return sample). †Samples collected immediately before each dosing with an allowed deviation of −5 minutes to accommodate dosing activities, as necessary.

Treatment B: On Day 1, 7 mL venous blood was collected in chilled K3EDTA vacutainers within 60 minutes before morning dosing at 0-hour and at 1.0, 2.0, 3.0, 4.0, 4.5, 5.0, 5.5, 6.0, 7.0, 8.0, 10.0 and 12.0† hours post-dose. On Days 5 and 6, pre-dose samples were collected before each dose administration (0- and 12-hour administrations on Days 5 and 6)†. On Day 7, a pre-dose sample was collected within 5 minutes before dosing† and at 1.0, 2.0, 3.0, 4.0, 4.5, 5.0, 5.5, 6.0, 8.0, 12.0†, 13.0, 14.0, 15.0, 16.0, 17.0, 18.0, 20.0 and 24.0 hours post-dose. †Samples collected immediately before each dosing with an allowed deviation of −5 minutes to accommodate dosing activities, as necessary.

All times were relative to the dosing minute. After collection, the samples were processed and analyzed. Pharmacokinetic and statistical services were performed using SAS®, Version 9.4 or higher for all pharmacokinetic and statistical calculations.

The following pharmacokinetic parameters were determined for each subject and each analyte for the test and the reference products:

- $AUC_{0-12,D1}$: Area under the plasma concentration-time curve, from time zero (0) to the end of the morning 12-hour dosing interval on Day 1 following the first dose of Treatment B
- $AUC_{0-24,D1}$: Area under the plasma concentration-time curve, from time zero (0) to the end of the 24-hour dosing interval on Day 1 following the first dose of Treatment A
- $AUC_{0-12,D7}$: Area under the plasma concentration time curve from time zero (0) to the end of the morning 12-hour dosing interval on Day 7 for Treatment B
- $AUC_{0-24,D7}$: Area under the plasma concentration time curve from time zero (0) to the end of the 24-hour dosing interval on Day 7 for Treatment A and over the two 12-hour dosing intervals from the morning (0-hour) dose to the end of the evening 12-hour dosing interval at 24 hours for Treatment B
- $AF_{TreatmentA}$: Accumulation Factor Treatment A ($AUC_{0-24,D7}$ divided by $AUC_{0-24,D1}$) for Treatment A
- $AF_{TreatmentB}$: Accumulation Factor Treatment B ($AUC_{0-12,D7}$ divided by $AUC_{0-12,D1}$) for Treatment B
- $C_{avg,D7}$: Observed average plasma concentration on Day 7, calculated as $AUC_{0-24,D7}$/24 hours
- $C_{max,D1}$: Maximum observed plasma concentration on Day 1 over the 24-hour dosing interval for Treatment A and over the first 12-hour dosing interval for Treatment B
- $C_{max,D7}$: Maximum observed plasma concentration on Day 7
- $C_{min,D7}$: Minimum observed plasma concentration on Day 7
- $C_{pre,Dx}$: Observed morning and evening pre-dose plasma concentration on Days 1-7, where x=1-7 for Treatment A and x=1M, 5M, 5E, 6M, 6E, 7M, 7E (M=morning and E=evening) for Treatment B
- $C_{12,D1}$: Observed pre-dose plasma concentration at the end of the first 12-hour dosing interval for Treatment B on Day 1

$C_{24,D7}$: Observed plasma concentration at the end of the last dosing interval (i.e., at 24-hours following patch application on Day 7 for Treatment A and at 12 hours following the evening 12-hour dose on Day 7, which is 24 hours following the morning 0-hour dose on Day 7 for Treatment B)

Fluctuation: Calculated as $[(C_{max,D7}-C_{min,D7})/C_{avg,D7}]$. $C_{max,D7}$ and $C_{min,D7}$ may be in different dosing intervals for Treatment B on Day 7.

Swing: Calculated as $[(C_{max,D7}-C_{min,D7})/C_{min,D7}]$. $C_{max,D7}$ and $C_{min,D7}$ may be in difference dosing intervals for Treatment B on Day 7.

$T_{max,D1}$: Time to reach the maximum observed plasma concentration on Day 1 over the 24-hour dosing interval for Treatment A and over the first 12-hour dosing interval for Treatment B $T_{max,D7}$: Time to reach the maximum observed plasma concentration on Day 7

$\lambda_{z,D7}$: Apparent first-order terminal disposition rate constant following the last dose on Day 7 (For Treatment A only)

$t_{1/2,D7}$: Apparent first-order terminal disposition half-life following the last dose on Day 7 (For Treatment A only)

$MR_{Dx}$ Metabolic ratio, expressed as the ratio of dextromethorphan $AUC_{0-24}$ to dextrorphan $AUC_{0-24}$ on Day 1 ($MR_{D1}$) and Day 7 ($MR_{D7}$) for Treatment A and as the ratio of dextromethorphan $AUC_{0-12}$ to dextrorphan $AUC_{0-12}$ on Day 1 ($MR_{D1}$) and Day 7 ($MR_{D7}$) for Treatment B; Ratio of $MR_{D7}/MR_{D1}$, designated as $MR_{D7/D1}$ $CL_{TD}$ Apparent transdermal clearance of dextromethorphan for Treatment A on Day 7 ($CL_{TD}$=CL/F=Dose/$AUC_{0-24,D7}$, where Dose=35 mg)

$CL_O$ Apparent oral clearance of dextromethorphan for Treatment B on Day 7 ($CL_O$=CL/F=Dose/$AUC_{0-12,D7}$, where Dose=14.66 mg, and =Dose/$AUC_{0-24,D7}$, where Dose=2×14.66 mg)

Tables summarizing the arithmetic means of the pharmacokinetic parameters (untransformed) are presented in Table 7 for dextromethorphan and Table 8 for dextrorphan. Geometric means, ratio of geometric means, and their associated 90% confidence intervals and intra-subject CV (ISCV %) values based on ANOVA (ln-transformed) are provided in Table 9 for dextromethorphan and Table 10 for dextrorphan. Results of the analysis for evaluation of steady state by Helmert contrasts are provided in Table 11 for dextromethorphan and Table 12 for dextrorphan.

For Treatment A (Test A, patch), mean plasma concentrations of dextromethorphan from the first application of the patch increased over the first 16 hours at which time concentrations were maintained near the mean $C_{max,D1}$ of 10990 pg/mL (median $T_{max,D1}$: 18.0 hours) with minimal fluctuation in concentration until the patch was removed at 24 hours post-application. For most subjects, concentrations reached a plateau by 10-14 hours post-application and concentrations stabilized by Day 3 and remained relatively constant over the next 4 days as indicated from the evaluation of the pre-dose concentrations over that time period by the Helmert contrast method for attainment of steady state, in which the least-squares geometric mean (LSGM) ratio of the morning pre-dose dextromethorphan concentrations for the Helmert contrasts were >90% from Day 3 onwards (p=0.0941 for the Day 3 vs. Days 4-7 contrast). By Day 7, there was small fluctuation in concentrations of dextromethorphan (mean fluctuation: 0.41) and dextrorphan (mean fluctuation: 0.43) over the 24-hour application period of the last patch, with mean peak dextromethorphan concentrations of 17866 pg/mL attained at a median $T_{max,D7}$ of 11.9 hours. The AUC accumulation factor from Day 1 to Day 7 is similar for both analytes at 2.1 for dextromethorphan and 2.5 for dextrorphan. Following patch removal on Day 8, concentrations of dextromethorphan and dextrorphan decreased with a mean terminal half-life of 17 and 18 hours, respectively.

For Treatment B (Reference B, NUEDEXTA® capsule), the mean peak plasma exposure of dextromethorphan on Day 1 (9691 pg/mL) was similar to that of Test A (10990 pg/mL). However, the degree of inhibition of dextromethorphan metabolism to dextrorphan by quinidine was more pronounced on Day 7 compared to Day 1 for Reference B as indicated by the high mean accumulation factor of 8.5 for dextromethorphan and the much lower mean accumulation factor of 1.9 for dextrorphan and the approximate 5-fold higher metabolic $AUC_{0-12}$ ratio of dextromethorphan to dextrorphan on Day 7 compared to Day 1 (i.e., geometric mean $MR_{D7}/MR_{D1}$=4.81; see Table 9); similar results were observed for $C_{max}$ using Days 1 and 7 data.

The maximal inhibition effect of quinidine stabilized by Day 7 as indicated by the similarity of the mean $CL_o$ values for the morning 0-12 hr dosing interval (27.0 L/hr) and the combined morning and evening dosing intervals over 0-24 hours (26.8 L/hr) and from the steady-state analysis in which at least 90% of theoretic steady-state appears to have been attained by Day 6 based on the LSGM ratio of 93.3% for the morning pre-dose dextromethorphan concentrations on Day 6 ($C_{pre,D6M}$) relative to those on Day 7 ($C_{pre,D7M}$ and $C_{24,D7}$). The p-values for the three Helmert contrasts were highly statistically significant (p<0.001; see Table 11), suggesting that steady state was not achieved by Day 7; however, the low residual variability in the ANOVA increased the likelihood of detecting a statistically significant difference between small differences (<10%) in Helmert contrast means.

$CL_o$ (Reference B geometric mean: 25.8 L/h) was approximately 4.4-fold lower than $CL_{TD}$ (Test A geometric mean: 113.9 L/h) on Day 7. This difference in multiple-dose characteristics for the test and reference products led to an approximate 75% lower dextromethorphan bioavailability of Test A relative to Reference B over 24 hours on Day 7, with LSGM test-to-reference (A/B) ratios of 25.56% for $C_{max,D7}$, 27.60% for $C_{24,D7}$, and 26.89% for $AUC_{0-24,D7}$. All 20 subjects with the exception of one had lower dextromethorphan concentrations for Test A on Day 7; this subject had the highest dextromethorphan concentrations on Days 1 and 7 for Test A and, as confirmed by genetic analysis, is a poor CYP2D6 metabolizer.

The results of the metabolic genotyping show that one subject is genetically a poor CYP2D6 metabolizer. The other subjects are characterized as either an extensive metabolizer (N=3), heterozygous extensive metabolizer (N=13), or intermediate metabolizer (N=3).

TABLE 7

Summary of Pharmacokinetic Parameters of Untransformed Data: Dextromethorphan (N = 20 Subjects)

| Pharmacokinetic Parameter | Treatment | N (# datasets) | Arithmetic mean ± SD (% CV) | Min. | Median | Max. |
|---|---|---|---|---|---|---|
| $AUC_{0-12, D1}$ (h · pg/mL) | Treatment B | 20 | 74749.8783 ± 28549.6993 (38.1936) | 35030.6866 | 74799.3242 | 135180.7672 |
| $AUC_{0-12, D7}$ (h · pg/mL) | Treatment B | 20 | 590311.6966 ± 167524.0182 (28.3789) | 337053.3026 | 579940.9683 | 850897.8813 |
| $AUC_{0-24, D1}$ (h · pg/mL) | Treatment A | 20 | 173497.4718 ± 90219.2496 (52.0003) | 41103.5929 | 149302.7639 | 497616.1227 |
| $AUC_{0-24, D7}$ (h · pg/mL) | Treatment A | 20 | 362124.6113 ± 334768.3153 (92.4456) | 191630.3303 | 272209.9582 | 1750394.8187 |
| | Treatment B | 20 | 1191241.9002 ± 345537.0485 (29.0065) | 679265.4702 | 1174568.9794 | 1697903.5327 |
| AF | Treatment A | 20 | 2.0759 ± 0.8105 (39.0434) | 1.2809 | 1.8501 | 4.7188 |
| | Treatment B | 20 | 8.5144 ± 2.3855 (28.0173) | 4.0805 | 8.0371 | 12.8133 |
| $C_{avg, D7}$ (pg/mL) | Treatment A | 20 | 15088.5255 ± 13948.6798 (92.4456) | 7984.5971 | 11342.0816 | 72933.1174 |
| | Treatment B | 20 | 49635.0792 ± 14397.3770 (29.0065) | 28302.7279 | 48940.3741 | 70745.9805 |
| $C_{max, D1}$ (pg/mL) | Treatment A | 20 | 10989.9847 ± 5795.5719 (52.7350) | 4263.3660 | 8944.8775 | 32944.0210 |
| | Treatment B | 20 | 9690.5274 ± 3424.3085 (35.3367) | 4724.6210 | 10662.7945 | 15917.7240 |
| $C_{max, D7}$ (pg/mL) | Treatment A | 20 | 17865.6858 ± 15775.7763 (88.3021) | 9213.3210 | 13138.7760 | 82812.8870 |
| | Treatment B | 20 | 61700.5645 ± 16511.9569 (26.7614) | 39193.8300 | 60308.4300 | 90147.9910 |
| $C_{min, D7}$ (pg/mL) | Treatment A | 20 | 12092.4403 ± 12276.9695 (101.5260) | 6037.2890 | 8726.7595 | 62889.5040 |
| | Treatment B | 20 | 40394.4418 ± 12376.7894 (30.6398) | 22151.4030 | 39598.4405 | 57874.7400 |
| $C_{pre, D1}$ (pg/mL) | Treatment A | 20 | 14.0873 ± 34.4580 (244.6031) | 0.0000 | 0.0000 | 139.5630 |
| | Treatment B | 20 | 28.7087 ± 91.2132 (317.7196) | 0.0000 | 0.0000 | 356.8110 |
| $C_{12, D1}$ (pg/mL) | Treatment B | 20 | 5080.4012 ± 2678.3464 (52.7192) | 1604.0240 | 4292.3540 | 12433.7990 |
| $C_{pre, D2}$ (pg/mL) | Treatment A | 20 | 9360.1350 ± 5320.0443 (56.8373) | 4263.3660 | 7891.7970 | 29614.3410 |
| $C_{pre, D3}$ (pg/mL) | Treatment A | 20 | 12648.9563 ± 10242.0583 (80.9716) | 3347.2760 | 9770.9730 | 53932.5140 |
| $C_{pre, D4}$ (pg/mL) | Treatment A | 20 | 12869.1112 ± 10762.8614 (83.6333) | 6764.8410 | 9846.3280 | 56888.4080 |
| $C_{pre, D5}$ (pg/mL) | Treatment A | 20 | 14582.1165 ± 12594.6677 (86.3706) | 7976.5680 | 11578.1740 | 66568.9520 |
| | Treatment B | 20 | 35200.2017 ± 10467.5805 (29.7373) | 20315.0190 | 33427.2925 | 51317.7370 |
| $C_{pre, D5E}$ (pg/mL) | Treatment B | 20 | 37782.7440 ± 12377.1998 (32.7589) | 20525.3120 | 36752.3675 | 56851.8030 |
| $C_{pre, D6}$ (pg/mL) | Treatment A | 20 | 14725.1713 ± 14099.0198 (95.7477) | 7078.7980 | 12319.7660 | 72959.1750 |
| | Treatment B | 20 | 39428.2443 ± 12572.5958 (31.8873) | 19765.4650 | 38317.4880 | 59970.8530 |
| $C_{pre, D6E}$ (pg/mL) | Treatment B | 20 | 42544.5810 ± 12575.2701 (29.5579) | 21253.1930 | 41212.0725 | 60461.5370 |
| $C_{pre, D7}$ (pg/mL) | Treatment A | 20 | 13571.7371 ± 12496.0394 (92.0740) | 7045.9950 | 9933.3260 | 65388.2150 |
| | Treatment B | 20 | 40552.6744 ± 12740.3226 (31.4167) | 20230.4080 | 41582.4950 | 61702.1890 |
| $C_{pre, D7E}$ (pg/mL) | Treatment B | 20 | 45076.5851 ± 14152.4416 (31.3964) | 24386.1040 | 43413.8095 | 65578.1190 |
| $C_{24, D7}$ (pg/mL) | Treatment A | 20 | 13522.7628 ± 12641.2673 (93.4814) | 8151.9820 | 10043.3315 | 66065.9430 |
| | Treatment B | 20 | 43744.6516 ± 13493.9408 (30.8471) | 22151.4030 | 43092.8670 | 64496.8970 |
| Fluctuation | Treatment A | 20 | 0.4078 ± 0.1581 (38.7568) | 0.1867 | 0.3726 | 0.8002 |
| | Treatment B | 20 | 0.4443 ± 0.1106 (24.8976) | 0.2554 | 0.4609 | 0.6368 |
| Swing | Treatment A | 20 | 0.5499 ± 0.2936 (53.3999) | 0.2034 | 0.4679 | 1.3450 |
| | Treatment B | 20 | 0.5563 ± 0.1645 (29.5650) | 0.2904 | 0.5589 | 0.9124 |

TABLE 7-continued

| Summary of Pharmacokinetic Parameters of Untransformed Data: Dextromethorphan (N = 20 Subjects) | | | | | | |
|---|---|---|---|---|---|---|
| Pharmacokinetic Parameter | Treatment | N (# datasets) | Arithmetic mean ± SD (% CV) | Min. | Median | Max. |
| $T_{max, D1}$ (h) | Treatment A | 20 | 17.5417 ± 4.9779 (28.3776) | 8.0000 | 18.0000 | 23.9167 |
| | Treatment B | 20 | 4.5500 ± 1.0748 (23.6227) | 3.0000 | 4.5000 | 7.0000 |
| $T_{max, D7}$ (h) | Treatment A | 20 | 10.8717 ± 5.1636 (47.4955) | 1.0000 | 11.9167 | 23.0000 |
| | Treatment B | 20 | 9.3000 ± 5.8858 (63.2877) | 3.0000 | 5.5000 | 17.0000 |
| $\lambda_{Z, D7}$ ($h^{-1}$) | Treatment A | 20 | 0.0449 ± 0.0122 (27.1314) | 0.0144 | 0.0464 | 0.0621 |
| $T_{1/2}$ (h) | Treatment A | 20 | 17.3676 ± 8.4036 (48.3866) | 11.1690 | 14.9559 | 48.0658 |
| $MR_{D1}$ | Treatment A | 20 | 19.8682 ± 31.6618 (159.3596) | 5.0607 | 12.1729 | 152.8822 |
| | Treatment B | 20 | 13.0873 ± 23.1221 (176.6763) | 2.1829 | 6.5359 | 108.2501 |
| $MR_{D7}$ | Treatment A | 20 | 15.8084 ± 21.1703 (133.9179) | 6.3042 | 10.3924 | 104.6071 |
| | Treatment B | 20 | 42.4546 ± 25.2430 (59.4587) | 14.7134 | 33.4066 | 95.8429 |
| $MR_{D7/D1}$ | Treatment A | 20 | 0.9033 ± 0.2278 (25.2190) | 0.5158 | 0.8460 | 1.3649 |
| | Treatment B | 20 | 5.3972 ± 2.2694 (42.0483) | 0.7879 | 5.0887 | 9.9310 |
| $CL_{TD}$ (L/h) Day 7, 0-24 h | Treatment A | 20 | 123.1313 ± 39.0268 (31.6953) | 19.9955 | 128.6349 | 182.6433 |
| $CL_o$ (L/h) Day 7, 0-12 h | Treatment B | 20 | 26.9530 ± 8.0535 (29.8797) | 17.2289 | 25.2806 | 43.4946 |
| $CL_o$ (L/h) Day 7, 0-24 h | Treatment B | 20 | 26.7942 ± 8.1175 (30.2957) | 17.2684 | 24.9664 | 43.1643 |

TABLE 8

| Summary of Pharmacokinetic Parameters of Untransformed Data: Dextrorphan (N = 20 Subjects) | | | | | | |
|---|---|---|---|---|---|---|
| Pharmacokinetic Parameter | Treatment | N (# datasets) | Arithmetic mean ± SD (% CV) | Min. | Median | Max. |
| $AUC_{0-12, D1}$ (h · pg/mL) | Treatment B | 20 | 10941.2584 ± 5906.2185 (53.9812) | 1248.7818 | 9246.4339 | 24029.6153 |
| $AUC_{0-12, D7}$ (h · pg/mL) | Treatment B | 20 | 17396.6525 ± 8518.8347 (48.9682) | 7680.6983 | 16211.1306 | 39781.3541 |
| $AUC_{0-24, D1}$ (h · pg/mL) | Treatment A | 20 | 13280.0698 ± 7410.7688 (55.8037) | 3254.9000 | 11733.1696 | 31956.4086 |
| $AUC_{0-24, D7}$ (h · pg/mL) | Treatment A | 20 | 27931.4517 ± 11707.8739 (41.9165) | 14290.4910 | 26066.1163 | 54518.0798 |
| | Treatment B | 20 | 32887.4655 ± 15491.5743 (47.1048) | 14527.8758 | 31071.0288 | 73123.2921 |
| AF | Treatment A | 20 | 2.5237 ± 1.3721 (54.3697) | 1.2745 | 2.0847 | 5.2555 |
| | Treatment B | 20 | 1.8691 ± 1.2227 (65.4185) | 1.0880 | 1.6792 | 6.9441 |
| $C_{avg, D7}$ (pg/mL) | Treatment A | 20 | 1163.8105 ± 487.8281 (41.9165) | 595.4371 | 1086.0882 | 2271.5867 |
| | Treatment B | 20 | 1370.3111 ± 645.4823 (47.1048) | 605.3282 | 1294.6262 | 3046.8038 |
| $C_{max, D1}$ (pg/mL) | Treatment A | 20 | 1017.9785 ± 550.3797 (54.0659) | 281.4560 | 944.5140 | 2427.0950 |
| | Treatment B | 20 | 1588.8104 ± 940.7736 (59.2125) | 150.9370 | 1212.3480 | 3552.2750 |
| $C_{max, D7}$ (pg/mL) | Treatment A | 20 | 1425.5856 ± 632.6479 (44.3781) | 694.9440 | 1265.5285 | 2772.0470 |
| | Treatment B | 20 | 1785.7439 ± 902.5064 (50.5395) | 746.0260 | 1612.7775 | 4092.8320 |
| $C_{min, D7}$ (pg/mL) | Treatment A | 20 | 918.5788 ± 398.6491 (43.3985) | 483.3670 | 826.9405 | 1996.3450 |
| | Treatment B | 20 | 1083.4733 ± 480.6176 (44.3590) | 531.3370 | 1018.8880 | 2337.4100 |
| $C_{pre, D1}$ (pg/mL) | Treatment A | 20 | 0.7097 ± 3.1739 (447.2136) | 0.0000 | 0.0000 | 14.1940 |
| | Treatment B | 20 | 1.1518 ± 5.1510 (447.2136) | 0.0000 | 0.0000 | 23.0360 |

TABLE 8-continued

Summary of Pharmacokinetic Parameters of Untransformed Data: Dextrorphan (N = 20 Subjects)

| Pharmacokinetic Parameter | Treatment | N (# datasets) | Arithmetic mean ± SD (% CV) | Min. | Median | Max. |
|---|---|---|---|---|---|---|
| $C_{12, D1}$ (pg/mL) | Treatment B | 20 | 549.4354 ± 271.0763 (49.3372) | 91.5650 | 467.2860 | 1140.8070 |
| $C_{pre, D2}$ (pg/mL) | Treatment A | 20 | 762.7322 ± 296.8505 (38.9194) | 276.6270 | 778.8505 | 1339.3210 |
| $C_{pre, D3}$ (pg/mL) | Treatment A | 20 | 1005.6861 ± 388.0801 (38.5886) | 153.1850 | 1006.6365 | 1836.9160 |
| $C_{pre, D4}$ (pg/mL) | Treatment A | 20 | 1025.3973 ± 376.1941 (36.6876) | 394.9870 | 1030.3735 | 1906.8200 |
| $C_{pre, D5}$ (pg/mL) | Treatment A | 20 | 1218.1316 ± 430.9240 (35.3758) | 513.4300 | 1181.7345 | 2154.3840 |
| | Treatment B | 20 | 1130.5131 ± 522.2663 (46.1973) | 505.2710 | 986.0370 | 2273.2350 |
| $C_{pre, D5E}$ (pg/mL) | Treatment B | 20 | 1057.0865 ± 504.1891 (47.6961) | 495.6660 | 889.7890 | 2343.6300 |
| $C_{pre, D6}$ (pg/mL) | Treatment A | 20 | 1255.6253 ± 465.6722 (37.0869) | 647.9560 | 1080.5655 | 2695.4550 |
| | Treatment B | 20 | 1406.0663 ± 917.2849 (65.2377) | 552.6460 | 1141.2230 | 4397.6500 |
| $C_{pre, D6E}$ (pg/mL) | Treatment B | 20 | 1213.8154 ± 615.1995 (50.6831) | 528.6060 | 1060.4475 | 2836.0930 |
| $C_{pre, D7}$ (pg/mL) | Treatment A | 20 | 1199.3382 ± 449.4199 (37.4723) | 542.8730 | 1135.8925 | 2112.5470 |
| | Treatment B | 20 | 1430.5356 ± 759.8106 (53.1137) | 554.4200 | 1236.5555 | 3384.2490 |
| $C_{pre, D7E}$ (pg/mL) | Treatment B | 20 | 1182.9137 ± 504.6730 (42.6635) | 549.5730 | 1126.7590 | 2649.7850 |
| $C_{24, D7}$ (pg/mL) | Treatment A | 20 | 1027.1005 ± 424.9580 (41.3745) | 503.3570 | 887.8505 | 2015.2690 |
| | Treatment B | 20 | 1253.9823 ± 578.0895 (46.1003) | 580.5010 | 1178.1280 | 2925.2220 |
| Fluctuation | Treatment A | 20 | 0.4247 ± 0.1207 (28.4314) | 0.1945 | 0.4281 | 0.6399 |
| | Treatment B | 20 | 0.4839 ± 0.1610 (33.2648) | 0.2497 | 0.4502 | 0.8369 |
| Swing | Treatment A | 20 | 0.5487 ± 0.1869 (34.0649) | 0.2172 | 0.5531 | 0.8859 |
| | Treatment B | 20 | 0.6203 ± 0.2589 (41.7329) | 0.2917 | 0.5550 | 1.2505 |
| $T_{max, D1}$ (h) | Treatment A | 20 | 17.1375 ± 4.9158 (28.6847) | 8.0000 | 16.0000 | 23.9167 |
| | Treatment B | 20 | 4.0250 ± 0.8347 (20.7377) | 3.0000 | 4.5000 | 5.5000 |
| $T_{max, D7}$ (h) | Treatment A | 20 | 8.2592 ± 5.5422 (67.1039) | 1.0000 | 8.0000 | 22.0000 |
| | Treatment B | 20 | 4.9000 ± 5.1951 (106.0233) | 2.0000 | 3.0000 | 24.0000 |
| $\lambda_{Z, D7}$ ($h^{-1}$) | Treatment A | 20 | 0.0403 ± 0.0089 (22.1030) | 0.0248 | 0.0402 | 0.0576 |
| $T_{1/2}$ (h) | Treatment A | 20 | 18.0794 ± 4.4110 (24.3976) | 12.0342 | 17.2724 | 27.9121 |

TABLE 9

Summary of Comparative Bioavailability Results Based on Plasma Dextromethorphan Concentrations

| Parameter | Trt | LS Geometric Mean | Contrast (# subjects) | LSGM Ratio (%) | 90% Confidence Interval (%) | ISCV(%) | P-value Period | P-value Sequence |
|---|---|---|---|---|---|---|---|---|
| $C_{max, D7}$ (pg/mL) | A | 15234 | A vs B (n = 20) | 25.56 | 20.39-32.04 | 43.0 | 0.7646 | 0.3200 |
| | B | 59600 | | | | | | |
| $C_{24, D7}$ (pg/mL) | A | 11496 | A vs B (n = 20) | 27.60 | 22.90-33.28 | 35.1 | 0.1679 | 0.2698 |
| | B | 41649 | | | | | | |
| $AUC_{0-24, D7}$ (h · pg/mL) | A | 307250 | A vs B (n = 20) | 26.89 | 21.60-33.49 | 41.6 | 0.6610 | 0.2931 |
| | B | 1142418 | | | | | | |

TABLE 10

Summary of Comparative Bioavailability Results Based on Plasma Dextrorphan Concentrations

| Parameter | Trt | LS Geometric Mean | Contrast (# subjects) | LSGM Ratio (%) | 90% Confidence Interval (%) | ISCV(%) | P-value Period | P-value Sequence |
|---|---|---|---|---|---|---|---|---|
| $C_{max, D7}$ (pg/mL) | A | 1304 | A vs B (n = 20) | 81.30 | 69.76-94.74 | 28.5 | 0.0611 | 0.9647 |
| | B | 1603 | | | | | | |
| $C_{24, D7}$ (pg/mL) | A | 950.8 | A vs B (n = 20) | 82.68 | 72.79-93.90 | 23.5 | 0.1498 | 0.6527 |
| | B | 1150 | | | | | | |
| $AUC_{0-24, D7}$ (h · pg/mL) | A | 25789 | A vs B (n = 20) | 85.99 | 75.28-98.21 | 24.6 | 0.0569 | 0.7551 |
| | B | 29992 | | | | | | |

TABLE 11

Summary of Steady-State Results Based on Morning Pre-Dose Plasma Dextromethorphan Concentrations

| Contrast | p-value (Differ-ence) | LSMean Ratio (%) |
|---|---|---|
| Treatment A | | |
| Day 2 vs. Days 3, 4, 5, 6, Day 7 (pre), Day 7 (24 h) | <0.0001 | 73.3 |
| Day 3 vs. Days 4, 5, 6, Day 7 (pre), Day 7 (24 h) | 0.0941 | 91.6 |
| Day 4 vs. Days 5, 6, Day 7 (pre), Day 7 (24 h) | 0.0059 | 92.7 |
| Day 5 vs. Days 6, Day 7 (pre), Day 7 (24 h) | 0.0092 | 106.6 |
| Day 6 vs. Days Day 7 (pre), Day 7 (24 h) | 0.0593 | 106.9 |
| Day 7 (pre) vs. Day 7 (24 h) | 0.8234 | 100.4 |
| Treatment B | | |
| Day 5 vs. Days 6, Day 7 (pre), Day 7 (24 h) | <0.0001 | 86.0 |
| Day 6 vs. Days Day 7 (pre), Day 7 (24 h) | 0.0002 | 93.3 |
| Day 7 (pre) vs. Day 7 (24 h) | 0.0003 | 92.5 |

TABLE 12

Summary of Steady-State Results Based on Morning Pre-Dose Plasma Dextrorphan Concentrations

| Contrast | p-value (Differ-ence) | LSMean Ratio (%) |
|---|---|---|
| Treatment A | | |
| Day 2 vs. Days 3, 4, 5, 6, Day 7 (pre), Day 7 (24 h) | <0.0001 | 67.8 |
| Day 3 vs. Days 4, 5, 6, Day 7 (pre), Day 7 (24 h) | 0.1623 | 84.7 |
| Day 4 vs. Days 5, 6, Day 7 (pre), Day 7 (24 h) | 0.0011 | 87.3 |
| Day 5 vs. Days 6, Day 7 (pre), Day 7 (24 h) | 0.1364 | 105.9 |
| Day 6 vs. Days Day 7 (pre), Day 7 (24 h) | 0.0339 | 115.0 |
| Day 7 (pre) vs. Day 7 (24 h) | 0.0005 | 118.0 |
| Treatment B | | |
| Day 5 vs. Days 6, Day 7 (pre), Day 7 (24 h) | <0.0001 | 85.4 |
| Day 6 vs. Days Day 7 (pre), Day 7 (24 h) | 0.9310 | 100.5 |
| Day 7 (pre) vs. Day 7 (24 h) | 0.0167 | 110.5 |

Overall, the pharmacokinetic results show that drug release from the patch is consistent over the 7 days, with a drug accumulation factor of 2.1 at steady state and small fluctuation in dextromethorphan concentrations.

Differences in multiple-dose characteristics for the test and reference products led to an approximate 75% lower dextromethorphan bioavailability of Test A relative to Reference B over 24 hours on Day 7, with LSGM test-to-reference ratios of 25.56% for $C_{max,D7}$, 27.60% for $C_{24,D7}$, and 26.89% for $AUC_{0-24,D7}$. All 20 subjects with the exception of one subject had lower dextromethorphan concentrations for Test A on Day 7; this subject had the highest dextromethorphan concentrations on Days 1 and 7 for Test A and is phenotypically and genotypically a poor CYP2D6 metabolizer. These data suggest that the relative bioavailability of dextromethorphan from the patch compared to the NUEDEXTA® capsule under multiple-dose conditions may be influenced by the CYP2D6 metabolizer status of the subjects.

In summary, the relative bioavailability of dextromethorphan was approximately 4-fold lower following a once-daily application of the Dextromethorphan Patch, 35 mg/24 hr for 7 days compared to NUEDEXTA® (dextromethorphan hydrobromide and quinidine sulfate) capsule, 1×20 mg/10 mg administered orally every 12 hours for 7 days under fasted conditions. This lower relative bioavailability from the patch compared to the oral capsule on Day 7 resulted from a higher degree of inhibition of dextromethorphan metabolism to dextrorphan by quinidine on Day 7 compared to Day 1 for the reference product.

Based on the similarity of geometric mean $CL_{TD}$ (patch) values from this study (113.9 L/h on Day 7 of once-daily application of Dextromethorphan Patch, 35 mg/24 hr) and the study following Example 4A (93.4 L/h on Day 1 for a single application of Dextromethorphan Patch, 15 mg/24 hr), the pharmacokinetics of dextromethorphan from the patch appears linear (i.e., independent of dose and time), whereas the pharmacokinetics of dextromethorphan from the NUEDEXTA® (dextromethorphan hydrobromide and quinidine sulfate) capsule is non-linear as a result of the time-dependent inhibition of dextromethorphan metabolism by quinidine.

The $CL_{TD}$ and $CL_o$ values were very similar on Day 1 in study shown in Example 4A, as indicated from the dose-normalized $AUC_{0-\infty}$ geometric mean ratio of 1.07, which means that total plasma exposures (AUC) of dextromethorphan should be similar in patch and capsule over 24 hr on Day 1 for similar daily doses. Whereas $CL_o$ is approximately 4.4-fold lower than $CL_{TD}$ on Day 7 in this study, which indicates that the inhibition effect of quinidine on CYP2D6 metabolism of dextromethorphan is time-dependent and increases in magnitude from Day 1 to Day 7. Therefore, increasing the dose from 15 mg/24 hr to 35 mg/24 hr based on the Day 1 pharmacokinetic data from study shown in Example 4A to achieve similar plasma exposures for patch and capsule over the initial 24 hours of dosing and the subsequent decrease of approximately 4-fold in peak and total plasma exposures relative to the capsule during multiple-dose therapy (Day 7) is not unexpected given the non-linear, time-dependent pharmacokinetic characteristics of dextromethorphan from the capsule. Consequently, there is no possibility to consistently achieve similar systemic exposures of dextromethorphan in the patch and capsule from single dose (Day 1) to multiple dose (Day 7) without changing the dosing regimen of patch.

Residue Dextromethorphan analysis

Applied (worn) patch returned from the clinical site were evaluated for dextromethorphan content. A fully validated HPLC method was used to determine the identity and content of dextromethorphan in the transdermal delivery systems.

Each patch was extracted by sonicating it in extraction solvents, methanol/water, without heat, and then quantifying the extracted dextromethorphan by isocratic reversed phase HPLC with UV detection. Elution is effected with a mobile phase containing: Mobile Phase A: Acetonitrile:Methanol (80:20), and Mobile Phase B: Water. The ratio of Mobile Phase A: Mobile Phase B is 78:22 (with 0.1% Trifluoroacetic acid). The column is a Gemini C18, 5 μm, 150×4.6 mm, 110 A, maintained at 40° C., and a UV detector set at 360 nm.

The results (Tables 13A/13B) show that the mean residual dextromethorphan in the worn patches range from about 14.9 mg to about 23.6 mg. Thus, the daily amount of dextromethorphan delivered is about 32.4 mg to about 41.1 mg, consistent with the predicted 35 mg delivery based on in vitro flux data.

TABLE 13A

Residue Dextromethophan in Each Worn Patch (mg/Patch) for Period 1

| Subject | Day 1 | Day 2 | Day 3 | Day 4 | Day 5 | Day 6 | Day 7 |
|---|---|---|---|---|---|---|---|
| 3001 | 20.1 | 19.2 | 21.8 | 22.9 | 23.3 | 28.5 | 17.5 |
| 3003 | 28.3 | 29.7 | 26.6 | 22.8 | 27.1 | 32.5 | 22.4 |
| 3006 | 9.3 | 14.1 | 13.7 | 11.5 | 13.3 | 18.9 | 9.0 |
| 3007 | 14.0 | 14.0 | 14.1 | 12.2 | 15.4 | 17.9 | 10.4 |
| 3009 | 15.1 | 14.8 | 17.3 | 10.3 | 14.9 | 10.8 | 9.1 |
| 3012 | 25.4 | 22.9 | 21.9 | 21.0 | 22.1 | 22.0 | 14.5 |
| 3014 | 28.3 | 28.4 | 27.5 | 24.7 | 21.5 | 34.0 | 20.1 |
| 3015 | 22.6 | 21.7 | 19.9 | 21.6 | 21.4 | 26.4 | 12.7 |
| 3017 | 19.6 | 15.2 | 18.5 | 16.4 | 19.9 | 23.7 | 15.6 |
| 3020 | 22.8 | 21.0 | 25.0 | 21.2 | 28.5 | 21.8 | 17.3 |
| Mean, mg | 20.5 | 20.1 | 20.6 | 18.5 | 20.7 | 23.6 | 14.9 |
| Delivered mg | 35.5 | 35.9 | 35.4 | 37.5 | 35.3 | 32.4 | 41.1 |

TABLE 13B

Residue Dextromethophan in Each Worn Patch (mg/Patch) for Period 2

| Subject | Day 1 | Day 2 | Day 3 | Day 4 | Day 5 | Day 6 | Day 7 |
|---|---|---|---|---|---|---|---|
| 3002 | 19.3 | 15.2 | 21.3 | 16.2 | 15.3 | 13.7 | 14.5 |
| 3004 | 23.8 | 20.9 | 23.6 | 10.3 | 11.5 | 22.7 | 25.2 |
| 3005 | 22.7 | 22.9 | 27.9 | 23.0 | 15.6 | 23.2 | 25.2 |
| 3008 | 16.3 | 18.0 | 17.0 | 17.0 | 12.3 | 16.6 | 25.7 |
| 3010 | 18.3 | 16.0 | 18.8 | 16.7 | 17.7 | 21.4 | 23.7 |
| 3011 | 14.6 | 12.3 | 18.9 | 10.2 | 11.3 | 23.2 | 7.5 |
| 3013 | 35.2 | 31.4 | 28.8 | 30.0 | 32.1 | 30.8 | 31.4 |
| 3016 | 8.5 | 7.9 | 6.4 | 6.5 | 8.1 | 9.7 | 9.7 |
| 3018 | 23.3 | 20.2 | 24.5 | 19.8 | 14.9 | 24.0 | 26.1 |
| 3019 | 19.5 | 19.4 | 13.3 | 14.6 | 23.6 | 12.2 | 12.3 |
| Mean | 20.1 | 18.4 | 20.0 | 16.4 | 16.2 | 19.8 | 20.1 |
| Delivered mg | 35.9 | 37.6 | 36.0 | 39.6 | 39.8 | 36.2 | 35.9 |

Example 5. Multilayer Patch Design

In this example, a novel multilayer design is described.

As shown in FIG. 5, an exemplary patch design useful for the embodiments herein can include a contact layer and a reservoir layer. The contact layer (top layer in FIG. 5) can have the following ingredients: 1) an Adhesive (e.g., DURO-TAK 87-2287): about 77.5%-about 75%; 2) Drug (Dextromethorphan base): about 10%; 3) Enhancer (e.g., Isopropyl Myristate—IPM): about 10%; and 4) a Kollidon, e.g., KollidonVA64: about 2.5%-about 5%. The reservoir layer can have the following ingredients: 1) an Adhesive (e.g., DURO-TAK 87-2287): about 57.5%-about 20%; 2) Drug (Dextromethorphan base): about 30%-about 50%; 3) Enhancer (e.g., Isopropyl Myristate—IPM): about 10%; and 4) a Kollidon e.g., Kollidon VA64: about 2.5%-about 20%. The bottom layer can be a backing layer or can be an adhesive layer such as the same as the top layer. Suitable backing layers are described herein. Kollidon is a brand-name which refers to a vinylpyrrolidone polymer (e.g., a vinylpyrrolidone-vinyl acetate copolymers, e.g., Kollidon VA64). Prior to application, the contact layer is typically protected with a release liner. Suitable release liners are also described herein.

In one example, the multilayer patch can have a size of 60 $cm^2$ or more, e.g., about 60 $cm^2$ to about 150 $cm^2$.

In one example, the multilayer patch can have a size of 70 $cm^2$, which is designed to contain a total of about 370 mg dextromethorphan base. Such patch is suitable for application for 7 days, which can transdermally deliver about 20 mg or more of dextromethorphan per day for 7 days (total delivery approximately 140 mg or more) over 7 days).

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A method of treating pseudobulbar affect in a subject in need thereof, the method comprising applying a transdermal patch to the subject, wherein the transdermal patch comprises:

(a) a backing layer; and (b) a drug-in-adhesive layer comprising (1) dextromethorphan in an amount of about 6% to about 12% by weight; (2) isopropyl myristate in an amount of about 6% to about 12% by weight; (3) a pressure sensitive adhesive in an amount of about 65% to about 85% by weight; and optionally (4) a crystallization inhibitor in amount of about 6% to about 12% by weight, wherein the drug-in-adhesive layer comprises dextromethorphan as the only active ingredient, wherein the subject does not suffer from a cough and/or does not need an antitussive, and wherein the transdermal patch has an active surface area of about 30 $cm^2$ to about 100 $cm^2$.

2. The method of claim 1, wherein the pressure sensitive adhesive is a poly acrylate vinyl acetate copolymer pressure sensitive adhesive.

3. The method of claim 2, wherein the drug-in-adhesive layer comprises the crystallization inhibitor in an amount of about 6% to about 12% by weight.

4. The method of claim 3, wherein the crystallization inhibitor is a vinylpyrrolidone polymer.

5. The method of claim 4, wherein the drug-in-adhesive layer comprises 1) about 20 mg to about 100 mg of dextromethorphan; 2) about 30 mg to about 100 mg of isopropyl myristate; 3) about 150 mg to about 900 mg of the pressure sensitive adhesive; and 4) the crystallization inhibitor in an amount of about 30 mg to about 100 mg.

6. The method of claim 1, comprising applying the transdermal patch to transdermally deliver a daily dose of about 15 mg to about 50 mg of dextromethorphan to the subject.

7. The method of claim 1, wherein the subject (i) is characterized as an extensive metabolizer of dextromethorphan; (ii) is characterized as a poor metabolizer of dextromethorphan; (iii) is sensitive or intolerant to CYP2D6 inhibitors; (iv) has one or more side effects associated with quinidine; and/or (v) is co-administered a drug whose metabolism is affected by a CYP2D6 inhibitor.

8. The method of claim 1, further comprising administering to the subject an antidepressant.

9. A method of treating pseudobulbar affect in a subject in need thereof, the method comprising applying a transdermal patch to the subject at a dosing frequency of once a day to once a week, wherein the transdermal patch comprises about 15 mg to about 700 mg of dextromethorphan as the only drug, wherein the subject does not suffer from a cough and/or does not need an antitussive, and wherein the applying results in a therapeutically effective plasma concentration of dextromethorphan in the subject at steady state.

10. The method of claim 9, wherein the transdermal patch comprises about 30 mg to about 100 mg of dextromethorphan, and the applying results in a pharmacokinetic profile in the subject characterized by one or more of the following:

a) an $AUC_{0-24}$, DXM at day-7 or steady state stage between about 180 h*ng/mL to about 2000 h*ng/mL;

b) a $C_{Avg, DXM}$ at day-7 or steady state stage between about 8 ng/ml to about 100 ng/ml;

c) a $C_{min, DXM}$ at day-7 or steady state stage between about 6 ng/mL to about 65 ng/mL;

d) a $C_{max, DXM}$ at day-7 or steady state stage between about 8 ng/ml to about 90 ng/mL;

e) a degree of fluctuation $[(C_{max}-C_{min})/C_{avg}]$ for dextromethorphan at day-7 or steady state stage between about 0.18 to about 0.8, e.g., about 0.18 to about 0.8;

f) a swing $[(C_{max}-C_{min})/C_{min}]$ for dextromethorphan at day-7 or steady state stage between about 0.2 to about 1.35;

g) a ratio of $AUC_{0-24, DXM}$ at steady state stage to $AUC_{0-24, DXM, D1}$ about 1.5 to about 5;

h) a ratio of $AUC_{0-24, DXM}$ to $AUC_{0-24, DOR}$ at steady state stage of about 12 to about 35;

i) a ratio of $C_{max, DXM}$ to $C_{max, DOR}$ at steady state stage of about 12 to about 35; and j) a ratio of $C_{Avg, DXM}$ to $C_{Avg, DOR}$ at steady state stage of about 12 to about 35.

11. The method of claim 9, wherein for each application of the transdermal patch other than the first dose, the pre-dosing plasma concentration of dextromethorphan does not go below about 20% of the average concentration ($C_{Avg, DXM}$) observed for the immediate previous dose; and/or the accumulation factor of dextromethorphan ranges from about 1 to about 5, wherein the subject is an extensive metabolizer or ultra-extensive metabolizer.

12. The method of claim 9, wherein the applying results in k) a half-life of dextromethorphan at steady state stage between about 11 to about 29 hours, in an extensive metabolizer or ultra-extensive metabolizer; and/or 1) an Apparent first-order terminal disposition rate constant ($\lambda_z$) following the last dose after achieving steady state stage between about 0.018 $h^{-1}$ to about 0.065 $h^{-1}$ in an extensive metabolizer or ultra-extensive metabolizer.

13. The method of claim 9, wherein the applying transdermally delivers a daily dose of about 15 mg to about 50 mg of dextromethorphan to the subject.

14. The method of claim 9, wherein the subject (i) is characterized as an extensive metabolizer of dextromethorphan; (ii) is characterized as a poor metabolizer of dextromethorphan; (iii) is sensitive or intolerant to CYP2D6 inhibitors; (iv) has one or more side effects associated with quinidine; and/or (v) is co-administered a drug whose metabolism is affected by a CYP2D6 inhibitor.

15. The method of claim 9, wherein the transdermal patch comprises a backing layer and a drug-in-adhesive layer, wherein the drug-in-adhesive layer comprises dextromethorphan as the only active ingredient, and the drug-in-adhesive layer comprises dextromethorphan in an amount of about 6% to about 12% by weight; isopropyl myristate in an amount of about 6% to about 12% by weight; a pressure sensitive adhesive in an amount of about 65% to about 85% by weight, and a crystallization inhibitor in an amount of about 6% to about 12% by weight.

16. The method of claim 15, wherein the pressure sensitive adhesive is a poly acrylate vinyl acetate copolymer pressure sensitive adhesive; and the drug-in-adhesive layer comprises the crystallization inhibitor, which is a vinylpyrrolidone polymer.

17. The method of claim 1, wherein the transdermal delivery device or patch is applied once a day, and the residue amount of dextromethorphan in the transdermal patch is less than 50% of the initial dextromethorphan amount in the transdermal patch; and/or the percentage of dextromethorphan delivered to the subject is about 50% to about 80% of the initial dextromethorphan amount in the patch.

* * * * *